US008709445B2

(12) United States Patent
Craft et al.

(10) Patent No.: US 8,709,445 B2
(45) Date of Patent: Apr. 29, 2014

(54) VACCINATION WITH KILLED BUT METABOLICALLY ACTIVE (KBMA) PROTOZOANS WITH TOLL-LIKE RECEPTOR AGONISTS

(75) Inventors: Noah A. Craft, Venice, CA (US); Kevin W. Bruhn, Santa Monica, CA (US); Ron A. Birnbaum, Los Angeles, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 697 days.

(21) Appl. No.: 12/671,184

(22) PCT Filed: Jul. 31, 2008

(86) PCT No.: PCT/US2008/071802
§ 371 (c)(1),
(2), (4) Date: Jul. 29, 2010

(87) PCT Pub. No.: WO2009/018465
PCT Pub. Date: Feb. 5, 2009

(65) Prior Publication Data
US 2010/0310606 A1 Dec. 9, 2010

Related U.S. Application Data

(60) Provisional application No. 60/953,159, filed on Jul. 31, 2007.

(51) Int. Cl.
| A61K 39/00 | (2006.01) |
| A61K 39/002 | (2006.01) |
| A61K 39/012 | (2006.01) |
| A61K 39/015 | (2006.01) |
| A61K 39/018 | (2006.01) |
| C12N 13/00 | (2006.01) |

(52) U.S. Cl.
USPC .................. 424/265.1; 424/269.1; 424/270.1; 424/271.1; 424/272.1; 424/273.1; 435/173.1

(58) Field of Classification Search
None
See application file for complete search history.

(56) References Cited

U.S. PATENT DOCUMENTS

| 4,582,789 A | 4/1986 | Sheldon, III et al. |
| 4,826,967 A | 5/1989 | Glass |
| 4,999,375 A | 3/1991 | Bachynsky et al. |
| 5,036,102 A | 7/1991 | Bachynsky et al. |
| 5,618,662 A | 4/1997 | Lin et al. |
| 5,625,079 A | 4/1997 | Wollowitz et al. |
| 5,709,991 A | 1/1998 | Lin et al. |
| 5,919,935 A | 7/1999 | Platz et al. |
| 6,218,100 B1 | 4/2001 | Wollowitz et al. |
| 6,264,952 B1 | 7/2001 | Enright et al. |
| 6,420,570 B1 | 7/2002 | Wollowitz et al. |
| 7,691,393 B2* | 4/2010 | Dubensky et al. ......... 424/235.1 |
| 7,892,562 B2* | 2/2011 | Karp .......................... 424/208.1 |
| 7,927,606 B2* | 4/2011 | Dubensky et al. ......... 424/234.1 |
| 7,935,804 B2* | 5/2011 | Dubensky et al. ........... 536/23.7 |
| 2004/0228877 A1* | 11/2004 | Dubensky et al. ......... 424/200.1 |
| 2006/0018877 A1* | 1/2006 | Mikszta et al. ............. 424/93.1 |
| 2006/0121060 A1 | 6/2006 | Kappe et al. |
| 2007/0190029 A1* | 8/2007 | Pardoll et al. ................ 424/93.2 |
| 2007/0190063 A1* | 8/2007 | Bahjat et al. ............... 424/155.1 |
| 2008/0248066 A1* | 10/2008 | Dubensky et al. ......... 424/248.1 |
| 2009/0028932 A1* | 1/2009 | Wilson et al. ................. 424/450 |
| 2010/0068230 A1* | 3/2010 | Dubensky et al. ......... 424/235.1 |
| 2010/0310606 A1* | 12/2010 | Craft et al. ................. 424/270.1 |
| 2011/0287055 A1* | 11/2011 | Lauer et al. ............... 424/235.1 |

FOREIGN PATENT DOCUMENTS

| EP | 1318835 | 6/2003 |
| WO | WO/2006/063152 | 6/2006 |
| WO | WO/2007/022511 | 2/2007 |
| WO | WO/2009/018465 | 2/2009 |
| WO | WO 2009/018465 A1 * | 2/2009 |

OTHER PUBLICATIONS

Roback et al, Blood, (Nov. 16, 2005) vol. 106, No. 11, Part 1, pp. 171A. Abstract only Meeting Info.: 47th Annual Meeting of the American-Socie Atlanta, GA, USA. Dec. 10-13, 2005.*
Brockstedt et al, Nature Medicine, Aug. 2005, 11/8:853-860.*
Eastman et al, vol. 45, Sep. 2005 Transfusion, pp. 1459-1463.*
Das et al, Clin. Vaccine Immunol. 19(4):490-498 (2012).*
Bruhn et al, CVI, Apr. 2012, 19/4:490-498.*
Lankowsky et al, The Journal of Infectious Diseases, Apr. 15, 2007; 195:1203-11.*
Coler et al, Trends in Parasitology, May 2005, 21/5:244-249.*
Dubensky et al, Current Opinion in Biotechnology, 2012, 23:917-923.*
PCT International Search Report and Written Opinion dated Dec. 4, 2008 issued in PCT/US2008/071802 (WO/2009/018465).
PCT International Preliminary Report on Patentability dated Feb. 2, 2010 issued in PCT/US2008/071802 (WO/2009/018465).
Brockstedt et al. (2005) "Killed but metabolically active microbes: a new vaccine paradigm for eliciting effector T-cell responses and protective Immunity" *Nature Medicine* Advance Online Publication pp. 1-8.

(Continued)

*Primary Examiner* — Nita M Minnifield
(74) *Attorney, Agent, or Firm* — Tom Hunter; Weaver Austin Villeneuve & Sampson LLP

(57) ABSTRACT

This invention provides compositions for inducing an immune response in a vertebrate host against a protozoan parasite. In certain embodiments the composition comprises a protozoan parasite comprising a psoralen-modified DNA, whereby said protozoan parasite is killed but metabolically active (KBMA); and optionally a Toll-like receptor agonist.

12 Claims, 18 Drawing Sheets

(56) References Cited

OTHER PUBLICATIONS

Brockstedt et al. (2005) "Killed but metabolically active microbes: a new vaccine paradigm for eliciting effector T-cell responses and protective Immunity" *Nature Medicine* 11(8): 853-60.

Lin et al. (1997) "Photochemical inactivation of viruses and bacteria in platelet concentrates by use of a novel psoralen and long-wavelength ultraviolet light." *Transfusion* 37(4): 423-435.

Miller et al. (1999) "Imiquimod applied topically: a novel immune response modifier and new class of drug." *Int J Immunophannacol.* 21(1): 1-14. [Abstract Only] 1 Page.

Truitt et al. (1999) "Photochemical Treatment with S-59 Psoralen and Ultraviolet A Light to Control the Fate of Naive or Primed T Lymphocytes in Vivo After Allogeneic Bone Marrow Transplantation" *The Journal of Immunology* 163: 5145-5156.

* cited by examiner

Psoralen

Isopsoralen

TMP

HMT

8-MOP

AMT

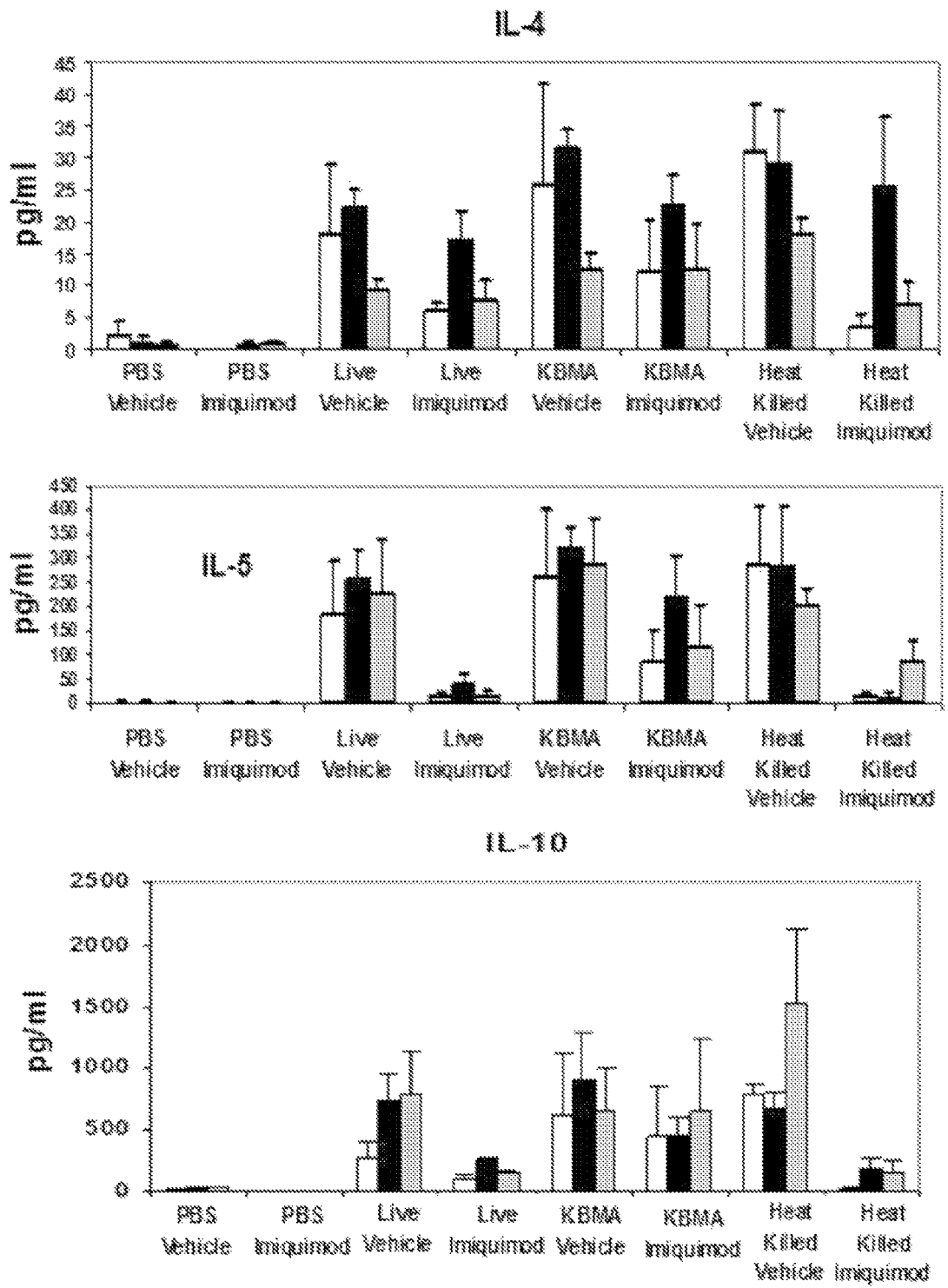
*Fig. 11C, cont'd.*

VACCINATION WITH KILLED BUT METABOLICALLY ACTIVE (KBMA) PROTOZOANS WITH TOLL-LIKE RECEPTOR AGONISTS

CROSS-REFERENCE TO RELATED APPLICATIONS

This application is a 371 National Phase of PCT/US2008/071802, filed on Jul. 31, 2008, which claims priority to and benefit of U.S. Ser. No. 60/953,159, filed on Jul. 31, 2007, both of which are incorporated herein by reference in their entirety for all purposes.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention pertains to the field of immunology. In particular compositions are provided that are capable of inducing an immune response in a mammal directed against a protozoan parasite.

BACKGROUND OF THE INVENTION

Protozoan parasites are the causal agents in a number of diseases that humans, farm animals, and pets. For example, *Leishmania* organisms are intracellular protozoan parasites of macrophages that cause a wide range of clinical diseases in humans and domestic animals, primarily dogs. In some infections, the parasite may lie dormant for many years. In other cases, the host may develop one of a variety of forms of leishmaniasis. For example, the disease may be asymptomatic or may be manifested as subclinical visceral leishmaniasis, which is characterized by mild symptoms of malaise, diarrhea and intermittent hepatomegaly. Patients with subclinical or asymptomatic disease usually have low antibody titers, making the disease difficult to detect with standard techniques. Alternatively, leishmaniasis may be manifested as a cutaneous disease, which is a severe medical problem but is generally self-limiting, or as a highly destructive mucosal disease, which is not self-limiting. Finally, and most seriously, the disease may be manifested as an acute visceral infection involving the spleen, liver and lymph nodes, which, untreated, is generally a fatal disease. Symptoms of acute visceral leishmaniasis include hepatosplenomegaly, fever, leukopenia, anemia and hypergammaglobulinemia.

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis. There are, however, no vaccines or effective treatments currently available.

Accurate diagnosis of leishmaniasis is frequently difficult to achieve. There are 20 species of *Leishmania* that infect humans, including *L. donovani, L. chagasi, L. infantum, L. major, L. amazonensis, L. braziliensis, L. panamensis, L. mexicana, L. tropica*, and *L. guyanensis*, and there are no distinctive signs or symptoms that unambiguously indicate the presence of *Leishmania* infection. Parasite detection methods have been used, but such methods are neither sensitive nor clinically practical. Current skin tests typically use whole or lysed parasites. Such tests are generally insensitive, irreproducible and prone to cross-reaction with a variety of other diseases. In addition, the preparations employed in such tests are often unstable.

SUMMARY OF THE INVENTION

This invention provides novel compositions that, when administered to mammals, or non-mammalian vertebrates, induce an immune response against a protozoan parasite. In certain embodiments the compositions are effective to inhibit infectivity, and/or pathology, and/or proliferation of the parasitic protozoan.

Thus, in certain embodiments this invention provides a composition for inducing an immune response in a vertebrate host against a protozoan parasite. The composition typically comprises a protozoan parasite comprising a psoralen-modified DNA, whereby the protozoan parasite is killed but metabolically active (KBMA); and when administered to a vertebrate is effective to induce an immune response in said vertebrate where said immune response is directed against the protozoan parasite. In various embodiments the protozoan parasite comprises a DNA modified with a psoralen selected from the group consisting of psoralen, isopsoralen, TMP, HMT, 8-MOP, AMT, and S-59. In certain embodiments the composition further comprises an adjuvant (e.g., a toll-like receptor agonist). In certain embodiments the adjuvant comprises an agonist for TLR-7 and/or TLR-8. In various embodiments the toll-like receptor agonist comprises an imidazoquinolinamine. In certain embodiments the toll-like receptor agonist comprises a nucleoside analogue. In certain embodiments the toll-like receptor agonist comprises one or more agents selected from the group consisting of imiquimod, resiquimod (R-848), 3M-001, 3M-002, flagellin, poly U, Loxoribine, and CPG-A DNA, CpG-C DNA, 7-thia-8-oxoguanosinyl, 7-deazaguanosinyl, and abrogate. In certain embodiments the protozoan parasite belongs to the phylum Apicomplexa. In certain embodiments the protozoan parasite belongs to a genus selected from the group consisting of *Plasmodium, Toxoplasma, Neospora, Eimeria, Theileria, Babesia, Cryptosporidium, Sarcocystis*, and *Leucocytozoon*. In certain embodiments the protozoan parasite belongs to the phylum Kinetoplastida. In certain embodiments the protozoan parasite belongs to a genus selected from the group consisting of *Leishmania* and *Trypansoma*. In certain embodiments the composition is formulated for administration by a method selected from the group consisting of topical administration, subcutaneous administration, intramuscular administration, intravenous administration, transdermal administration, inhalation administration, and oral administration. In certain embodiments the composition is formulated for administration to a vertebrate selected from the group consisting of bird, canine, equine, feline, porcine, bovine, human, and non-human primate.

Also provided are methods for inducing an immune response in a vertebrate host against a protozoan parasite. The methods typically involve administering to the host a protozoan parasite comprising a psoralen-modified DNA, whereby the administration produces an immune response in the host directed against the protozoan parasite. In certain embodiments the protozoan parasite comprises a DNA modified with a psoralen selected from the group consisting of psoralen, isopsoralen, TMP, HMT, 8-MOP, AMT, and S-59. In certain embodiments the administering further comprises administering to the host an adjuvant. In certain embodiments the adjuvant comprises a toll-like receptor agonist. In certain embodiments the toll-like receptor agonist is administered before the protozoan parasite. In certain embodiments the toll-like receptor agonist is administered after the protozoan parasite. In certain embodiments the toll-like receptor agonist is administered at the same time as the protozoan parasite. In certain embodiments the toll-like receptor agonist and the protozoan parasite are administered as a single composition. In certain embodiments the toll-like receptor agonist comprises an agonist for TLR-7 and/or TLR-8. In certain embodiments the toll-like receptor agonist comprises an imidazoquinolinamine. In certain embodiments the toll-like receptor agonist comprises a nucleoside analogue. In certain embodiments the toll-like receptor agonist comprises one or more agents selected from the group consisting of imiquimod, resiquimod (R-848), 3M-001, 3M-002, flagellin, poly U, Loxoribine, and CPG-A DNA, CpG-C DNA, 7-thia-8-oxoguanosinyl, 7-deazaguanosinyl, and abrogate. In various embodiments the administering is by a method selected from the group consisting of topical administration, subcutaneous administration, intramuscular administration, intravenous administration, transdermal administration, inhalation administration, and oral administration. In certain embodiments the protozoan parasite belongs to the phylum Apicomplexa. In certain embodiments the protozoan parasite belongs to the genus *Plasmodium, Toxoplasma, Neospora, Eimeria, Theileria, Babesia, Cryptosporidium, Sarcocystis*, or *Leucocytozoon*. In certain embodiments the protozoan parasite belongs to the phylum Kinetoplastida. In certain embodiments the protozoan parasite belongs to the genus *Leishmania* or *Trypansoma*. In various embodiments the vertebrate host is a mammal (e.g., canine, equine, feline, porcine, bovine, non-human primate, or human) or a bird (e.g., chicken, pheasant, duck, goose, etc.).

Also provided are methods of preparing a composition that induces an immune response in a vertebrate host against a protozoan parasite. The methods typically involve contacting a protozoan parasite with a psoralen and exposing the psoralen and protozoan to ultraviolet A radiation, whereby the protozoan becomes a killed but metabolically active protozoan (KBMA). In various embodiments the psoralen is selected from the group consisting of psoralen, isopsoralen, TMP, HMT, 8-MOP, AMT, and S-59. In certain embodiments the method further comprises combining the KBMA protozoan with an adjuvant (e.g., a toll-like receptor agonist). In various embodiments the adjuvant comprises an agonist for TLR-7 and/or TLR-8. In certain embodiments the toll-like receptor agonist comprises an imidazoquinolinamine. In certain embodiments the toll-like receptor agonist comprises a nucleoside analogue. In certain embodiments the toll-like receptor agonist comprises one or more agents selected from the group consisting of imiquimod, resiquimod (R-848), 3M-001, 3M-002, flagellin, poly U, Loxoribine, and CPG-A DNA, CpG-C DNA, 7-thia-8-oxoguanosinyl, 7-deazaguanosinyl, and abrogate. The protozoan parasite can include any one or more of the protozoan parasites described herein.

In various embodiments, kits are provided for inducing an immune response in a vertebrate host against a protozoan parasite. The kits typically comprise one or more immunogenic compositions as described herein (e.g., a KBMA protozoan and/or a TLR agonist) and a means for administering the composition to a bird or mammal.

Methods are also provided for inducing an immune response that is partially or fully protective against protozoan infection or pathology in a mammal. The methods typically involve administering to the mammal a toll-like receptor agonist in an amount sufficient to induce an immune response. In certain embodiments the toll-like receptor agonist is an agonist for TLR-8 and/or TLR-8. In certain embodiments the toll-like receptor agonist is administered topically or subcutaneously to the mammal. In certain embodiments the toll-like receptor agonist is imiquimod, and/or resiquimod.

Methods are provided for inducing an immune response that is partially or fully protective against protozoan infection or pathology in a mammal, where the methods involve administering to the mammal a heat-killed protozoan in conjunction with a toll-like receptor agonist in an amount sufficient to induce an immune response, where the TLR agonist is not a CpG. In various embodiments the toll-like receptor agonist is administered topically or subcutaneously. In certain embodiments the toll-like receptor agonist is selected from the group consisting of imiquimod, and resiquimod.

In certain embodiments this invention expressly excludes KBMA bacteria, and/or KBMA viruses, and/or KBMA fungi. In certain embodiments this invention expressly excludes KBMA and/or KBMA *Plasmodium*.

In certain embodiments, where heat-killed protozoa are used, the methods and/or compositions of the invention exclude CpG as a toll-like receptor agonist.

DEFINITIONS

Protozoal disease refers to diseases which are caused by infections with various pathogenic parasitic protozoa spread to humans or other animals. Known typical protozoal diseases are diseases due to infections, such as amebiasis, trypanosomiasis, malaria, toxoplasmosis, pneumocystosis, cryptosporidiosis, giardiasis, and leishmaniasis. The protozoal diseases, which are given particular attention as a target for the therapy of the present invention, are diseases accompanied by anemia, such as trypanosomiasis, malaria, babesiosis, and leishmaniasis. The present invention is effective, particularly, for the treatment of trypanosomatids. Protozoa, as used herein do not include bacteria or viruses.

A "killed but metabolically active (KBMA)" organism is an organism that is replication deficient, but still metabolically active for some time (e.g., at least 3 days, preferably at least 1 week, more preferably at least two weeks, and most preferably at least three or four weeks. In certain embodiments the KBMA organism is metabolically active from about 3, 4, 5, 6, or 7 days to about 3, 4, 5, 6, 7, or 8 weeks.

The "coadministration" or "administration in conjunction with" when used with respect to an immunogenic agent (e.g., a KBMA protozoan) and an adjuvant (e.g., a TLR agonist) as described herein indicates that KBMA protozoan (or other immunogenic agent) and the TLR agonist (and/or other adjuvant) are administered so that there is at least some chronological overlap in the activity of the immunogenic agent and the adjuvant such that the adjuvant enhances in vivo activity of the immunogenic agent. In sequential administration there may even be some substantial delay (e.g., minutes or even hours) between administration of the adjuvant and the immunogenic agent as long as the adjuvant is present in such that a manner that its bioactivity is present while the bioactivity of the immunogenic agent is also present.

BRIEF DESCRIPTION OF THE DRAWINGS

FIG. 6A: Metabolic activity of *Leishmania chagasi* treated with indicated doses of amotosalen (S-59) and UVA irradiation. Organisms genetically modified to express firefly luciferase were inoculated into culture at $10^7$ per ml. The Figure shows luminescence from organisms taken at time points after addition of S-59 with or without UVA irradiation. As compared to untreated or unirradiated organisms, by day 21, luciferase activity from organisms treated with 100 nm S-59 and UVA approaches baseline luminescence from PBS. 6B: Live and KBMA, but not heat-killed LC demonstrate widespread invasion of bone marrow derived macrophages in vitro. Photographs of Giemsa stained cells. Arrows indicate amastigote infected macrophages. FIG. 6C: Nitric-oxide (NO) production in bone marrow derived macrophages from BALB/c mice. Macrophages were cultured in media supplemented with 10 units/ml interferon-γ. The Figure shows percent increase in nitric oxide production over uninfected macrophages. KBMA organisms demonstrate increased NO production compared with heat-killed ($p<0.05$). Difference between Live and KBMA were not statistically significant. Means of three independent experiments with SEM.

DETAILED DESCRIPTION

Figure 1:
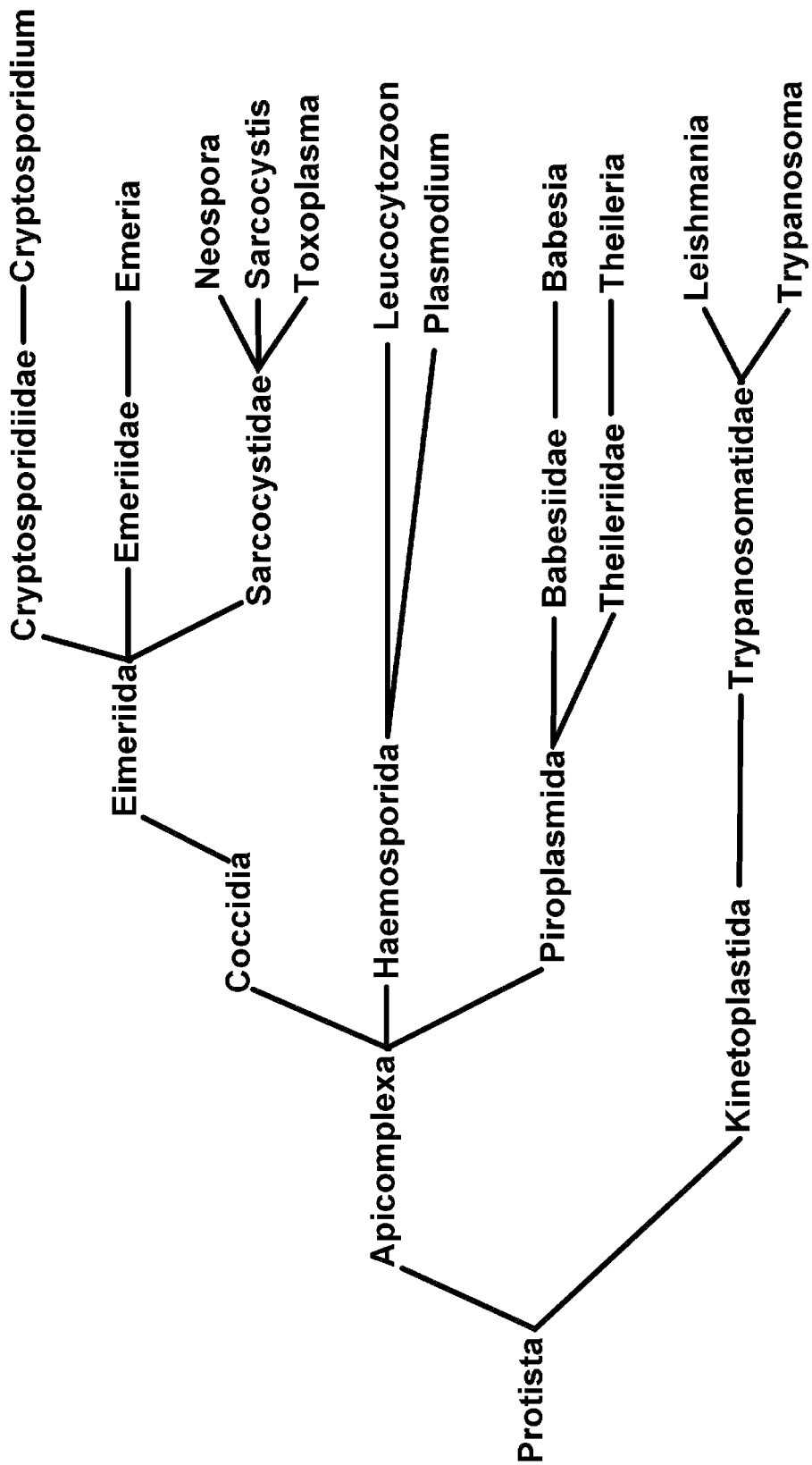
FIG. 1 shows a categorization of the phyla Apicomplexa and Kinetoplastida in the kingdom Protista.
Figure 2:
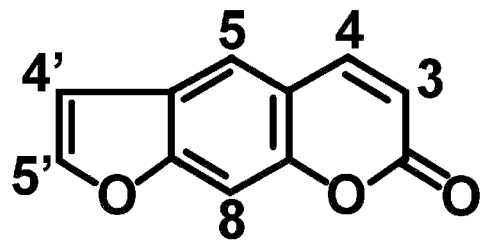
FIG. 2 shows the structure and numbering system used for psoralen, isopsoralen (angelicin), methoxypsoralen (8-MOP), 4,5',8-trimethylpsoralen (TMP), 4'-hydroxymethyl-4,5',8-trimethylpsoralen (HMT) and 4' aminomethyl-4, 5~,8-trimethylpsoralen (AMT).
Figure 2:
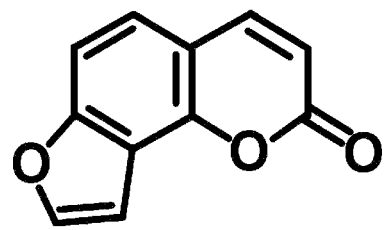
Figure 2:
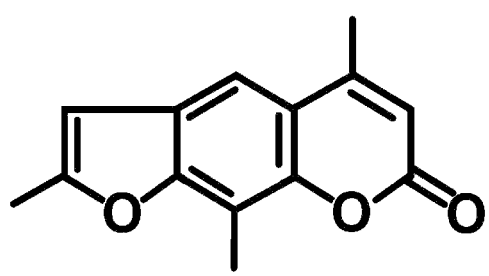
Figure 2:
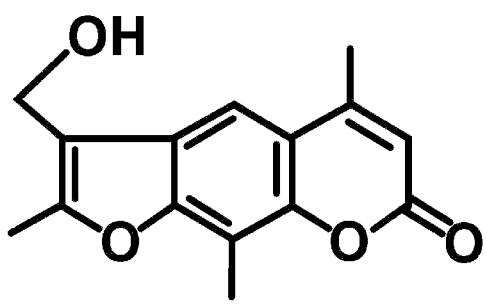
Figure 2:
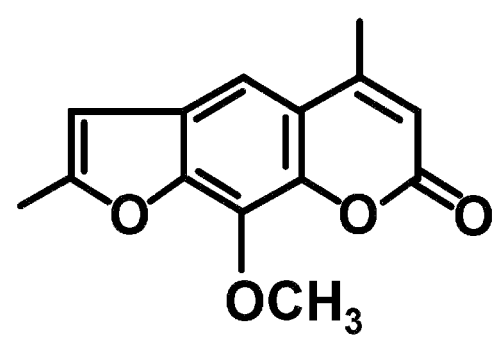
Figure 2:
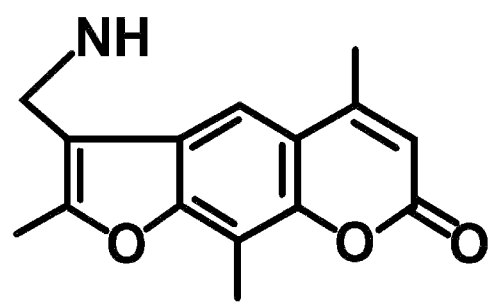

In various embodiments this invention provides novel agents that, when administered to a mammal, induce an immune response directed against one or more protozoan parasites. Protozoan parasites are causal agents in a number of diseases that afflict humans, and/or non-human mammals (e.g., farm animals, pets, etc.). In certain embodiments, the agents described herein are effective to promote an immune response in non-mammalian vertebrates (e.g., fish, birds, etc.).

In various embodiments the immunogenic agents of this invention comprise one or more killed, but metabolically active (KBMA) protozoans alone, or in combination with one or more adjuvants. The KBMA protozoa are effective to induce an immune response in a host directed against the subject protozoan genus, species, or subspecies. In various embodiments the immune response is effective to reduce or prevent infectivity and/or to reduce or prevent pathogenesis by the protozoan, and/or to reduce or prevent transmission of the protozoan.

Typically, the immunogenic agent(s) (e.g., KBMA Leishmania) described herein will be administered to a subject at risk for the infection or already infected. The subject can be a human, a non-human mammal (e.g., bovine, equine, canine, feline, porcine, etc.) or a non-mammalian vertebrate (e.g., chicken, bird, duck, goose, fish, etc.).

In various embodiments the immunogenic agent(s) are administered alone or in combination with one or more adjuvants to the host as a prophylactic and/or therapeutic formulation on one or more occasions, e.g., at sufficient dosage and/or frequency to induce an immune response directed against the protozoan organism.

Thus, in certain embodiments the agents comprise an immunogen that is a killed, but metabolically active (KBMA) protozoan. Without being bound to a particular theory, it is believed that the KBMA protozoan functions like a natural infection to induce an immune response. It was a surprising discovery that KBMA protozoa were effective immunogens even when the native protozoan spends a portion of its lifecycle as an intracellular parasite. It was also discovered that the danger of virulent infection (e.g. by *Leishmania* or other protozoan parasites) can be reduced to near zero by using KBMA technology.

In certain embodiments the KBMA protozoa (immunogenic agents) are administered in conjunction with one or more toll-like receptor agonist(s) (TLR agonists). The TLR agonists can act as an effective adjuvant increasing the immune response directed against the protozoan parasite(s). Without being bound by a particular theory, it is believed the combination of the KBMA protozoan and the TLR agonist(s) likely causes a Th1 type immune response that is capable of destroying the parasites during vaccination and leading to better presentation to the adaptive arm of the immune response and long lasting protection.

It was also a surprising discovery that toll-like receptor agonists (e.g., TLR-agonists) can offer protection against infection and/or pathogenicity of *Leishmania*. It is also believed that similar protection can be obtained against other protozoan parasites. In certain embodiments, the toll-like receptor agonist (e.g., a TLR-7 and/or TLR-8 ligand) is administered topically or systemically, to a subject in need thereof, e.g., a subject at risk for infection and/or pathology. It is also contemplated that the TLR agonists can be administered to subjects already infected.

It is believed that administration of the TLR receptor agonist(s) to a subject before challenge, e.g., with one or more of the immunogenic agents described herein, or by a natural infection, leads to protective immunity.

While the immunogenic agents described herein focus on KBMA protozoans, it is contemplated that in certain embodiments other KBMA pathogens can act as effective immunogenic agents, particularly where the pathogen spends a portion of its life cycle as an intracellular "parasite". Thus, in certain embodiments, the use of KBMA bacteria (e.g., KBMA tuberculosis), KBMA viruses, and KBMA fungi are also contemplated.

It is also noted that, in certain embodiments, toll-like receptor agonists (e.g., a TLR-7 and/or TLR-8 ligand) can be used in conjunction with heat-killed and/or radiation-killed protozoa, bacteria, viruses, fungi, and the like to generate effective reagents that induce an immune response directed against the pathogen.

Protozoan Parasites

In certain embodiments this invention contemplates the use of killed but metabolically active protozoan parasites, alone or in combination with one or more adjuvants" to induce an immune response in a mammal or a non-mammalian vertebrate against that protozoan. In certain embodiments the immune response is sufficient to increase resistance to infection and/or pathogenicity by that protozoan or to actually prevent infection and/or pathogenicity.

The term "protozoan parasite" generally refers to any protozoan organism that is eukaryotic, unicellular, parasitic, and characterized by multiple infective stages within its vertebrate host. Illustrative parasitic protozoan organisms as described herein typically belong to the phylum Apicomplexa or the phylum Kinetoplastida. A taxonomic outline of the kingdom Protista including the phylum Apicomplexa and the phylum Kinetoplastida is shown in FIG. 1. Reclassification within the phylum Apicomplexa is quite common, as defining characteristics and new species are uncovered. In many instances, a grouping within the phylum does not have an official rank, such as the Piroplasmida. Sometimes, ranking is incomplete within the phylum. Some groupings lack a designated Class, while others have no assigned Order or Family classification (see, NCBI Taxonomy Browser, http://www.ncbi.nlm.nih.gov/Taxonomy/Browser). Apicomplexan parasites used in the methods of the invention include, but are not limited to, protozoan parasites that are members of the genera *Plasmodium, Toxoplasma, Neospora, Eimeria, Theileria, Sarcocystis,* and *Cryptosporidium*.

The phylum Kinetoplastida includes a particularly virulent family of parasitic protozoa, the Trypanosomatidae. This family includes the protozoan parasites *Trypanosoma* and *Leishmania*, which cause significant and serious disease throughout the world). The various species and subspecies of *Trypanosoma brucei, Trypanosoma cruzi,* and *Leishmania* cause staggering losses in human life and productivity in regions of endemicity. Kinetoplastida parasites used in the methods of the invention include, but are not limited to, protozoan parasites of the genera *Trypanosoma* and *Leishmania*.

*Leishmania* and malaria are perhaps the best known protozoan diseases. Malaria, is a leading cause of death accounting for more than 2 million deaths per year. It is estimated that 35% of world's population is infected by Malaria. Malaria is caused by different species of *Plasmodium* (e.g., *P. vivax, P. falciparum, P. ovale*).

Leishmaniasis is a worldwide disease and is endemic in at least 88 countries. Human infections are found in 16 countries in Europe, including France, Italy, Greece, Malta, Spain and Portugal, as well as throughout Asia, Northern Africa, central and South America. Many mammals are potential host reservoirs, including rodents, foxes, jackals, but perhaps the most significant is the dog. Close human interactions with domesticated dogs are believed to be a significant source of human infection (Vanloubbeeck and Jones (2004) *Ann. N.Y Acad. Sci.* 1026:267-272). The parasite is generally transmitted by the bite of a sandfly, and the vector is difficult to control. Leishmaniaisis is of particular concern to travelers and military personnel stationed in endemic regions. There are many species and subspecies of *Leishmania* that cause disease, some of the most significant include *L. major, L. infantum, L. donovani, L. mexicana, L. braziliensis, L. chagasi*, and *L. amazonensis*.

*Leishmania* are highly adaptive and have several life stages. Within the insect, amastigotes transform in to the promastigote form. The promastigotes then migrate to the midgut of the fly, where they live extracellularly and multiply by binary fission. Promastigotes then move forward to the oesophagus and the salivary glands of the insect. When the sandfly next feeds on a mammalian host, the *Leishmania* promastigotes are transferred to the host. Once in the host, the promastigotes are taken up by the macrophages where they revert to the amastigote form. Amastigotes multiply inside the macrophages, eventually leading to the lysis of the macrophages. (Vanloubbeeck and Jones (2004) *Ann. N.Y. Acad. Sci.* 1026: 267-272). The released amastigotes are taken up by additional macrophages and so the cycle continues. Ultimately all the organs containing macrophages and phagocytes are infected, especially the spleen, liver and bone marrow.

Those infected may present a range of symptoms, as there are several forms of the disease, with varying ranges of severity. The most serious, and often fatal if untreated is visceral leishmaniasis (kala azar), with symptoms including fever, malaise, weight loss, anemia, swelling of the spleen, liver and lymph nodes. The most common manifestation is cutaneous leishmaniasis, resulting in multiple skin lesions and scarring. Mucocutaneous leishmaniasis, begins with skin ulcers which spread, and cause massive tissue destruction, especially of the nose and mouth and leaves victims horribly disfigured (Vanloubbeeck and Jones (2004) supra.).

Often overshadowed by *Plasmodium* and *Leishmania*, other organisms within the phylum Apicomplexa, as well as protozoan organisms within the phylum Kinetoplastida, cause significant diseases in humans and animals. For example, protozoan organisms within the genuses of *Toxoplasma, Neospora, Eimeria, Theileria, Babesia, Cryptosporidium, Sarcocystis, Leucocytozoon, Leishmania*, and *Trypansoma* all devastate susceptible vertebrate host populations and severely impact economic development in endemic regions. In general, these protozoan organisms are eukaryotic, unicellular, parasites that have a life cycle including at least two infective stages in a susceptible vertebrate host, one of which cause the secondary infection that is the hallmark of the protozoan disease.

The family Sarcocystidae includes several pathogenic parasites, including *Toxoplasma. Toxoplasma gondii* is the only identified species (NCBI Taxonomy Browser, http://www.ncbi.nlm.nih.gov/Taxonomy/Brower). Toxoplasmosis is a widespread illness, with very low host specificity-meaning the parasite can replicate within virtually any nucleated mammalian or avian cell (Charleston (1994) *N. Zealand J. Zool.* 21: 67-81; Black and Boothroyd (2000) *Microbiol. Mol. Biol. Rev.* 64(3): 607-623). While disease severity can range from mild to life threatening, those most at risk for serious illness and side effects are the immune compromised and developing fetuses (Innes (1997) *Comp. Immun. Microb. Infect. Dis.* 20(2):131-138). Miscarriage, stillbirth, and severe congenital defects are a tragic result of maternal toxoplasmosis during pregnancy. Toxoplasmosis is also a leading cause of abortion in sheep, pigs, and goats, resulting in significant economic loss annually.

*Neospora* are biologically very similar to *Toxoplasma*, but cause a distinctively different disease. Like *toxoplasma, neospora* is widespread, and is capable of infecting many different types of warm-blooded mammalian cells (Dubey (2003) *Korean J. Parasitol.* 41(1):1-16). Infection with acute or chronic *Neospora* is a major cause of abortion in cattle, paralysis in dogs, and to a lesser extent abortion in sheep and goats. Young animals infected with *Neospora* will exhibit neurological symptoms such as ataxia and paralysis (Beckers (1997) *Mol. Biochem. Parasitol.* 89(2): 209-q23). The sexual cycle of *Neospora* occurs within dogs, and can cause a range of symptoms, especially in young pups (Buxton et al. (2002) *Trends Parasitol.* 18(12): 546-52). While methods of transmission of *Neospora* are not as well studied as *Toxoplasma* (Hall et al. (2005) *Vet. Parasitol.* 128(3-4): 231-241), transplacental transmission has been confirmed, and ingestion of fetal material (aborted fetus, placenta) and milk from seropositive cows, or ingestion of carcasses infected with bradyzoites also lead to infection. Ingestion of oocysts shed in dog feces is another route of transmission (Dubey (2003) *Korean J. Parasitol.* 41(1): 1-16; Hall et al. (2005) *Vet. Parasitol.* 128(3-4): 231-241). Following ingestion of oocysts, tachyzoites rapidly invade host cells, and eventually develop into slower growing bradyzoites that encyst within tissue. Both tachyzoites and bradyzoites are found in the central nervous system and muscle of infected animals.

Many species of Eimeria parasites are found within the family Eimeriidae, and cause widespread disease throughout the world. Eimeria parasites are highly species specific and affect cattle, goats and sheep. Infection is most significant in avian populations, causing severe diarrhea, weight loss and ceccal lesions, often resulting in death (Augustine (2001) *Trends Parasitol.* 17(11):509-511; Allen and Fetterer (2002) *Clin. Microbiol. Rev.* 15(1):58-65). Infection with Eimeria, often referred to as coccidiosis, is a major cash burden in the poultry industry. Costs associated with poultry loss, lack of productivity and drug treatment are estimated to be well over $800 million annually (Augustine et al. (2001) *Trends Parasitol.* 17(11):509-511; Allen and Fetterer (2002) *Clin. Microbiol. Rev.* 15(1):58-65).

*Theileria* is grouped with *Babesia* as a Piroplasmida. Theileriosis is a significant disease of cattle, sheep and goats in tropical and sub-tropical countries. Disease is commonly found from North Africa and southern Europe in the West, to India and China in the East (Burkot and Graves (2004) *Medical Entomology* (Eldridge & Edman, eds.), Kluwer Academic Publishers, pp. 187-230; Nagore et al. (2004) *Intl. J. Parasi-* tol. 34:1059-1067). The introduction and cross-breeding of naive species of Western cattle, in particular Friesen, to improve cattle productivity has actually increased cattle morbidity due to theileriosis. Disease symptoms include anemia, leukopenia, cachexia, mucous membrane discharge, and dysentery. Susceptible animals often die within 15-25 days of acute infection if not treated (Criado-Formelio et al. (2003) *Vet. Parasitol.* 113:189-201).

*Babesia*, along with *Theileria*, is grouped as a Piroplasmida. Unlike *Theileria, Babesia* does not have a pre-erythrocytic host cell, however there is some debate regarding *Babesia equi* first invading lymphocytes prior to erythrocytes (some groups have reclassified *B. equi* as *Theileria equi*, due to host cell specificity) (Gray et al. (2002) *Intl. J. Med. Microbiol. Suppl.* 33:108-111; Burkot and Graves (2004) *Medical Entomology* (Eldridge & Edman, eds.), Kluwer Academic Publishers, pp. 187-230). *Babesia* species are capable of infecting cattle, horses, dogs, pigs, and humans. Babesiosis occurs worldwide, but is most prevalent in the North Eastern United States and Europe through North Africa. While disease is rare in healthy humans, infection with *B. divergens* carries a mortality rate of 42%. Veterinary babesiosis is much more prevalent and incurs huge economic costs annually (Gray et al. (2002) Intl. J. Med. Microbiol. Suppl. 33:108-111; Zintl et al. (2003) Clin. Microbiol. Rev. 16(4):622-36; Burkot & Graves (2004) Medical Entomology (Eldridge and Edman, eds.), Kluwer Academic Publishers, pp. 187-230; Nagore et al. (2004) *Intl. J. Parasitol.* 34:1059-1067). Peaks in parasitemia and disease incidence occur twice annually, once in the Spring and once in the Fall, illustrating the need for long lasting immunity.

*Cryptosporidium parvum* and *Cryptosporidium hominis* cause prolonged diarrheal disease in immunocompromised humans and livestock, and is particularly problematic in young calves. Ingestion of oocysts from contaminated water is the most common route of transmission, so immunization of animals is a possible method of preventing downstream human infection as well. Sporozoites are released from oocysts and rapidly infect intestinal epithelial cells.

*Sarcocystis cruzi* and *neuroni* cause bovine, ovine, equine and porcine encephalopathy worldwide.

Leukocytozoon cause disease in domesticated poultry, and are most problematic in Asian countries. Infection causes weight loss, poor egg production and death in chickens, ducks and turkeys. Currently, animals are treated with drugs, but residuals found in meat and eggs demonstrate the necessity for vaccine candidates. Killed as well as live sporozoite vaccine attempts are documented in literature, but these are not very effective.

African Trypanosomiasis (AT), is a neurological disease caused by infection with *Trypanosoma brucei* (Sternberg (2004) Parasite Immunol. 26(11-12): 469-476). Currently, over 60 million people in 36 different countries are susceptible to the potentially chronic and often fatal disease. Annually, it is believed over 500,000 are infected with *Trypanosoma brucei* subspecies (WHO (2001) African Trypanosomiasis Fact Sheet). *Trypanosoma brucei rhodesiense* is prevalent in the East African savannah plains, and often causes an acute and virulent disease. The West African bush is home to the *T. brucei* subspecies *gambiense*, which causes a chronic illness (Leder et al. (2001) UpToDate 2203). Humans remain refractory to *Trypanosoma brucei brucei*, however cattle and sheep are ravaged by infection with the parasite, in a condition referred to as nagana (WHO (2001) African Trypanosomiasis Fact Sheet). The loss of human life and the collapse of worker productivity and cattle crops due to African trypanosomiasis is devastating to endemic regions.

The chronic and devastating disease caused by *Trypanosoma cruzi* was first characterized in the early 1900s by Carlos Chagas (Barret et al. (2003) Lancet 362(9394): 1469-1480). In endemic regions ranging from Northern Mexico and south through Argentina, it is estimated that 16-18 million people are infected with the parasite. Conservative estimates predict that another 11-40 million people are at risk of infection (WHO (2004) Chagas Disease). The disease is particularly virulent in young children, and is often fatal. However in adults the course of illness has little to no symptoms for months to years. During this symptomless phase, parasites are invading and weakening host organs, including heart, intestines, esophagus. Fatality is often a result of cardiomyopathy, and upon autopsy, most victims of Chagas disease presented enlargement of several organs, including the spleen, heart, colon and esophagus. Parasites can also be transmitted through blood transfusions (Pomper et al. (2003) *Curr. Opin. Hematol.* 10(6):412-418), and congenitally from mother to fetus.

The foregoing are illustrative pathogenic protozoa and are not intended to be limiting. Numerous other pathogenic protozoans are know to those of skill in the art and various protozoan species are known to infect virtually every mammalian tissue (see, e.g., Table 1.

TABLE 1

Illustrative tissues infected by pathogenic protozoa.

| | |
|---|---|
| Skin | Leishmania |
| Eye | Acanthamoeba |
| Mouth | Amoebae and flagellates (usually non-pathogenic) |
| Gut | Giardia, Entamoeba (and invasion to liver), Cryptosporidium, Isospora, Balantidium |
| G.U. tract | Trichomonas |
| Bloodstream | Plasmodium, Trypanosoma |
| Spleen | Leishmania |
| Liver | Leishmania, Entamoeba |
| Muscle | Trypanosoma cruzi |
| CNS | Trypanosoma, Naegleria, Toxoplasma, Plasmodium |

In various embodiments this invention contemplates agents comprising one or more of the protozoan parasites described herein, or other protozoan parasites, treated so that they are killed but metabolically active (KBMA). The agents can be administered to human or non-human mammals susceptible to infection and/or to non-mammalian vertebrates (e.g., birds, fish, etc.) also susceptible to such infection to mitigate or eliminate infectivity and/or pathogenicity and/or proliferation of the parasite.

The protozoans described above are illustrative and not limiting. Using the teaching provided herein, one of skill can apply the methods of the present invention to produce compositions that induce an immune response directed against other protozoans.

Producing KBMA Protozoans

It was a surprising discovery that protozoans that are rendered replication incompetent, but metabolically viable for some time period (KBMA) protozoans are agents highly effective in raising an immune response directed against the subject genus or species. Methods of rendering organisms killed, but metabolically active are know to those of skill in the art. Such methods include, but are not limited to, the use of low level irradiation, photochemical treatment of DNA excision repair mutants, introduction of mutations, and chemical modification of DNA.

In certain embodiments protozoa are converted to KBMA organisms by treatment with low (e.g., nanomolar) dosages of one or more psoralens in combination with ultraviolet (e.g., UVA) radiation. Without being bound by a particular theory, it is believe the psoralens combined with the radiation cross-link the DNA of the organism rendering the organism replication deficient (e.g., substantially or completely unable to reproduce). It was discovered that killed but metabolically active protozoa retain broad antigenicity and pathogen behavior such as host cell invasion but are ultimately avirulent because they cannot replicate.

Psoralens are a class of photo-mutagenic and photo-chemotherapeutic molecules that covalently modify nucleic acids. They belong a family of small molecules that intercalate into and photoalkylate double stranded DNA. The primary target of psoralens are thymidine residues, and these molecules form both monoadducts and interstrand crosslinks. The reaction typically takes place between the 3,4 (pyrone) or 4',5' (furan) double bonds of the psoralen and the 5,6 double bond in pyrimidines.

Figure 3:
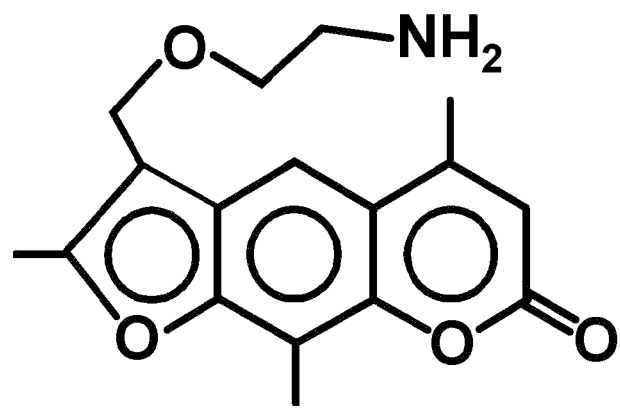
FIG. 3 illustrates the structure of psoralen S-59 (Amotosalen).

In certain embodiments the psoralen S-59 is used to produce the KBMA protozoa. The structure of psoralen S-59 (also known as Amotosalen) is shown in FIG. 3. The compositions and methods of the present invention, however, are not limited to the use or incorporation of psoralen S-59. Other psoralens are also known to those of skill in the art and are also commercially available. Such psoralens include, but are not limited to HMT (4'-hydroxymethyl-4,5',8-trimethylpsoralen), 8-methoxy psoralen (8-MOP), 4,5',8-trimethylpsoralen, 5-bromo-8 {3-[(4-methoxycarbonyl)pyridinio]propyloxy}psoralen bromide and other halogenated psoralen compounds such as those described in U.S. Pat. No. 5,919,935, which is incorporated herein by reference, 8-methoxypsoralen, and the like.

The optimal psoralen and uv radiation dosage to produce a KBMA protozoan can readily be determined. Where the lethal dosage is known, e.g., the amount proven immediately lethal in the blood product decontamination setting a range of doses is provided below this limit. Where the lethal dosage is not know, a broader range of doses can be provided. Protozoan quantitation and cell viability can be determined after treatment. Metabolic activity is assayed by any convenient marker. For example, a reporter gene introduced into the organism (e.g., a luciferase gene) and assayed after treatment. In addition, or alternatively, expression of any of a number of endogenous genes can readily be determined.

Optimal psoralen/UV doses yield organisms that are viable, metabolically active and immunogenic in the early vaccination period (typically 1-3 weeks) but are substantially or completely unable to proliferate. Because this technology represents a novel methodology in protozoa, during this process we will also characterize the mechanism of cell death in the parasites using well described methods using intracellular and cell surface markers.

While the foregoing discussion pertains to psoralen-modified protozoa, similar methods can be applied to produce psoralen modified (KBMA) bacteria, viruses, and fungi.
Toll-Like Receptor (TLR) Ligand/Agonist.

In various embodiments, the immunogenic agents described herein are administered in conjunction with a toll-like receptor agonist (TLR agonist). In certain embodiments the toll-like receptor agonist is an agonist for toll-like receptor 7 (TLR-7) and/or toll-like receptor 8 (TLR-8). It was also discovered that toll-like receptor agonists alone can confer partial or full protective immunity against protozoan parasites.

A TLR agonist is any compound or substance that functions to activate a TLR, e.g., to induce a signaling event mediated by a TLR signal transduction pathway. Suitable TLR agonists include TLR-2 agonists, and/or TLR-3 agonists, and/or TLR-4 agonists, and/or TLR-7 agonists, and/or TLR-8 agonists, and/or TLR-9 agonists.

Some examples of TLR ligands include, but are not limited to, lipoproteins; peptidoglycan, zymosan (TLR-2), double-stranded RNA, polyI:polyc (TLR-3), lipopolysaccharide, heat shock proteins, taxol (TLR-4), flagellin (TLR-5), and imidazoquinolines-R848, resiquimod, imiquimod; ssRNA (TLR-7/8), and the like.

Suitable TLR agonists include isolated, naturally-occurring TLR agonists; and synthetic TLR agonists. TLR agonists isolated from a naturally-occurring source of TLR agonist are generally purified, e.g., in various embodiments, the purified TLR agonist is at least about 80% pure, at least about 90% pure, at least about 95% pure, at least about 98% pure, at least about 99% pure, or more than 99% pure. Synthetic TLR agonists are prepared by standard means, and, in various embodiments, are generally at least about 80% pure, at least about 90% pure, at least about 95% pure, at least about 98% pure, at least about 99% pure, or more than 99% pure.

Suitable TLR agonists include TLR agonists that are not attached to any other compound. Suitable TLR agonists also include TLR agonists that are attached, covalently or non-covalently, to a second compound. In some embodiments, a TLR agonist is attached to another compound directly. In other embodiments, a TLR agonist is attached to another compound through a linker. The compound to which a TLR agonist is attached can include a carrier, a scaffold, an insoluble support, a microparticle, a microsphere, a KBMA protozoan, therapeutic polypeptides, agents that improve solubility, agent that increase the half-life of the TLR agonist in a physiological medium (e.g., serum or other bodily fluid); and the like.

In some embodiments, the TLR agonist is a selective TLR agonist. In some embodiments, a TLR-selective compound mediates cellular activity (e.g., induces production of IFN-α and/or IFN-β through one or more TLRs. In such cases, "TLR selective" may refer to selectivity between two or more TLRs of particular interest, e.g., TLR-7 and TLR-8. Thus, e.g., "TLR-8-selective" may refer, in some embodiments, to a compound that modulates TLR-8-mediated cellular activity, but does not modulate (i.e., does not substantially increase or decrease) cellular activity mediated through any other TLR (i.e., TLR-8 only). In other embodiments, however, "TLR-8-selective" may refer to a compound that modulates TLR-8-mediated cellular activity and cellular activity modulated through one or more other TLRs, but does not modulate cellular activity mediated through one or more particular TLRs, for example, TLR-7 (e.g., TLR-8, but not TLR-7).

Similarly, "TLR-7-selective" may refer to a compound that modulates TLR-7-mediated cellular activity, but does not modulate cellular activity through any other TLR (TLR-7 only). Alternatively, "TLR-7-selective" may refer to a compound that modulates TLR-7-mediated cellular activity and cellular activity mediated by at least one other TLR, but does not modulate cellular activity mediated through one or more particular TLR, for example, TLR-8 (TLR-7, but not TLR-8).

As noted above, TLR-selective compound may mediate cellular activity through a particular combination of TLRs, but does not modulate activity through another TLR. For example, a compound may mediate cellular activity through both TLR-7 and TLR-9, but not mediate cellular activity through TLR-8. Depending upon the specific nature of the desired selectivity, such as compound may be referred to as, for example, TLR-7-selective (if, e.g., TLR-9-mediated cellular activity is not relevant), TLR-9-selective (if, e.g., TLR-7-mediated cellular activity is not relevant), or TLR-7/9-selective (if, e.g., both TLR-7-mediated cellular activity and TLR-9-mediated cellular activity are relevant).

Whether a given TLR agonist is selective is readily determined using methods known in the art. For example, U.S. Patent Publication No. 2004/0171086, which is incorporated herein by reference, provides a method for determining whether a given compound is a selective TLR agonist.

In some embodiments, the TLR agonist is a pro-drug version of a TLR agonist. Prodrugs are composed of a prodrug portion covalently linked to an active therapeutic agent. Prodrugs are capable of being converted to drugs (active therapeutic agents) in vivo by certain chemical or enzymatic modifications of their structure. Examples of prodrug portions are well-known in the art and can be found, for example in Juliano (1988) *Biological Approaches to the Controlled Delivery of Drugs*, New York Academy of Sciences; Testa (2003) *Hydrolysis in Drug and Prodrug Metabolism: Chemistry, Biochemistry, and Enzymology*, Verlagsgesellschaft Mbh; and Sloan and Dekker (1992) *Prodrugs: Topical and Ocular Drug Delivery*. Examples of prodrug portions include peptides, e.g., peptides that direct the TLR ligand to the site of action, and a peptide which possesses two or more free and uncoupled carboxylic acids at its amino terminus. Other illustrative cleaveable prodrug portions include, but are not limited to ester groups, ether groups, acyl groups, alkyl groups, phosphate groups, sulfonate groups, N-oxides, and tertbutoxy carbonyl groups.

In some embodiments, the TLR agonist is a monomeric TLR agonist. In other embodiments, the TLR agonist is multimerized, e.g., the TLR agonist is polymeric. In some embodiments, a multimerized TLR agonist is homofunctional, e.g., is composed of one type of TLR agonist. In other embodiments, the multimerized TLR agonist is a heterofunctional TLR agonist.

In some embodiments, a TLR ligand is a chimeric TLR ligand (also referred to herein as a "heterofunctional" TLR ligand). In some embodiments, a chimeric TLR agonist comprises a TLR-9 agonist moiety, and a TLR-7 agonist moiety. In other embodiments, a chimeric TLR agonist comprises a selective TLR-7 agonist and a selective TLR-8 agonist. In other embodiments, a chimeric TLR agonist comprises a TLR 9 agonist and a TLR-8 agonist. The following are non-limiting examples of heterofunctional TLR agonists.

In some embodiments, a chimeric TLR ligand has the following formula: 5'-$X_n$—CG-$X_m$—$(B)_q$-3', where X is any nucleotide, and n and m are independently an integer from 0 to 200, and where B is a TLR-7 ligand, and q is 1, 2, 3, 4, 5, 6, 7, 8, 9, or 10.

In some embodiments, a chimeric TLR ligand has the following formula: 5'-$X_n$-$(TCG)_p$-$X_m$—$(B)_q$-3', where X is any nucleotide, n and m are each independently an integer from 0 to 200, where B is a TLR-7 ligand, and where q and p are each independently 1, 2, 3, 4, 5, 6, 7, 8, 9, or 10.

In some embodiments, a chimeric TLR ligand has the following formula: 5'-$(B)_q$—$X_m$—CG-$X_m$-3', where X is any nucleotide, and n and m are independently an integer from 0 to 200, where B is a TLR-7 ligand, and q is 1, 2, 3, 4, 5, 6, 7, 8, 9, or 10.

In some embodiments, a chimeric TLR ligand has the following formula: 5'-$(B)_q$—$X_m$-$(TCG)_p$-$X_m$-3', where X is any nucleotide, n and m are each independently an integer from 0 to 200, and q and p are each independently 1, 2, 3, 4, 5, 6, 7, 8, 9, or 10, and where B is a TLR-7 ligand.

TLR-2 Agonists

Suitable TLR-2 agonists include, but are not limited to synthetic triacylated and diacylated lipopeptides. An illustrative, non-limiting TLR-2 ligand is Pam$_3$Cys (tripalmitoyl-S-glyceryl cysteine) or S-[2,3-bis(palmitoyloxy)-(2R5)-propyl]-Npalmitoyl-(R)-cysteine, where "Pam$_3$" is "tripalmitoyl-Sglyceryl" (see, e.g., Aliprantis et al. (1999) *Science* 285: 736-739). Derivatives of Pam$_3$Cys are also suitable TLR-2 agonists, where derivatives include, but are not limited to, S-[2,3-bis(palmitoyloxy)-(2-R,S)-propyl]-N-palmitoyl-(R)-Cys-(S)-Ser-Lys$_4$-hydroxytrihydrochloride (SEQ ID NO:1); Pam3Cys-Ser-Ser-Asn-Ala (SEQ ID NO:2); PaM$_3$Cys-Ser-(Lys)$_4$ (SEQ ID NO:3); Pam$_3$Cys-Ala-Gly; Pam$_3$Cys-Ser-Gly; Pam$_3$Cys-Ser; PaM$_3$Cys-OMe; Pam$_3$Cys-OH; PamCAG, palmitoyl-Cys((RS)-2,3-di(palmitoyloxy)-propyl)-Ala-Gly-OH; and the like. Another non-limiting example of a suitable TLR-2 agonist is Pam$_2$CSK$_4$ PaM$_2$CSK$_4$ (dipalmitoyl-S-glyceryl cysteine-serine(lysine)$_4$ (SEQ ID NO:4); or Pam$_2$Cys-Ser-(Lys)$_4$) (SEQ ID NO:5) is a synthetic diacylated lipopeptide. Synthetic TLRs agonists have been described in the literature (see, e.g., Kellner et al. (1992) *Biol Chem Hoppe Seyler* 373(1): 51-55; Seifer et al. (1990) *Biochem. J.* 26: 795-802; Lee et al. (2003) *J. Lipid Res.*, 44: 479-486.

In some embodiments, a suitable TLR-2 agonist is a selective TLR-2 agonist, e.g., a TLR-2 agonist selectively activates TLR-2, but does not substantially activate any other Toll-like receptor, such as TLR1, TLR-3, TLR-4, TLR-5, TLR-6, TLR-7, TLR-8, TLR-9, or TLR10. In other embodiments, a suitable TLR-2 agonist activates a TLR-2, and may also activate one or more other Toll-like receptors. Such agonists are "relatively" selective, e.g., such agonists may activate two or more other TLR in addition to TLR-2, but do not activate receptors other than TLR.

TLR-3 Agonists

TLR-3 agonists include, but are not limited to naturally-occurring double-stranded RNA (dsRNA); synthetic ds RNA; and synthetic dsRNA analogs; and the like (see, e.g., Alexopoulou et al. (2001) *Nature* 413:732-738). An illustrative, non-limiting example of a synthetic ds RNA analog is poly(I:C).

TLR-4 Agonists

TLR-4 agonists include, but are not limited to, naturally-occurring lipopolysaccharides (LPS), e.g., LPS from a wide variety of Gram negative bacteria; derivatives of naturally-occurring LPS; synthetic LPS; bacteria heat shock protein-60 (Hsp6O); mannuronic acid polymers; flavolipins; teichuronic acids; *S. pneumoniae* pneumolysin; bacterial fimbriae, respiratory syncytial virus coat protein; and the like.

TLR-7 Agonists

Figure 4:
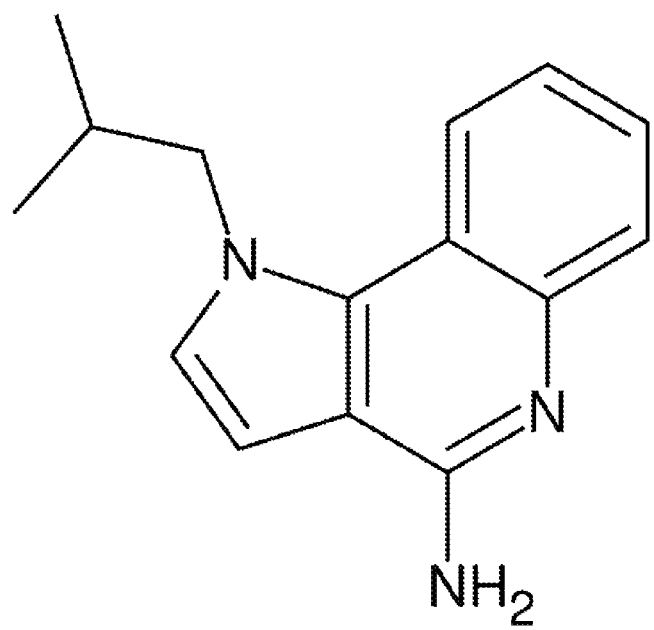
FIG. 4 illustrates the structure of imiquimod (1-isobutyl-1H-imidazo[4,5-c]quinolin-4-amine) (ALDARA™).
Figure 5:
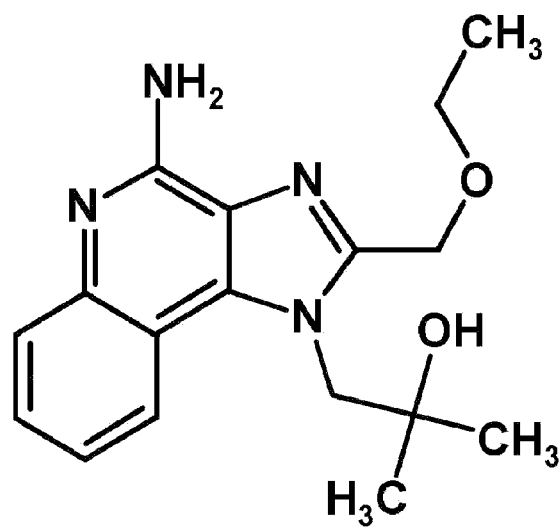
FIG. 5 shows the structure of resiquimod (4-Amino-2-(ethoxymethyl)-a,a-dimethyl-1H-imidazo[4,5-c]quinoline-1-ethanol.
Figure 6A:
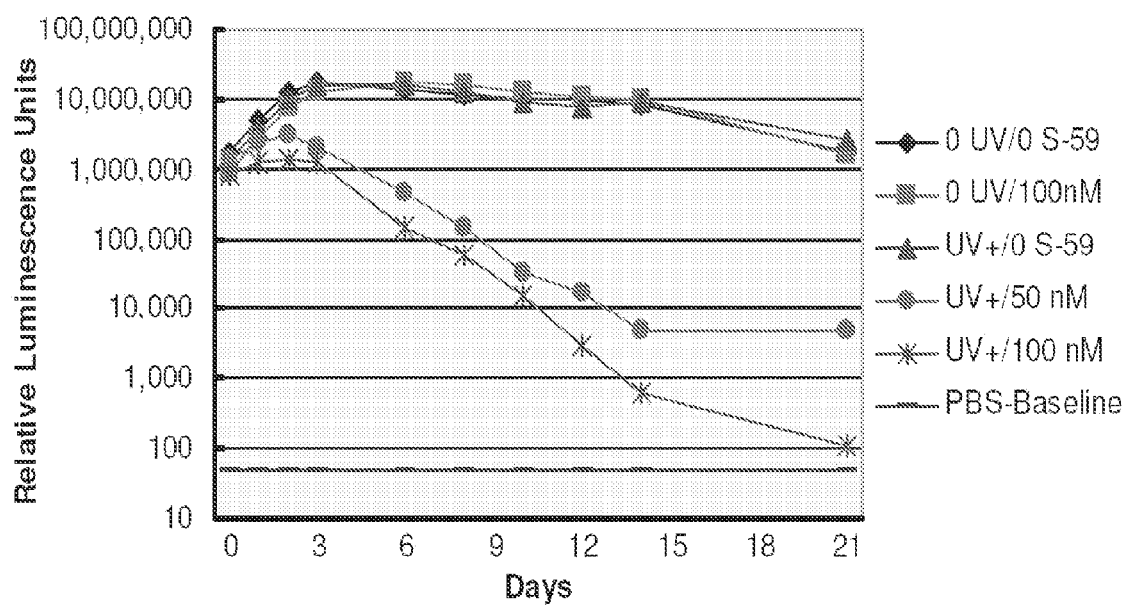
FIGS. 6A, 6B and 6C show that killed but metabolically active (KBMA) *Leishmania chagasi* (LC) die over three weeks in culture but show invasive properties similar to live LC.
Figure 6B:
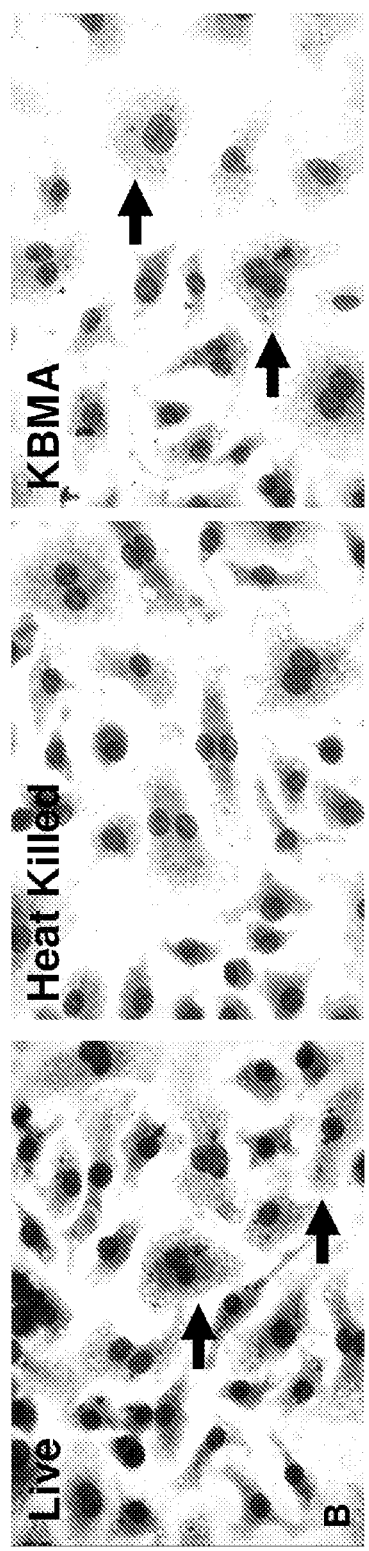
Figure 6C:
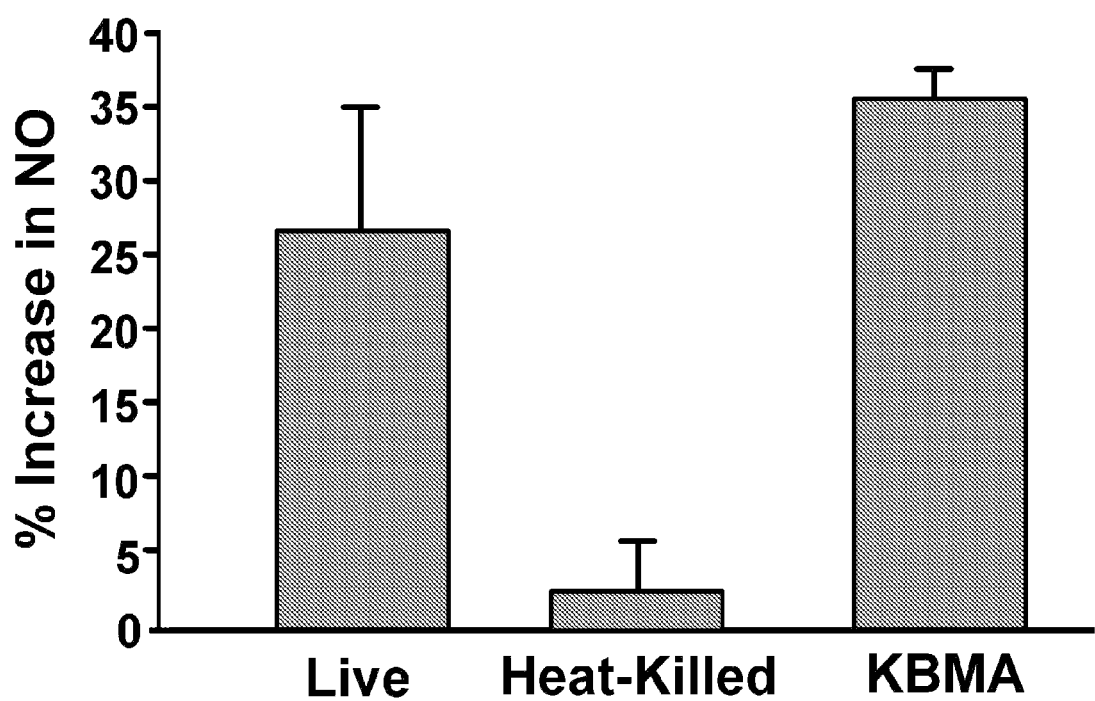
Figure 7:
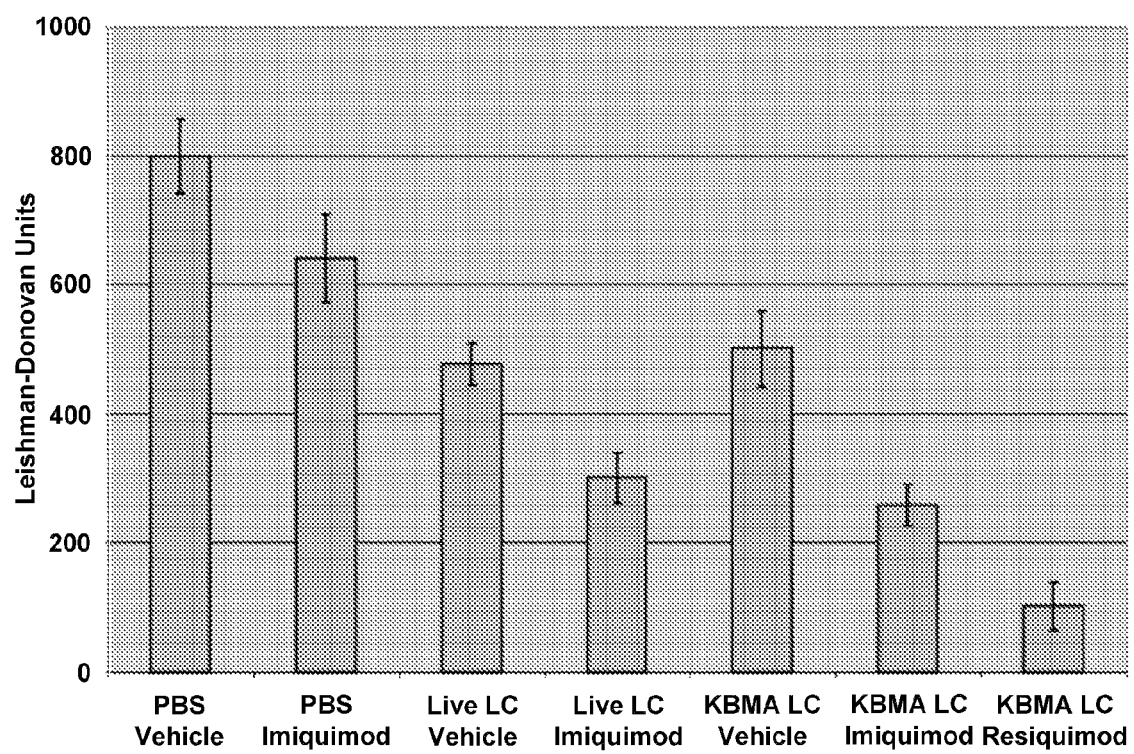
FIG. 7 shows liver parasite burden measured in Leishman Donovan Units (LDU) in mice challenged with *L. chagasi* (LC) after vaccination 3 times with indicated vaccine-adjuvant combinations. Subcutaneous vaccinations were either live *L. chagasi*, KBMA *L. chagasi*, or PBS control. Adjuvants were topical imiquimod, resiquimod, or vehicle cream. **In the KBMA-LC/resiquimod group (rightmost bar), two of eight animals were completely protected with no detectable parasites. Mean+/− ferences, determined by single factor ANOVA, are summarized in Table 5.

TLR-7 agonists include, but are not limited to, imidazoquinoline compounds; guanosine analogs; pyrimidinone compounds such as bropirimine and bropirimine analogs; and the like. Imidazoquinoline compounds that function as TLR-7 ligands include, but are not limited to, imiquimod, (also known as Aldara, R-837, S-26308, see, e.g., FIG. 4), and R-848 (also known as resiquimod, S-28463; having the chemical structure: 4-amino-2-ethoxymethyl-α,α-dimethyl-1H-imidazol[4,5-c]quinoline-ethanol, see, FIG. 5). Suitable imidazoquinoline agents include imidazoquinoline amines, imidazopyridine amines, 6,7-fused cycloalkylimidazopyridine amines, and 1,2 bridged imidazoquinoline amines. These compounds have been described in U.S. Pat. Nos. 4,689,338, 4,929,624, 5,238,944, 5,266,575, 5,268,376, 5,346,905, 5,352,784, 5,389,640, 5,395,937, 5,494,916, 5,482,936, 5,525,612, 6,039,969 and 6,110,929, which are incorporated herein by reference. Particular species of imidazoquinoline agents that are suitable for use in a subject method include R-848 (S-28463); 4-amino-2ethoxymethyl-α,α-dimethyl-1H-imidazo[4,5-c]quinoline-s-i-ethanol; and 1-(2-methylpropyl)-H-imidazo[4,5-c]quinolin-4-amine (R-837 or Imiquimod). Also suitable for use is the compound 4-amino-2-(ethoxymethyl)-α,α-dimethyl-6,7,8,9-tetrahydro-1H-imidazo[4,5-c]quinoline-1-ethanol hydrate (see, e.g., BM-003 in Gorden et al. (2005) *J. Immunol.,* 174: 1259-1268).

Suitable compounds also include those having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamido substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, and tetrahydronaphthyridine amines.

In various embodiments suitable compounds include, but are not limited to, a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine. a tetrahydroimidazonaphthyridine amine, an oxazoloquinoline amine, a thiazoloquinoline amine, an oxazolopyridine amine, a thiazolopyridine amine, an oxazolonaphthyridine amine, and a thiazolonaphthyridine amine.

A substituted imidazoquinoline amine includes an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amines, or a 6-, 7-, 8-, or 9-aryl or heteroaryl substituted imidazoquinoline amine.

Guanosine analogs that function as TLR-7 ligands include certain C8-substituted and N7,C8-disubstituted guanine ribonucleotides and deoxyribonucleotides, including, but not limited to, Loxoribine (7-allyl-8-oxoguanosine), 7-thia-8-oxoguanosine (TOG), 7-deazaguanosine, and 7-deazadeoxyguanosine (see, e.g., Lee et al. (2003) *Proc., Natl. Acad. Sci. USA* 100: 6646-6651). Bropirimine (PNU-54461), a 5-halo-6-phenyl-pyrimidinone, and bropirimine analogs are described in the literature and are also suitable for use (see, e.g., Vroegop et al. (1999) *Intl. J Immunopharmacol.* 21:647-662). Additional examples of suitable C8-substituted guanosines include but are not limited to 8-mercaptoguanosine, 8-bromoguanosine, 8-methylguanosine, 8-oxo-7,8-dihydroguano sine, C8-arylamino-2'-deoxyguano sine, C8-propynyl-guanosine, C8- and N7-substituted guanine ribonucleosides such as 7-allyl-8-oxoguanosine (loxoribine) and 7-methyl-8-oxoguanosine, 8-aminoguanosine, 8-hydroxy-2'-deoxyguanosine, 8-hydroxyguanosine, and the like.

In some embodiments a substituted guanine TLR-7 ligand is monomeric. In other embodiments, a substituted guanine TLR-7 ligand is multimeric. Thus, in some embodiments, a TLR-7 ligand has the formula: $(B)_q$, where B is a substituted guanine TLR-7 ligand, and q is 1, 2, 3, 4, 5, 6, 7, 8, 9, or 10. The individual TLR-7 ligand monomers in a multimeric TLR-7 ligand are linked, covalently or noncovalently, either directly to one another or through a linker.

Suitable TLR-7 agonists include a TLR-7 ligand as described in U.S. Patent Publication No. 2004/0162309, which is incorporated herein by reference.

In some embodiments, a TLR-7 agonist is a selective TLR-7 agonist, e.g., the agonist modulates cellular activity through TLR-7, but does not modulate cellular activity through TLR-8. TLR-7-selective agonists include those shown in Tables 2, 4, and 5 of U.S. Patent Publication No. 2004/0171086. Such TLR-7 selective agonist compounds include, but are not limited to, the compounds shown in Table 2, below, which compounds are listed in Table 2 of U.S. Patent Publication No. 2004/0171086, which is incorporated herein by reference.

TABLE 2

Illustrative TLR-7 agonists.

| | |
|---|---|
| $N^1$-{4-[4-amino-2-(2-methoxyethyl)-6,7,8,9-tetrahydro-1H-imidazo[4,5-c]quinolin-1-yl]buty1}-4-fluoro-1-benzenesulfonamide | U.S. Pat. No. 6,331,539<br>Example 121 |
| $N^1$-[4-(4-amino-2-(2-methoxyethyl)-1Himidazo[4,5-c]quinolin-1-yl)butyl]-4-fluoro-1-benzenesulfonamide | U.S. Pat. No. 6,677,349<br>Example 235 |
| N-[4-(4-amino-2-propyl-1H-imidazo[4,5-c]quinolin-1-yl)butyl]methanesulfonamide-N-{3-[4-amino-2-(2-methoxyethyl)-1H-imidazo[4,5-c]quinolin-1-yl]-2,2-dimethylpropyl]benzamide | U.S. Pat. No. 2003/0144283<br>Example 190 |
| N-(2-{2-[4-amino-2-(2-methoxyethyl)-1H-imidazo[4,5-c]quinolin-1-yl]ethoxy}ethyl)-N-methylmethanesulfonamide | U.S. Pat. No. 6,683,088<br>Example 3 |

TABLE 2-continued

Illustrative TLR-7 agonists.

| Compound | Reference |
|---|---|
| N-(2-{2-[4-amino-2-(2-methoxyethyl)-6,7,8,9-- tetrahydro-1H-imidazo[4,5-c]quinolin-1-yl]ethoxy}ethyl)benzamide | U.S. Pat. No. 6,660,747 Example 6 |
| N-[4-(4-amino-2-methyl-1H-imidazo[4,5-c]quinolin-1-yl)butyl]cyclopentanecarboxamide | U.S. Pat. No. 2003/144283 Example 201 |
| 1-[4-(1,1-dioxidoisothiazolidin-2-yl)butyl]-2-(2-methoxyethyl)-1H-imidazo[4,5-c]quinolin-4-amine | U.S. Pat. No. 6,677,349 Example 266 |
| 2-methyl-1-[5-methylsulfonyl)pentyl-6,7,8,9--tetrahydro-1H-imidazo[4,5-c]quinolin-4-amine | U.S. Pat. No. 6,667,312 Example 75 |
| N-{2-[4-amino-2-(ethoxymethyl)-6,7-dimethyl--1H-imidazo[4,5-c]pyridin-1-yl]-1,1-dimethylethyll-N'-cyclohexylurea | U.S. Pat. No. 6,545,017 |
| N-[2-(4-amino-2-ethyl-1H-imidazo[4,5-c]quinolin-1-y1)-1,1-dimethylethylibenzamide | U.S. Pat. No. 2003/144283 |
| N-[3-(4-amino-2-butyl-1H-imidazo[4,5-c]quinolin-1-y1)-2,2-dimethylpropyl]methanesulfonamide | U.S. Pat. No. 6,677,349 |
| 1-[6-(methanesulfonyl)hexyl-6,7-dimethyl-2--propyl-1H-imidazo[4,5-c]pyridin-4-amine | U.S. Pat. No. 2004/010007 Example 91 |
| 6-(4-amino-2-propy1-1H-imidazo[4,5-c]quinolin-1-yl)-N-methoxy-N-methylhexamide | U.S. Ser. No. 60/524,961 Example 19 |
| 1-[2,2-dimethyl-3-(methylsulfonyl)propy1]-2-(ethoxymethyl)-1H-imidazo[4,5-c]quinolin-4-amine | U.S. Pat. No. 6,667,312 |
| N'-[4-(4-amino-2-methyl-1H-imidazo[4,5--c]quinolin-1-yl)butyl]-methyl-N-phenylurea | U.S. Pat. No. 6,541,485 |
| 1-{3-[4-amino-1-(2-methylpropy1)-1H-imidazo[4,5-c]quinolin-8-yl]phenyl}ethanone | U.S. Ser. No. 10/739,787 Example 120 |
| 7-(4-amino-2-propy1-1H-imidazo[4,5-c]quinolin-1-yl)-2-methylheptan-2-ol | U.S. Pat. No. 4,689,338 |
| N-methyl-4-(4-amino-2-ethyl-1H-imidazo[4,5-c]quinolin-1-yl)butane-1-sulfonamide | U.S. Ser. No. 60/533,465 Example 4 |
| N-(4-methoxybenzyl)-4-(4-amino-2-ethyl-1H-imidazo[4,5-c]quinolin-1-yl)butane-1-sulfonamide | U.S. Ser. No. 60/533,465 Example 5 |
| N-{2-[4-amino-2-(ethoxymethyl)-6,7-dimethyl--1H-imidazo[4,5-c]pyridin-1-yl]-1,1-dimethylethyl}methanesulfonamide | U.S. Pat. No. 6,525,064 |
| 2-ethoxymethyl-1-(3-methoxypropyl)-7-(5-hydroxymethylpyridin-3-yl)-1H-imidazo[4,5-c]quinolin-4-amine | U.S. Ser. No. 10/739,787 Example 167 |
| 1-[(2,2-dimethy1-1,3-dioxolan-4-yl)methyl]-2-(ethoxymethyl)-7-(pyridin-3-yl)-1H-imidazo[4,5-c]quinolin-4-amine | U.S. Ser. No. 10/739,787 Example 159 |
| 4-[3-(4-amino-6,7-dimethy1-2-propy1-1H-imidazo[4,5-c]pyridin-1-y0propane-1-sulfonyl]--benzoic-acid-ethyl-ester | U.S. Pat. No. 2004/010007 Example 99 |
| 2-butyl-1-{2-[2-(methylsulfonypethoxy]ethy11--1H-imidazo[4,5-c]quinolin-4-amine | U.S. Ser. No. 60/526,772 Example 2 |
| N-(2-{4-amino-2-ethoxymethyl-7-[6-(methanesulfonylamino)hexyloxy]-1H-imidazo[4,5--c]quinolin-1-y1}-1,1-dimethylethyl)methanesulfonamide | U.S. Ser. No. 60/508,634 Example 45 |
| N-(6-{[4-amino-2-ethoxymethyl-1-(2-methanesulfonylamino-2-methylpropy1)-1Himidazo[4,5-c]quinolin-7-yl]oxy]hexyl)acetamide | U.S. Ser. No. 60/508,634 Example 46 |
| 1-[4-(1,1-dioxidoisothiazolidin-2-yl)butyl]-2--ethoxymethyl-7-(pyridin-3-yl)-1H-imidazo[4,5-c]quinolin-4-amine | U.S. Ser. No. 10/739,787 Example 153 |
| 1-[4-(1,1-dioxidoisothiazolidin-2-yl)butyl]-2--ethoxymethyl-7-(pyridin-4-yl)-1H-imidazo[4,5-c]quinolin-4-amine | U.S. Ser. No. 10/739,787 Example 154 |
| 1-[4-(1,1-dioxidoisothiazolidin-2-yl)butyl]-2-ethoxymethyl-7-phenyl-1H-imidazo[4,5--c]quinolin-4-amine | U.S. Ser. No. 10/739,787 Example 152 |
| 2-(ethoxymethyl)-1-{[1-(methylsulfonyl)piperidin-4-yl]methy1}-7-(pyridin-3-yl)-1H-imidazo[4,5-c]quinolin-4-amine | U.S. Ser. No. 10/739,787 Example 178 |
| 2-(ethoxymethyl)-1-[(1-isobutyrylpiperidin-4-yl)methy1]-7-(pyridin-3-y1)-1H-imidazo[4,5-c]quinolin-4-amine | U.S. Ser. No. 10/739,787 Example 179 |
| 2-(ethoxymethyl)-1-{[1-(morpholin-4--ylcarbonyl)piperidin-4-yl]methy11-7-(pyridin-3-y1)-1H-imidazo[4,5-c]quinolin-4-amine | U.S. Ser. No. 10/739,787 Example 180 |
| Cyclopropanecarboxylic-acid-[3-(4-amino-2--propy1-1H-imidazo[4,5-c]quinolin-1-yl]propoxy]amide | U.S. Ser. No. 60/494,605 Example 2 |
| Isopropylcarbamic-acid-4-amino-2-(2--methoxyethyl)-1-propyl-1H-imidazo[4,5-c]quinolin-7-y1-ester | U.S. Ser. No. 60/508,634 Example 366 |
| Ethyl-4-(4-amino-2-propy1-1H-imidazo[4,5-c]quinolin-1-yl)butyrate | U.S. Ser. No. 60/524,961 Example 38 |
| 1-[4-amino-2-ethy1-7-(pyridin-3-yl)-1H-imidazo[4,5-c]quinolin-1-yl]-2-methylpropan-2-ol | U.S. Ser. No. 10/739,787 Example 143 |

TABLE 2-continued

Illustrative TLR-7 agonists.

| | |
|---|---|
| 1-{4-amino-2-ethyl-7-[5-(hydroxymethyl)pyridin-3-yl]-1H-imidazo[4,5--c]quinolin-1-yll-2-methylpropan-2-ol | U.S. Ser. No. 10/739,787 Example 144 |
| 1-{3-[4-amino-2-(2-methoxyethyl)-8-(pyridin-3-y1)-1H-imidazo[4,5-c]quinolin-1-yl]propyllpyrrolidin-2-one | U.S. Ser. No. 10/739,787 Example 188 |
| N-(2-{4-amino-2-ethoxymethyl-7-[6-(methanesulfonylamino)hexyloxy]-1Himidazo[4,5-c]quinolin-1-yl}-1,1-dimethylethyl)acetamide | U.S. Ser. No. 60/508,634 Example 49 |
| 1-{3-[4-amino-7-(3-hydroxymethylpheny1)-2-(2-methoxyethyl)-1H-imidazo[4,5-c]quinolin-1-yl]propyl}pyrrolidin-2-one | U.S. Ser. No. 10/739,787 Example 185 |
| N-{4-[4-amino-2-ethoxymethyl1-7-(pyridin-3-y1)-1H-imidazo[4,5-c]quinolin-1-yl]butyl}-N'-propylurea | U.S. Ser. No. 10/739,787 Example 378 |
| N-{4-[4-amino-2-ethoxymethyl1-7-(pyridin-3-y1)-1H-imidazo[4,5-c]quinolin-1-yl)butyl}butyramide | U.S. Ser. No. 10/739,787 Example 372 |
| 5-(4-amino-2-propy1-1H-imidazo[4,5-c]quinolin-1-yl)-4,4-dimethylpentan-2-one | U.S. Ser. No. 60/524,961 Example 36 |
| 1-cyclohexylmethy1-2-ethoxymethyl-7-(5-hydroxymethylpyridin-3-yl)-1H-imidazo[4,5-c]quinolin-4-amine | U.S. Ser. No. 10/739,787 Example 439 |
| N,N-dimethyl-5-(4-amino-2-ethoxymethyl-1H-imidazo[4,5-c]quinolin-1-yl)pentane-1-sulfonamide | U.S. Ser. No. 60/533,465 Example 17 |
| N-{3-[(4-amino-2-ethoxymethyl1-1H-imidazo[4,5-c]quinolin-1-yl)aminotropyllmethanesulfonamide | U.S. Ser. No. 60/532,191 Example 14 |
| N,N-dimethyl-4-(4-amino-2-ethoxymethyl-1H-imidazo[4,5-c]quinolin-1-yl)butane-1-sulfonamide | U.S. Ser. No. 60/533,465 Example 11 |

Additional suitable TLR-7 selective agonists include, but are not limited to, 2-(ethoxymethyl)-1-(2-methylpropyl)-1H-imidazo[4,5-c]quinolin-4-amine (see, e.g., Example 40, U.S. Pat. No. 5,389,640, which is incorporated herein by reference); 2-methyl-142-(3-pyridin-3-ylpropoxy)ethyl]-1H-imidazo[4,5-c]quinolin-4-amine (see, e.g., WO 02/46193, which is incorporated herein by reference); N-(2-1244-amino-2-(2-methoxyethyl)-1H-imidazo-[4,5-c]quinolin-1-yl]ethoxyl ethyl)-N-methylcyclohexanecarboxamide (see, e.g., U.S. Patent Publication No. 2004/0171086; IRM3, which is incorporated herein by reference); 142-(benzyloxy)ethyl]-2-methyl-1H-imidazo[4,5-c]quinolin-4-amine (see, e.g., WO 02/46189, which is incorporated herein by reference); N-{8-[4-amino-2-(2-methyoxyethyl)-1H-imidazo[4,5-c]quinolin-1-yl]octyll-N-phenylurea (see, e.g., U.S. Patent Publication No. 2004/0171086, which is incorporated herein by reference); 2-butyl-1-[5-(methylsulfonyl)pentyl]-1H-imidazo[4,5-c]quinolin-4-amine (see, e.g., WO 02/46192, which is incorporated herein by reference); N-1344-amino-2-(2-methoxyethyl)-1H-imidazo[4,5-c]quinolin-1-yl]propyl}-4-methylbenzenesulfonamide (see, e.g., U.S. Pat. No. 6,331,539, which is incorporated herein by reference); and N-[4-(4-amino-2-ethyl-1H-imidazo[4,5-c]quinolin-1-yl)butyl]cyclohexanecarboxamide (see, e.g., U.S. Patent Publication No. 2004/0171086; which is incorporated herein by reference). Also suitable for use is the TLR-7-selective agonist N-44-(4-amino-2-ethyl-1H-imidazo[4,5-c]quinolin-1-yl)butyl-]methanesulfonamide (see, e.g., BM-001 in Gorden et al. (2005) *J. Immunol.* 174: 1259-1268).

TLR-8 Agonists

Suitable TLR-8 agonists include, but are not limited to such as R-848, and derivatives and analogs thereof. Suitable TLR-8 agonists include, but are not limited to compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

In certain embodiments the TLR-8 agonist comprises an amide substituted imidazoquinoline amine. In various embodiments, the TLR-8 agonist comprises a sulfonamide substituted imidazoquinoline amine. In another embodiment, the TLR-8 agonist comprises a urea substituted imidazoquinoline amine. In another embodiment, the TLR-8 agonist comprises an aryl ether substituted imidazoquinoline amine. In another embodiment, the TLR-8 agonist comprises a heterocyclic ether substituted imidazoquinoline amine. In another embodiment, the TLR-8 agonist comprises an amido ether substituted imidazoquinoline amine. In another embodiment, the TLR-8 agonist comprises a sulfonamido ether substituted imidazoquinoline amine. In another embodiment, the TLR-8 agonist comprises a urea substituted imidazoquinoline ether. In another embodiment, the TLR-8 agonist comprises a thioether substituted imidazoquinoline amine. In another alternative embodiment, the TLR-8 agonist comprises a 6-, 7-,8-, or 9-aryl or heteroaryl substituted imidazoquinoline amine.

In another embodiment, the TLR-8 agonist comprises an amide substituted tetrahydroimidazoquinoline amine. In another embodiment, the TLR-8 agonist comprises a sulfonamide substituted tetrahydroimidazoquinoline amine. In another embodiment, the TLR-8 agonist comprises a urea substituted tetrahydroimidazoquinoline amine.

In another embodiment, the TLR-8 agonist comprises an aryl ether substituted tetrahydroimidazoquinoline amine. In another embodiment, the TLR-8 agonist comprises a heterocyclic ether substituted tetrahydroimidazoquinoline amine. In another embodiment, the TLR-8 agonist comprises an amido ether substituted tetrahydroimidazoquinoline amine. In another embodiment, the TLR-8 agonist comprises a sulfonamido ether substituted tetrahydroimidazoquinoline amine. In another embodiment, the TLR-8 agonist comprises a urea substituted tetrahydroimidazoquinoline ether. In another embodiment, the TLR-8 agonist comprises a thioether substituted tetrahydroimidazoquinoline amine.

In another embodiment, the TLR-8 agonist comprises an amide substituted imidazopyridine amines. In another embodiment, the TLR-8 agonist comprises a sulfonamide substituted imidazopyridine amine. In another embodiment, the TLR-8 agonist comprises a urea substituted imidazopyridine amine. In another embodiment, the TLR-8 agonist comprises an aryl ether substituted imidazopyridine amine. In another embodiment, the TLR-8 agonist comprises a heterocyclic ether substituted imidazopyridine amine. In another embodiment, the TLR-8 agonist comprises an amido ether substituted imidazopyridine amine. In another embodiment, the TLR-8 agonist comprises a sulfonamido ether substituted imidazopyridine amine. In another embodiment, the TLR-8 agonist comprises a urea substituted imidazopyridine ether. In another embodiment, the TLR-8 agonist comprises a thioether substituted imidazopyridine amine.

In another embodiment, the TLR-8 agonist comprises a 1,2-bridged imidazoquinoline amine. In another embodiment, the TLR-8 agonist comprises a 6,7-fused cycloalkylimidazopyridine amine.

In another embodiment, the TLR-8 agonist comprises an imidazonaphthyridine amine. In another embodiment, the TLR-8 agonist comprises a tetrahydroimidazonaphthyridine amine. In another embodiment, the TLR-8 agonist comprises an oxazoloquinoline amine. In another embodiment, the TLR-8 agonist comprises a thiazoloquinoline amine. In another embodiment, the TLR-8 agonist comprises an oxazolopyridine amine. In another embodiment, the TLR-8 agonist comprises a thiazolopyridine amine. In another embodiment, the TLR-8 agonist comprises an oxazolonaphthyridine amine. In another embodiment, the TLR-8 agonist comprises a thiazolonaphthyridine amine.

In yet another embodiment, the TLR-8 agonist comprises a 1H-imidazo dimer fused to a pyridine amine, quinoline amine, tetrahydroquinoline amine, naphthyridine amine, or a tetrahydronaphthyridine amine.

In some embodiments, the TLR-8 agonist comprises a selective TLR-8 agonist, e.g., the agonist modulates cellular activity through TLR-8, but does not modulate cellular activity through TLR-7. TLR-8-selective agonists include those shown in Tables 1, 4, and 5 of U.S. Patent Publication No. 2004/0171086, which is incorporated herein by reference. Such TLR-8 selective agonist compounds include, but are not limited to, the compounds shown in Table 3, below, which compounds are listed in Table 1 of U.S. Patent Publication No. 2004/0171086.

TABLE 3

Illustrative TLR-8 selective compounds.

N-{4-[4 amino-2-(2-methoxyethyl)-1H-imidazo[4,5-c]quinolin-1-yl]butyl}quinolin-3-carboxamide
N-{4-[4 amino-2-(2-methoxyethyl)-1H-imidazo[4,5-c]quinolin-1-yl]butyl}quinoxoline-2-carboxamide
N-[4-(4-amino-2-propy1-1H-imidazo[4,5-e]quinolin-1-yl)butyl]moipholine-4-carboxamide Other suitable TLR-8-selective agonists include, but are not limited to, 2-propylthiazolo[4,5-c]quinolin-4-amine (see, e.g., U.S. Pat. No. 6,110,929, which is incorporated herein by reference); $N^1$-2-(4-amino-2-butyl-1H-imidazo[4,5-c][1,5] naphthridin-1-yl-)ethyl]-2-amino-4-methylpentanamide (see, e.g., U.S. Pat. No. 6,194,425, which is incorporated herein by reference); $N^1$-[4-(4-amino-1H-imidazo[4,5-c] quinolin-1-yl)butyl]-2-phenoxybenzamide (see, e.g., U.S. Pat. No. 6,451,810, which is incorporated herein by reference); $N^1$-2-(4-amino-2-butyl-1H-imidazo[4,5-c]quinolin-1-yl)ethyl]-1-propanesulfonamide (see, e.g., U.S. Pat. No. 6,331,539, which is incorporated herein by reference); N-{-2-(2-(4-amino-2-ethyl-1H-imidazo[4,5-c]quinolin-1-yl) ethyoxy]ethyl}-N'-phenylurea (see, e.g., U.S. Patent Publication No. 2004/0171086, which is incorporated herein by reference); 1-{4-[3,5-dichlorophenyl)thio]butyl}-2-ethyl-1H-imidazo[4,5-c]quinolin-4-amine ((see, e.g., U.S. Patent Publication No. 2004/0171086, is incorporated herein by reference); N-{2-[4-amino-2-(ethoxymethyl)-1H-imidazo[4,5-c]quinolin-1-yl]ethyl}-N'-(3-cyanophenyl)urea (see, e.g., WO 00/76518; and U.S. Patent Publication No. 2004/0171086, which are incorporated herein by reference); and 4-amino-α,α-dimethyl-2-methoxyethyl-1H-imidazo[4,5-c] quinoline-1-ethanol (see, e.g., U.S. Pat. No. 5,389,640, which is incorporated herein by reference). Included for use as TLR-8-selective agonists are the compounds depicted in Tables 4 and 5 of U.S. Patent Publication No. 2004/0171086. Also suitable for use is the compound 2-propylthiazolo-4,5-c]quinolin-4-amine (see, e.g., BM-002 in Gorden et al. (2005) supra).

TLR-9 Agonists

Examples of TLR-9 agonists (also referred to herein as "TLR-9 ligands") include nucleic acids comprising the sequence 5'-CG-3'(a "CpG nucleic acid"), particularly where the C is unmethylated. The terms "polynucleotide," and "nucleic acid," as used interchangeably herein in the context of TLR-9 ligand molecules, refer to a polynucleotide of any length, and encompasses, inter alia, single- and double-stranded oligonucleotides (including deoxyribonucleotides, ribonucleotides, or both), modified oligonucleotides, and oligonucleosides, alone or as part of a larger nucleic acid construct, or as part of a conjugate with a non-nucleic acid molecule such as a polypeptide. Thus a TLR-9 ligand can be, for example, single-stranded DNA (ssDNA), double-stranded DNA (dsDNA), single-stranded RNA (ssRNA) or double-stranded RNA (dsRNA). TLR-9 ligands also encompasses crude, detoxified bacterial (e.g., mycobacterial) RNA or DNA, as well as enriched plasmids enriched for a TLR-9 ligand. In some embodiments, a "TLR-9 ligand-enriched plasmid" refers to a linear or circular plasmid that comprises or is engineered to comprise a greater number of CpG motifs than normally found in mammalian DNA.

Illustrative, non-limiting TLR-9 ligand-enriched plasmids are described in, for example, Roman et al. (1997) *Nat Med.* 3(8):849-54. Modifications of oligonucleotides include, but are not limited to, modifications of the 3'OH or 5'OH group, modifications of the nucleotide base, modifications of the sugar component, and modifications of the phosphate group.

In various embodiments a TLR-9 ligand can comprise at least one nucleoside comprising an L-sugar. In various embodiments the L-sugar may be deoxyribose, ribose, pentose, deoxypentose, hexose, deoxyhexose, glucose, galactose, arabinose, xylose, lyxose, or a sugar "analog" cyclopentyl group. In various embodiments the L-sugar may be in pyranosyl or furanosyl form.

TLR-9 ligands generally do not provide for, nor is there any requirement that they provide for, expression of any amino acid sequence encoded by the polynucleotide, and thus the sequence of a TLR-9 ligand may be, and generally is, non-coding. TLR-9 ligands can comprise a linear double or single-stranded molecule, a circular molecule, or can comprise both linear and circular segments. TLR-9 ligands can be single-stranded, or may be completely or partially double-stranded.

In certain embodiments, a TLR-9 ligand for use in a subject method comprises an oligonucleotide, e.g., a sequence of from about 5 nucleotides to about 200 nucleotides, from about 10 nucleotides to about 100 nucleotides, from about 12 nucleotides to about 50 nucleotides, from about 15 nucleotides to about 25 nucleotides, from 20 nucleotides to about 30 nucleotides, from about 5 nucleotides to about 15 nucleotides, from about 5 nucleotides to about 10 nucleotides, or from about 5 nucleotides to about 7 nucleotides in length. In some embodiments, a TLR-9 ligand that is less than about 15 nucleotides, less than about 12 nucleotides, less than about 10 nucleotides, or less than about 8 nucleotides in length is associated with a larger molecule, e.g., adsorbed onto an insoluble support, as described below.

A TLR-9 ligand can be isolated from a bacterium, e.g., separated from a bacterial source; produced by synthetic means (e.g., produced by standard methods for chemical synthesis of polynucleotides); produced by standard recombinant methods, then isolated from a bacterial source; or a combination of the foregoing. In many embodiments, a TLR-9 ligand is purified, e.g., is at least about 80%, at least about 90%, at least about 95%, at least about 98%, at least about 99%, or more, e.g., 99.5%, 99.9%, or more, pure. In many embodiments, the TLR-9 ligand is chemically synthesized, then purified.

In certain embodiments, a TLR-9 ligand is part of a larger nucleotide construct (e.g., a plasmid vector, a viral vector, or other such construct). A wide variety of plasmid and viral vector are known in the art, and need not be elaborated upon here. A large number of such vectors have been described in various publications, including, e.g., *Current Protocols in Molecular Biology*, (F. M. Ausubel, et al., Eds. 1987, and updates). Many vectors are commercially available.

In certain embodiments a TLR-9 ligand used in the present invention comprises at least one unmethylated CpG motif. The relative position of any CpG sequence in a polynucleotide in certain mammalian species (e.g., rodents) is 5'-CG3' (i.e., the C is in the 5' position with respect to the G in the 3' position).

In some embodiments, a TLR-9 ligand comprises a central palindromic core sequence comprising at least one CpG sequence, where the central palindromic core sequence contains a phosphodiester backbone, and where the central palindromic core sequence is flanked on one or both sides by phosphorothioate backbone-containing polyguanosine sequences.

In other embodiments, a TLR-9 ligand comprises one or more TCG sequences at or near the 5' end of the nucleic acid; and at least two additional CG dinucleotides. In some of these embodiments, the at least two additional CG dinucleotides are spaced three nucleotides, two nucleotides, or one nucleotide apart. In some of these embodiments, the at least two additional CG dinucleotides are contiguous with one another. In some of these embodiments, the TLR-9 ligand comprises $(TCG)_n$, where n=one to three, at the 5' end of the nucleic acid. In other embodiments, the TLR-9 ligand comprises $(TCG)_n$, where n=one to three, and where the $(TCG)_n$ sequence is flanked by one nucleotide, two nucleotides, three nucleotides, four nucleotides, or five nucleotides, on the 5' end of the $(TCG)_n$ sequence.

Illustrative consensus CpG motifs of TLR-9 ligands useful in the invention include, but are not necessarily limited to:

5'-Purine-Purine-(C)-(G)-Pyrimidine-Pyrimidine-3' (SEQ ID NO:68), in which the TLR-9 ligand comprises a CpG motif flanked by at least two purine nucleotides (e.g., GG, GA, AG, AA, II, etc.,) and at least two pyrimidine nucleotides (CC, TT, CT, TC, UU, etc.);

5'-Purine-TCG-Pyrimidine-Pyrimidine-3 (SEQ ID NO:79);

5'-TCG-N—N-3; where N is any base (SEQ ID NO:849);

5'-$N_x(CG)_nN_y$ (SEQ ID NO:944), where N is any base, where x and y are independently any integer from 0 to 200, e.g., 0, 1, 2, 3, 4, 5, 6, 7, 8, 9, 10, 11-15, 16-20, 21-25, 25-30, 30-50, 50-75, 75-100, 100-150, or 150-200; and n is any integer that is 1 or greater, e.g., 1, 2, 3, 4, 5, 6, 7, 8, 9, 10, or greater.

5'-$N_x(TCG)_nN_y$ (SEQ ID NO:10), where N is any base, where x and y are independently any integer from 0 to 200, e.g., 0, 1, 2, 3, 4, 5, 6, 7, 8, 9, 10, 11-15, 16-20, 21-25, 25-30, 30-50, 50-75, 75-100, 100-150, or 150-200; and n is any integer that is 1 or greater, e.g., 1, 2, 3, 4, 5, 6, 7, 8, 9, 10, or greater.

5'-$(TCG)_n$-3' (SEQ ID NO:11), where n is any integer that is 1 or greater, e.g., to provide a TCG-based TLR-9 ligand (e.g., where n=3, the polynucleotide comprises the sequence 5'-TCGNNTCGNNTCG-3; SEQ ID NO:12);

5'$N_m$-$(TCG)_n$-$N_p$-3' (SEQ ID NO:13), where N is any nucleotide, where m is zero, one, two, or three, where n is any integer that is 1 or greater, and where p is one, two, three, or four;

5$N_m$-$(TCG)_n$-Np-3' (SEQ ID NO:14), where N is any nucleotide, where m is zero to 5, and where n is any integer that is 1 or greater, where p is four or greater, and where the sequence N—N—N—N comprises at least two CG dinucleotides that are either contiguous with each other or are separated by one nucleotide, two nucleotides, or three nucleotides; and 5'-Purine-Purine-CG-Pyrimidine-TCG-3' (SEQ ID NO:15).

A non-limiting example of a TLR-9 ligand comprising 5'-(TCG)n-3' (SEQ ID NO:16), where n is any integer that is 1 or greater, is a TLR-9 ligand comprising the sequence 5' TCGTCGTTTTGTCGTTTTGTCGTT 3' (SEQ ID NO:17).

Where a nucleic acid TLR-9 ligand comprises a sequence of the formula: 5'-$N_m$-$(TCG)_n$-$N_p$-3' (SEQ ID NO:18), where N is any nucleotide, where m is zero to 5, and where n is any integer that is 1 or greater, where p is four or greater, and where the sequence N—N—N—N (SEQ ID NO:19) comprises at least two CG dinucleotides that are either contiguous with each other or are separated by one nucleotide, two nucleotides, or three nucleotides, exemplary TLR-9 ligands useful in the invention include, but are not necessarily limited to:

(1) a sequence of the formula in which n=2, and $N_p$ is NNCGNNCG (SEQ ID NO:20);

(2) a sequence of the formula in which n=2, and $N_p$ is AACGTTCG (SEQ ID NO:21);

(3) a sequence of the formula in which n=2, and $N_p$ is TTCGAACG (SEQ ID NO:22);

(4) a sequence of the formula in which n=2, and $N_p$ is TACGTACG (SEQ ID NO:23);

(5) a sequence of the formula in which n=2, and $N_p$ is ATCGATCG (SEQ ID NO:24);

(6) a sequence of the formula in which n=2, and $N_p$ is CGCGCGCG (SEQ ID NO:25);

(7) a sequence of the formula in which n=2, and $N_p$ is GCCGGCCG (SEQ ID NO:26);

(8) a sequence of the formula in which n=2, and $N_p$ is CCCGGGCG (SEQ ID NO:27);

(9) a sequence of the formula in which n=2, and $N_p$ is GGCGCCCG (SEQ ID NO:28);

(10) a sequence of the formula in which n=2, and $N_p$ is CCCGTTCG (SEQ ID NO:29);

(11) a sequence of the formula in which n=2, and $N_p$ is GGCGTTCG (SEQ ID NO:30);

(12) a sequence of the formula in which n=2, and $N_p$ is TTCGCCCG (SEQ ID NO:31);

(13) a sequence of the formula in which n=2, and $N_p$ is TTCGGGCG (SEQ ID NO:32);

(14) a sequence of the formula in which n=2, and $N_p$ is AACGCCCG (SEQ ID NO:33);

(15) a sequence of the formula in which n=2, and $N_p$ is AACGGGCG (SEQ ID NO:34);

(16) a sequence of the formula in which n=2, and $N_p$ is CCCGAACG (SEQ ID NO:35); and

(17) a sequence of the formula in which n=2, and $N_p$ is GGCGAACG (SEQ ID NO:36); and where, in any of 1-17, m=zero, one, two, or three.

Where a nucleic acid TLR-9 ligand comprises a sequence of the formula: 5'Nm-(TCG)$_n$-Np-3', where N is any nucleotide, where m is zero, one, two, or three, where n is any integer that is 1 or greater, and where p is one, two, three, or four, exemplary TLR-9 ligands useful in the invention include, but are not necessarily limited to:

(1) a sequence of the formula where m=zero, n=1, and $N_p$ is T-T-T (SEQ ID NO:37);

(2) a sequence of the formula where m=zero, n=1, and $N_p$ is T-T-T-T (SEQ ID NO:38);

(3) a sequence of the formula where m=zero, n=1, and $N_p$ is C—C—C—C (SEQ ID NO:39);

(4) a sequence of the formula where m=zero, n=1, and $N_p$ is A-A-A-A (SEQ ID NO:40);

(5) a sequence of the formula where m=zero, n=1, and $N_p$ is A-G-A-T (SEQ ID NO:41);

(6) a sequence of the formula where $N_m$ is T, n=1, and $N_p$ is T-T-T (SEQ ID NO:42);

(7) a sequence of the formula where $N_m$ is A, n=1, and $N_p$ is T-T-T (SEQ ID NO:43);

(8) a sequence of the formula where $N_m$ is C, n=1, and $N_p$ is T-T-T (SEQ ID NO:44);

(9) a sequence of the formula where $N_m$ is G, n=1, and $N_p$ is T-T-T (SEQ ID NO:45);

(10) a sequence of the formula where $N_m$ is T, n=1, and $N_p$ is A-T-T (SEQ ID NO:46);

(11) a sequence of the formula where $N_m$ is A, n=1, and $N_p$ is A-T-T (SEQ ID NO:47); and

(12) a sequence of the formula where $N_m$ is C, n=1, and $N_p$ is A-T-T (SEQ ID NO:48).

The core structure of a TLR-9 ligand useful in the invention may be flanked upstream and/or downstream by any number or composition of nucleotides or nucleosides. In some embodiments, the core sequence of a TLR-9 ligand is at least 6 bases or 8 bases in length, and the complete TLR-9 ligand (core sequences plus flanking sequences 5', 3' or both) is usually between 6 bases or 8 bases, and up to about 200 bases in length.

Illustrative DNA-based TLR-9 ligands useful in the invention include, but are not necessarily limited to, poly-nucleotides comprising one or more of the following nucleotide sequences: AGCGCT (SEQ ID NO:49), AGCGCC (SEQ ID NO:50), AGCGTT (SEQ ID NO:51), AGCGTC (SEQ ID NO:52), AACGCT (SEQ ID NO:53), AACGCC (SEQ ID NO:54), AACGTT (SEQ ID NO:55), AACGTC (SEQ ID NO:56), GGCGCT (SEQ ID NO:57), GGCGCC (SEQ ID NO:58), GGCGTT (SEQ ID NO:59), GGCGTC (SEQ ID NO:60), GACGCT (SEQ ID NO:61), GACGCC (SEQ ID NO:62), GACGTT (SEQ ID NO:63), GACGTC (SEQ ID NO:64), GTCGTC (SEQ ID NO:65), GTCGCT (SEQ ID NO:66), GTCGTT (SEQ ID NO:67), GTCGCC (SEQ ID NO:68), ATCGTC (SEQ ID NO:69), ATCGCT (SEQ ID NO:70), ATCGTT (SEQ ID NO:71), ATCGCC (SEQ ID NO:72), TCGTCG (SEQ ID NO:73), and TCGTCGTCG (SEQ ID NO:74).

Additional illustrative TLR-9 ligands useful in the invention include, but are not necessarily limited to, poly-nucleotides comprising one or more of the following nucleotide sequences: TCGXXXX (SEQ ID NO:75, TCGAXXX (SEQ ID NO:76), XTCGXXX (SEQ ID NO:77), XTCGAXX (SEQ ID TCGTCGA (SEQ ID NO:79), TCGACGT (SEQ ID NO:80), TCGAACG (SEQ ID NO:81), TCGAGAT (SEQ ID NO:82), TCGACTC (SEQ ID NO:83), TCGAGCG (SEQ ID NO:84), TCGATTT (SEQ ID NO:85), TCGCTTT (SEQ ID NO:86), TCGGTTT (SEQ ID NO:87), TCGTTTT (SEQ ID NO:88), TCGTCGT (SEQ ID NO:89), ATCGATT (SEQ ID NO:90), TTCGTTT (SEQ ID NO:91), TTCGATT (SEQ ID NO:92), ACGTTCG (SEQ ID NO:93), AACGTTC (SEQ ID NO:94), TGACGTT (SEQ ID NO:95), TGTCGTT (SEQ ID NO:96), TCGXXX (SEQ ID NO:97), TCGAXX (SEQ ID NO:98), TCGTCG (SEQ ID NO:99), AACGTT (SEQ ID NO:100), ATCGAT (SEQ ID NO:101), GTCGTT (SEQ ID NO:102), GACGTT (SEQ ID NO:103), TCGXX (SEQ ID NO:104), TCGAX (SEQ ID NO:105), TCGAT (SEQ ID NO:106), TCGTT (SEQ ID NO:107), TCGTC (SEQ ID NO:108), TCGA (SEQ ID NO:109), TCGT (SEQ ID NO:110), TCGX (SEQ ID NO:111), and TCG (where "X" is any nucleotide).

Illustrative DNA-based TLR-9 ligands useful in the invention include, but are not necessarily limited to, poly-nucleotides comprising the following octameric nucleotide sequences: AGCGCTCG (SEQ ID NO:112), AGCGCCCG (SEQ ID NO:113), AGCGTTCG (SEQ ID NO:114), AGCGTCCG (SEQ ID NO:115), AACGCTCG (SEQ ID NO:116), AACGCCCG (SEQ ID NO:117), AACGTTCG (SEQ ID NO:118), AACGTCCG (SEQ ID NO:119), GACGCTCG (SEQ ID NO:120), GACGCCCG (SEQ ID NO:121), GGCGTTCG (SEQ ID NO:122), GGCGTCCG (SEQ ID NO:123), GACGCTCG (SEQ ID NO:124), GACGCCCG (SEQ ID NO:125), GACGTTCG (SEQ ID NO:126), and GACGTCCG (SEQ ID NO:127).

A TLR-9 ligand useful in carrying out a subject method can comprise one or more of any of the above CpG motifs. For example, a TLR-9 ligand useful in the invention can comprise a single instance or multiple instances (e.g., 2, 4, 5 or more) of the same CpG motif Alternatively, a TLR-9 ligand can comprise multiple CpG motifs (e.g., 2, 3, 5 or more) where at least two of the multiple CpG motifs have different consensus sequences, or where all CpG motifs in the TLR-9 ligand have different consensus sequences.

A TLR-9 ligand useful in the invention may or may not include palindromic regions. If present, a palindrome may extend only to a CpG motif, if present, in the core hexamer or octamer sequence, or may encompass more of the hexamer or octamer sequence as well as flanking nucleotide sequences.

The imidazoquinolinamines imiquimod (see, e.g., FIG. 4) and resiquimod (R-848) (see, e.g., FIG. 5) are commercially available and have been approved for use with humans and in certain embodiments are preferred TLR agonists.

Certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifier The foregoing TLR agonists are intended to be illustrative and not limiting. Using the teachings provided herein other suitable TLR ligands will be recognized by one of skill in the art.

Formulations and Administration.

The immunogenic agents described herein can be administered to a subject alone or in conjunction with one or more immunogenically stimulating adjuvants. In certain embodiments the adjuvant(s) are administered before simultaneously with or after administration of the immunogenic agent(s). In certain embodiments the adjuvant is combined with the immunogenic agent(s) (e.g., KBMA protozoans) in a single formulation or in separate formulations provided together for simultaneous administration. In certain instances, the immunogenic agent (KBMA protozoan) is omitted and the subject is simply treated with a TLR receptor agonist as described herein.

An "immunogenically stimulating adjuvant" designates a compound that is capable of potentiating or stimulating the immune response in a subject animal when administered alone or in combination with the immunogenic agent (e.g., KBMA protozoa) of the invention. Examples of an immunogenically stimulating adjuvant suitable for use in the present invention include, but are not limited to: toll-like receptor agonists, surfactants such as hexadecylamine, octadecylamine, lysolecithin, dimethyl dioctadicyl ammonium bromide, N,N-dioctadecyl-N'—N-bis(2-hydroxyethyl-propane diamine), methoxyhexadecylglycerol, polyoxyethylene-polyoxypropylene block copolymer PLURONIC polyols, saponin, QUIL®A, or the like; polyanions such as pyran, dextran sulfate, polynucleotide complex of polyinosinicpoly-cytidylic acid, polyacrylic acid, carboxypolymethylenes and carboxyvinyl polymers such as CARBOPOL®, aluminum hydroxide, aluminum phosphate, or the like; peptides such as muramyl dipeptide, dimethyl glycine, tuftsin or the like; oil emulsions; immunomodulators such as interleukin-1, interleukin-2, interleukin-12, GM-CSF or the like; or a combination thereof. Certain preferred adjuvants suitable for use in the compositions and methods described herein include toll-like receptor agonists as described herein and/or a a mixture of squalane and a polyoxyethylene-polyoxypropylene block copolymer (e.g., Pluronic® L121, BASF, Parsippany, N.J.) capable of forming small liposomes. In certain embodiments adjuvant may be present formulations of the invention in wt/wt amounts of about 1% to 50%, preferably about 5% to 20%.

The KBMA pathogen (e.g., KBMA protozoan) and/or the TLR agonist can be can be administered directly or as a component of a pharmacological formulation. Similarly, the TLR agonist(s) can be administered alone, or as part of a pharmacological formulation, e.g., a formulation comprising an excipient and/or a KBMA pathogen (e.g., a KBMA protozoan).

The TLR agonist can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents can be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience.

Methods of formulating such derivatives are known to those of skill in the art. For example, of small organic molecules can be prepared from the free base using conventional methodology, that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents described herein, e.g., KBMA protozoan and/or TLR agonist are can be formulated for parenteral, topical, oral, nasal (or otherwise inhaled), rectal, or local administration, such as by aerosol or transdermally, for prophylactic and/or therapeutic treatment for a protozoan infection (or in certain embodiments a bacterial or fungal infection). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

In certain embodiments preferred embodiments, the immunogenic composition can be administered parenterally, for example, intramuscularly, subcutaneously, intraperitoneally, intradermally or the like, preferably intramuscularly; or the composition can be administered orally or intranasally. In certain preferred embodiments, the composition is administered topically, e.g., for prophylaxis or treatment of *Leishmania*.

In various embodiments, the active agents of this invention (e.g., KBMA protozoan and/or TLR agonist(s)) can be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

In certain embodiments pharmacologically acceptable carriers suitable for use in the immunogenic composition of the invention can include any conventional liquid carrier suitable for veterinary pharmaceutical compositions, preferably a balanced salt solution.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In certain embodiments the excipients are sterile and generally free of undesirable matter. These compositions can be sterilized by conventional, well-known sterilization techniques. For various oral dosage form excipients such as tablets and capsules and for topical administration, sterility is not required.

In therapeutic or prophylactic applications, the compositions of this invention are administered, e.g., injected or topically applied, to a subject at risk for or infected with a pathogen (e.g., a protozoan parasite) as described herein in an amount sufficient to induce an immune response thereby reducing or preventing infectivity, and/or pathogenicity, and/or proliferation of the pathogen. Such an amount is defined to be a "immunogenically effective dose". In this use, the precise amount again depends on the subject's state of health and weight, the mode of administration, the nature of the formulation, etc., but generally range from about 0.01 mg to about 500 mg, preferably from about 0.1 mg to about 400 mg or 300 mg, still more preferably from about 0.1 to about 50 mg (e.g., for imiquimod). In certain embodiments doses range from about 0.01 to about 300 mg, preferably from about 0.01 to about 200 mg, more preferably from about 0.01 to about 100 mg (e.g., for resiquimod). Such dosages are similar for topical, and/or subcutaneous administration.

The amount of KBMA pathogen and/or TLR agonist can be adjusted, i.e. increased or decreased, to result in a formulation which provides sufficient protection from infection and/or reduced pathogenicity, and/or reduced proliferation of the desired pathogen.

One typical and illustrative protocol comprises a prime "vaccination" followed by two booster applications, e.g., each step separated by two weeks, three weeks, or one month. In certain embodiments adjuvant TLR agonist creams are administered the day before, and/or the day of, and/or the day after vaccination. In certain embodiments the immunogenic composition is delivered in a 2 or 3 dose regime, for example in a 0, 1 month regime or 0, 1 and 6 month regime respectively. In certain embodiments regime incorporates a booster injection after 3 or 5 to 10 years, preferably 10 years.

The foregoing formulations and administration methods are intended to be illustrative and not limiting. It will be appreciated that, using the teaching provided herein, other suitable formulations and modes of administration can be readily devised.

VI. Kits for Inducing an Immune Response.

In another embodiment this invention provides kits for inducing an immune response (e.g., an immune response directed against a protozoan parasite) in a mammal or a non-mammalian vertebrate as described herein. In various embodiments the kits comprise a container containing a KBMA pathogen (e.g., a KBMA protozoan) and/or a TLR agonist. When both the KBMA pathogen and TLR agonist are present in the kit they can be in separate containers or in the same container (e.g., in a single formulation).

The active agent(s) can be provided in a unit dosage formulation (e.g., suppository, tablet, caplet, patch, etc.) and/or may be optionally combined with one or more pharmaceutically acceptable excipients.

In addition, the kits optionally include labeling and/or instructional materials providing directions (i.e., protocols) for the practice of the methods or use of the immunogenic compositions described herein. Certain preferred instructional materials describe the use of one or more active agent(s) of this invention to induce an immune response in a human, a non-human mammal (e.g., bovine, equine, canine, feline, porcine, bovine, etc.) that inhibits the infectivity and/or pathogenicity, and/or proliferation of a pathogen (e.g., a protozoan parasite). The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Killed but Metabolically Active (KBMA) *Leishmania*—a Novel Protozoan Vaccine Technology for Visceral Leishmaniasis that is Enhanced by Toll-Like Receptor Activation Vaccination with live *Leishmania major* (Leishmanization) is effective against Leishmaniasis but is not acceptably safe. Subunit vaccines are safer, but so far lack efficacy. We describe a whole cell vaccine for experimental murine visceral leishmaniasis that uses *Leishmania chagasi* (LC) treated with the psoralen compound amotosalen (S-59) and low doses of UVA. This treatment generates covalent DNA crosslinks and parasites termed "Killed But Metabolically Active" (KBMA) that retain a complete antigenic repertoire but cannot replicate. KBMA-LC promastigotes can infect murine bone-marrow derived macrophages (BMDM) in vitro, and infect hepatic macrophages in vivo. In BMDMs, KBMA-LC induced nitric oxide production in quantities similar to virulent LC but greater than heat-killed LC, suggesting that KMBA-LC might adequately engage innate immune effectors in a vaccine context. We hypothesized that the toll-like receptor agonists imiquimod (TLR-7) and resiquimod (TLR-7,8) would enhance protective immunity induced by a KBMA-LC vaccine due to the known roles of this pathway in antigen-presenting cell activation, T-reg cell suppression, and host Th1/Th2 balance. Susceptible BALB/c mice vaccinated with KBMA-LC showed protection similar to mice vaccinated subcutaneously with untreated virulent LC when challenged IV with virulent LC (over 40% reduction in liver parasite load compared to controls, $p<0.05$). Mice vaccinated with the combination of KBMA-LC and topically applied TLR agonist showed marked additional protection—68% for imiquimod ($p<0.0001$). Resiquimod, a more potent TLR agonist with enhanced TLR-8 activity, shows potential for profound protection against *leishmania* challenge. We present a novel vaccine model against intracellular protozoans that maintains the immunogenicity of live cells with the safety of killed cells, and we provide data that support the combinatorial use of TLR agonists. This technology could be used in therapeutic vaccines, in combination with other genetic alterations in *Leishmania*, or with other protozoan parasites.

Example 2

In various embodiments we propose the use of KBMA *Leishmania chagasi* (KBMA-LC), KBMA *Leishmania major* (KBMA-LM), and KBMA *Plasmodium berghei* (KBMA-PB) as whole cell vaccines that combine the potential for protective efficacy of live whole cell vaccines with the potential safety of inactivated vaccines. Our data demonstrate that KBMA-LC showed progressive but non-immediate death and non-detectable metabolic activity within 21 days as measured by a luciferase assay (FIG. 6A). Nevertheless, KBMA-LC romastigotes prepared in this manner can infect murine bone marrow derived macrophages (BMDM) in vitro (FIG. 6B), and infect hepatic cells in vivo (not shown). In the murine BMDMs, KBMA-LC induced nitric oxide production in quantities similar to virulent LC but greater than heat-killed LC (FIG. 6C), suggesting that KMBA-LC can adequately engage innate immune effectors.

Innate Immunity and Toll-Like Receptor Agonists as Vaccine Adjuvants:

Cells of the innate immune system recognize conserved components of microbial pathogens via cell surface receptors such as Toll-like receptors (TLRs). Activation of TLRs leads to inflammatory cytokine production and antimicrobial immune responses by innate immune cells—macrophages and dendritic cells (DC).

Lipophosphoglycan (LPG) on *Leishmania* cell surface has been implicated as an agonist of TLR-2. In malaria, *Plasmodium* blood stage parasite degrade host hemoglobin into hemozoin, which is associated with TLR-9 activation and disease pathogenesis. In general, stimulation of TLRs ultimately results in gene expression profiles that lead to the production of Type I cytokines. Mice defective in the TLR signaling are highly susceptible to *Leishmania* infection, directly implicating TLRs in anti-leishmanial immunity. Imiquimod is an immunomodulatory, small-molecule compound in the imidazoquinoline family that displays both anti-viral and anti-tumor effects. Imiquimod has primarily TLR-7 activity in mice and in humans. Approved for the treatment of genital warts and actinic keratoses, imiquimod has been used clinically for an increasingly wide range of infectious and neoplastic skin disorders. Topical treatment with imiquimod induces a variety of pro-inflammatory cytokines and facilitates the maturation and migratory capabilities of DCs.

Resiquimod is a potent congener imidazoquiioline that also activates human and murine TLR-7 and also human (but not murine) TLR-8. Lastly, in the setting of established tolerance, recent evidence suggests that persistent TLR signaling is required for bypassing regulatory T cell-induced tolerance. Regulatory T cells (Tregs) have been shown to have important and complex roles in *Leishmania* immunity, rendering the skin an area for immune privilege and thus a reservoir for recurring infection.

We explored the use of topical TLR-7/8 agonists as an adjuvant to whole cell *Leishmania* and *Plasmodium* vaccines due to their properties as activators of antigen presenting cells, their propensity to redirect immune responses to Th1 over Th2 phenotype, and their potential modulating effects on regulatory T cells.

Proof-of-Concept in Mouse Model of Visceral Leishmaniasis.

To determine of the KBMA *Leishmania* vaccine alone or in combination with TLR agonist adjuvants could protect mice from future virulent *Leishmania* challenge, we performed a pilot vaccine/challenge experiment in susceptible BALB/c mice. Animals vaccinated with KBMA-LC showed protection similar to mice vaccinated subcutaneously with untreated virulent LC when challenged IV with virulent LC (over 40% reduction in liver parasite load compared to controls, $p<0.05$), (FIG. 7). Mice vaccinated with the combination of subcutaneous KBMA-LC and topically applied TLR agonists showed marked additional protection—68% for imiquimod ($p<0.0001$) and 87% for resiquimod ($p<0.00005$). Two of 8 animals in the latter group showed complete protection from liver infection. In a subsequent experiment (data not shown), mice given resiquimod alone (i.e. without parasites) showed significant protection as well. This finding highlights the potency of topical TLR agonists as general immune system stimulators. The combinatorial effect of imiquimod and KBMA-LC was confirmed in the subsequent trial as well.

Example 3

Killed But Metabolically Active *Leishmania*—is a Novel Whole Cell Vaccine for Visceral Leishmaniasis and is Enhanced by Toll-Like Receptor 7 Activation Besides malaria, visceral leishmaniasis is the second most deadly parasitic infection worldwide. No vaccines are currently in widespread clinical use. Sub-unit and killed whole-cell vaccines for leishmaniasis have been ineffective, and live vaccines are not acceptably safe. We describe a novel whole-cell vaccine approach that uses *Leishmania* chagasi (LC) promastigotes treated with the psoralen compound amotosalen and low doses of ultraviolet A radiation. This treatment generates permanent covalent DNA crosslinks within parasites subsequently termed Killed But Metabolically Active (KBMA). KBMA-LC are able to invade macrophages and generate protective immune responses in mice similar to live vaccination. However, they are replication defective and thus safe for use as a protective vaccine. We also demonstrate that vaccine-induced protection by KBMA-LC is enhanced by imiquimod, an artificial agonist of Toll-like receptor 7 (TLR7), when applied as a topical vaccine adjuvant. The improved vaccine response is associated with an enhanced anti-*leishmania* Th1-type CD4 T cell response. These results suggest that KBMA technology is a potentially safe and effective novel vaccine strategy against the intracellular protozoan *L. chagasi* and represents a new method for whole cell vaccination against other complex intracellular pathogens.

Methods.

Animals.

6-8 week old female Balb/C mice (Jackson Laboratories) were used for studies throughout. Mice were maintained in the Biological Resource Center of the Los Angeles Biomedical Research Institute under humane conditions and were fed pelleted chow and water ad libitum.

Parasites

The *L. chagasi* strain (MHOM/BR/00/1669), originally isolated from a patient with visceral leishmaniasis in Northeast Brazil, was maintained by serial intracardiac injection in outbred male golden hamsters. Virulent amastigotes were isolated from hamster spleens removed from animals infected approximately 3 months prior to sacrifice. Promastigotes were cultured in hemoflagellate minimal essential medium (HOMEM) at 26° C. and were used for vaccination or challenge within one month of harvest from the hamsters. Killed But Metabolically Active (KBMA) promastigotes were prepared by incubating late-log or stationary phase organisms in amotosalen (S-59) 100 nM for one hour while shaking at room temperature, followed by cross-linking of DNA using UVA irradiation of aliquots of 2 ml of cells in 6 well plates in an Intercept Illuminator (Cerus Corporation). Radiation dose was 5.4 J/cm$^2$. Heat-killed organisms were prepared by incubating in a 100° C. bath for 10 minutes. Transgenic firefly luciferase expressing *L. chagasi* and *L. major* were kindly provided by Dr. Beverley. For CFSE-based flow cytometry experiments, promastigotes were stained with CFSE at 5 μM and, shaken at 37° C. for 10 minutes. Parasites were washed three times with PBS and then cultured at an initial concentration of 5×106 per ml in HOMEM for in vitro experiments or injected into mice in 200 μL, of PBS at a concentration of 5×10$^8$ per ml.

In Vitro Luciferase Assays

Serial measures of parasite luciferase activity were made using a Sirius Single Tube Luminometer (Berthold Detection Systems). Aliquots of cultured organisms were taken daily and combined with 5× reporter lysis buffer per the manufacturer's instructions, and frozen at −80° C. All samples were then snap-thawed at 37° C. on the day of assay. 50 μl samples from each aliquot were combined with 100 μl of luciferin and luminescence was quantified with the luminometer in relative luminsescence units (RLU).

Flow Cytometry and Intracellular Cytokine Staining

At indicated time points, CFSE stained parasites were sampled from culture flasks, centrifuged at 2000 g and stored at 4° C. in 2% paraformaldehyde. All samples were analyzed on the same day on a Facscalibur (Becton-Dickinson) flow cytometer. CFSE fluorescence was registered on channel FL-1. Intracellular staining of CD4 and CD8 lymphocytes from vaccinated animal spleens were performed in the same instrument. Cells harvested from immunized animals' spleens were subjected to red blood cell lysis using Pharmlyse (Becton-Dickinson) and then cultured in complete RMPI for 72 hours in the presence of 50 units/ml recombinant human IL-2 and medium-only control or 3×10$^6$ live LC promastigotes as an antigenic stimulant. In the final six hours of culture, media and promastigotes were replaced at identical concentrations but now supplemented with 1 μl/ml Brefeldin A (Golgi Plug—Becton Dickinson). These cells were surface-stained with PE-conjugated antibodies to CD4 and CD8, fixed, permeabilized (Becto-Dickinson Cytofix/Cytoperm Plus) and stained with fluorochrome-conjugated antibody to interferon-γ, and analyzed by flow cytometry.

In Vitro Macrophage Invasion.

In vitro macrophage invasion experiments were performed using murine bone marrow derived macrophages prepared by plating primary 2.5×10$^5$ per ml BALB/c bone marrow cells in 1 ml bone marrow conditioning medium (Complete DME with 30% L-cell conditioned medium) for one week in 12 well plates containing sterile circular cover slips. Live-LC, KBMA-LC, or Heat-Killed-LC promastigotes at a multiplicity of infection of 20 (i.e 5×10$^6$ organisms) were coincubated with BMDMs for one hour to allow for infection before washing. Cells were then incubated for 48 hours at 37° C. and 5% $CO_2$ before cover slips were removed, Giemsa stained, mounted, and parasite infection scored by a blinded microscopist. Results are representative of triplicate wells.

Nitric Oxide Secretion.

Macrophage killing function as measured by induction of nitric oxide production was determined by infecting BMDM with as described above with Live-LC, KBMA-LC, or Heat-Killed-LC promastigotes or PBS as a control in complete DME supplemented with 10 μ/ml recombinant murine IFN-γ. Supernatants were sampled and assayed for nitrite ion, which is proportionate to nitric oxide production, by the Griess method. Samples were analyzed by absorbance photometry at a wavelength of 535 nm and nitrite ion concentration calculated by comparison with a standard curve of serial dilutions of sodium nitrite.

In Vivo Assay of Mouse Hepatocyte Invasion.

CFSE labeled parasites were injected intravenously via the tail vein into BALB/c mice. Twenty-four hours to 72 hours later, animals were sacrificed and livers were dissected. Invasion was measured by flow cytometry of single cell suspensions of liver cells on a Facscalibur (Becton Dickinson) flow cytometer.

Mouse Immunization, Adjuvant Toll-Like Receptor (TLR) Agonist Administration and Challenge.

On the day prior to each vaccination, mice were anesthetized by intraperitoneal injection of 0.2 ml a solution of ketamine 9.1 mg/ml and xylazine 0.73 mg/ml. A 2×3 cm patch of fur in the dorsal cervical area was shaved, and 50 mg of adjuvant cream—either imiquimod 5% cream or appropriate vehicle (3M Pharmaceuticals)—was applied topically to the shaved area. On the day of immunization, mice were anesthetized as above. Unfractionated late-log to stationary phase promastigotes (live or KBMA) were spun at 2000 g for 10 minutes, resuspended in PBS, counted on a Neubauer hemocytometer, and volume-adjusted to a final concentration of 10$^8$ organisms/ml. One hundred micoliters of the appropriate parasite suspension (10$^7$ organisms) or 100 μl of PBS for controls was subcutaneously injected into the dorsal-cervical area of anesthetized mice using a 28-gauge needle. Adjuvant cream was then applied at the shaved skin site as above. On the day after immunization, adjuvant cream was once again applied topically as above on unanesthetized mice. For each experiment, mice were immunized three times at two-week intervals. Two weeks after the final immunization, mice were challenged by intravenous injection with $10^7$ unfractionated late-log to stationary phase promastigotes in 0.2 ml of PBS.

Assessment of Vaccine Protection.

Vaccinated mice were sacrificed by $CO_2$ inhalation 4 weeks after intravenous challenge. Livers and spleens were weighed. Impression smears on glass slides were made from dissected spleen and liver tissue and were then methanol-fixed and amastigotes were detected with Giemsa stain. Organ parasite load was scored by direct microscopy and rendered in Leishman-Donavan Units (LDU), defined as number of parasites divided by number of mammalian cells multiplied by the organ mass in milligrams. At least 500 mammalian cells or 500 parasites were counted by a scorer blinded to the vaccination groups.

Statistical Methods

Experiments with 3 or fewer groups were analyzed by two-tailed T-tests. Experiments with 4 or more groups were analyzed by single factor or two factor ANOVA using NCSS 2001 software. Unless stated otherwise, a P Value of <0.05 was considered significant. In experiments with multiple comparisons between groups (n), the Bonferroni correction—0.05/n—was applied to interpretation of P values to minimize type I error generated by a multiplicity of hypotheses.

Results.

Figure 8A:
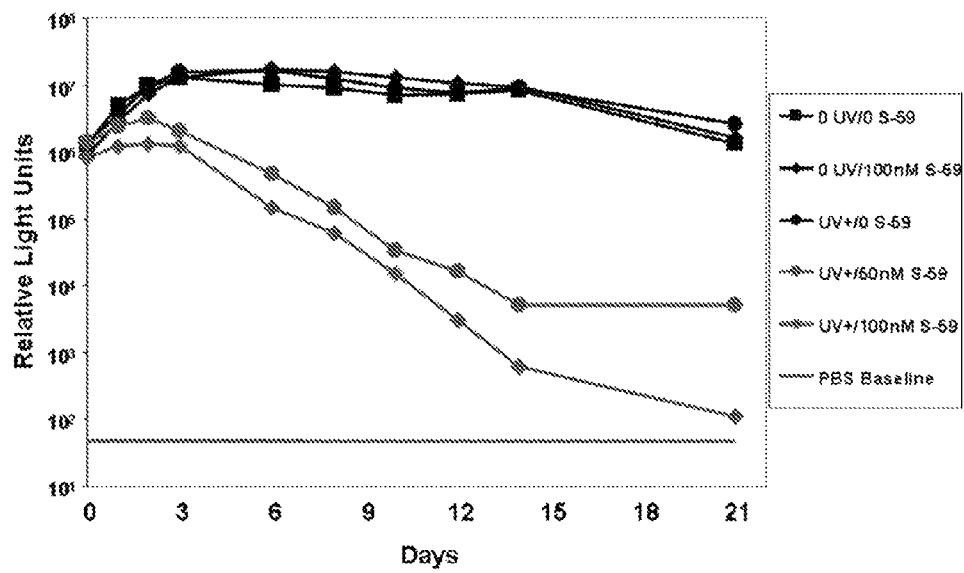
Figure 8B:
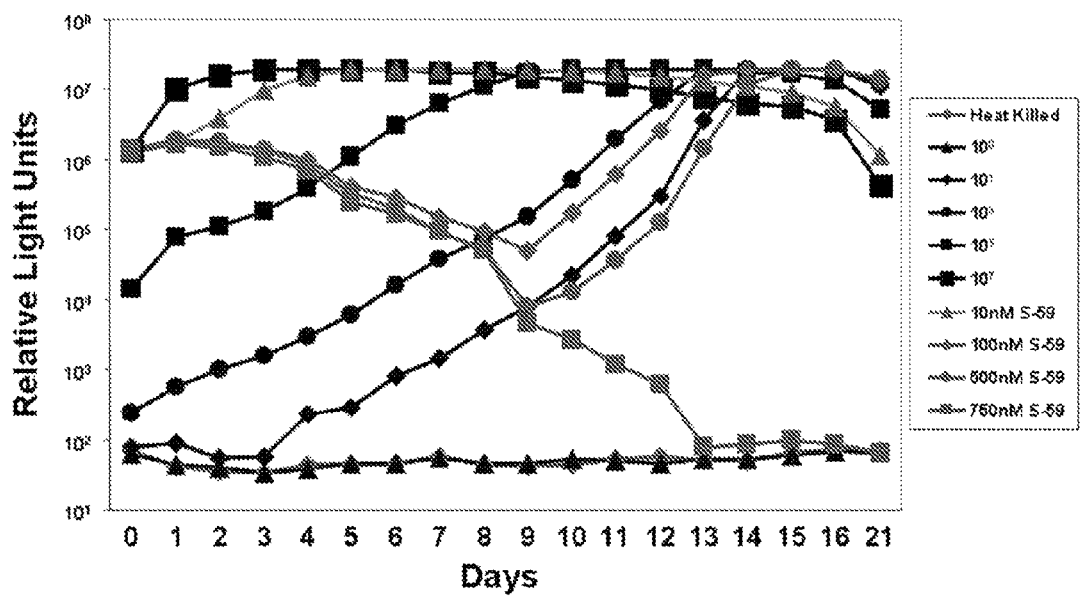
Figure 8C:
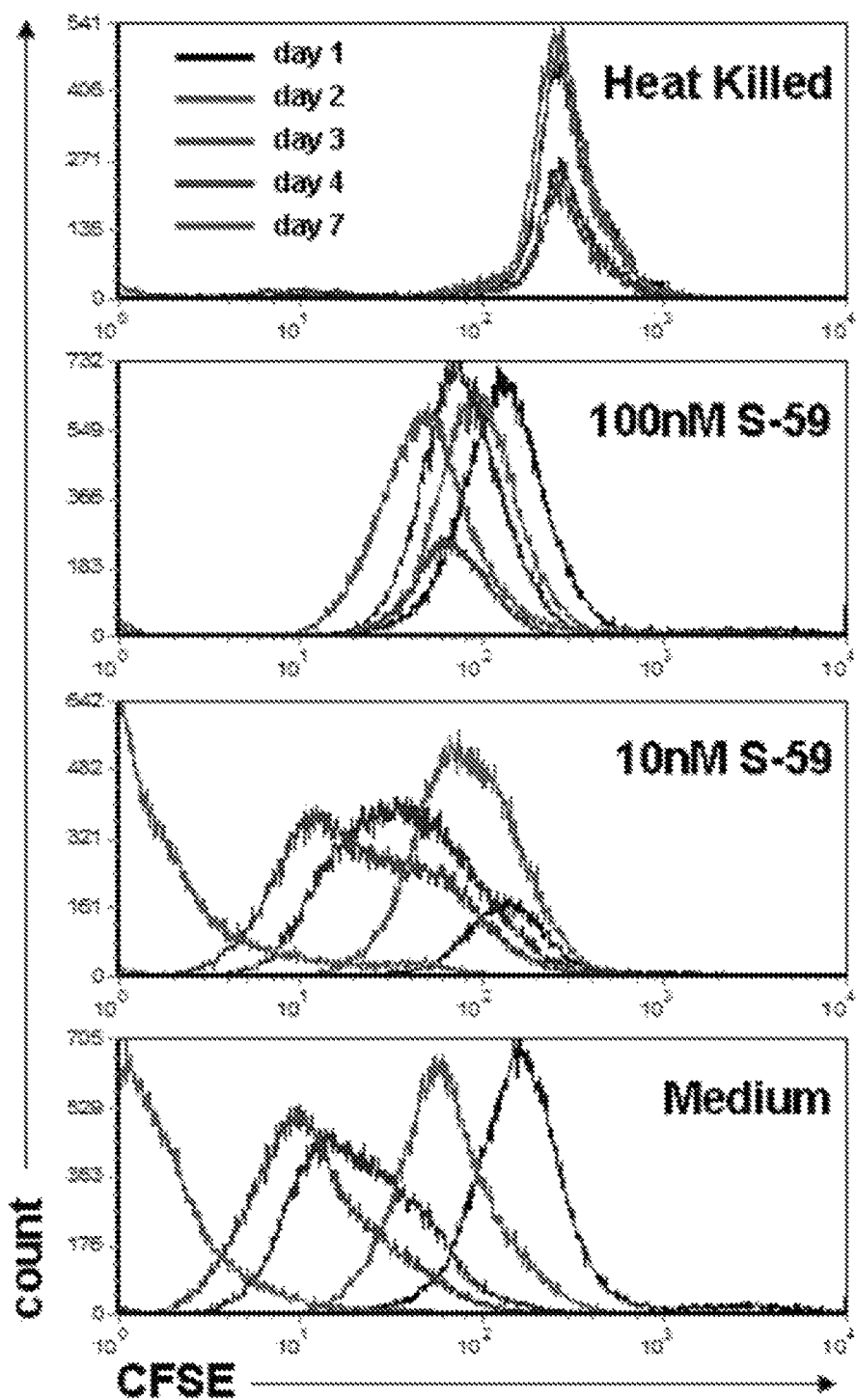
Figure 8D:
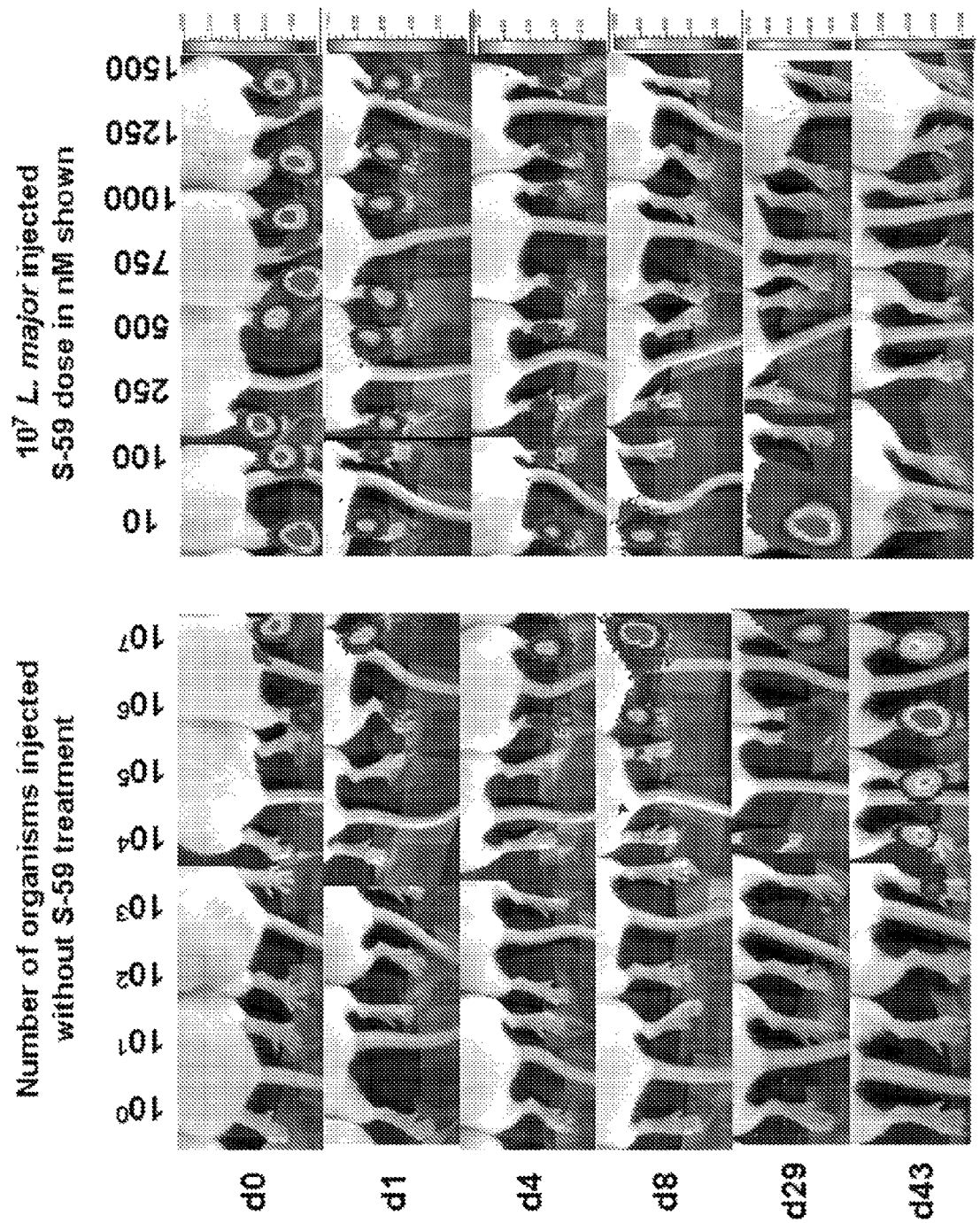

*Leishmania* are Rendered Killed but Metabolically Active (KBMA) by the Psoralen S-59 (amotosalen) and UVA Light A mouse visceral leishmaniasis model employing *Leishmania chagasi* expressing firefly luciferase was used to test the susceptibility of a eukaryotic pathogen to in vitro inactivation?). *L. chagasi* were treated with varying doses of S-59 for 1 hour and then exposed to 5.4 J/cm2 UVA using a commercial illuminator which delivers tightly metered UVA doses to a shaking flask of organisms. This UVA dose was determined based on prior experience with *Listeria*. After irradiation with UVA, parasites were kept in culture and assayed at various time points for luciferase expression as a measure of metabolic activity. Dose-response curves demonstrate that KBMA-LC, prepared with a dose of 100 nM S-59 and 5.4 Joules/cm$^2$ of UVA, showed progressive but non-immediate death and non-detectable metabolic activity within 21 days as measured by a luciferase assay (FIG. 8A). Parallel experiments monitoring absolute parasite number and detectable parasite mobility reflected a similar pattern of declining activity (not shown). Higher doses of S-59 led to more rapid decline in luciferase activity and doses lower than 50 nM led to breakthrough outgrowth of parasites (data not shown). To determine if this technology would be applicable to another species of *Leishmania*, we tested the ability of S-59 and UVA to render *Leishmania major* KBMA. *L. major* showed a similar pattern of susceptibility to inactivation in this manner (FIG. 8B). We hypothesized that in addition to a progressive decline in metabolic activity, S-59 plus UVA treatment would inhibit parasite mitosis by creating permanent covalent DNA crosslinks as was demonstrated in *Listeria*. To determine if the S-59 induced decline in luciferase activity was associated with an inability to replicate, live *L. chagasi* promastigotes were stained with the intracellular dye CFSE and monitored for 1 week in culture. Untreated CFSE-stained promastigotes showed progressive diminution of "per parasite fluorescence" associated with a dividing microorganism, while promastigotes treated with 100 nm S-59 and 5.4 Joules/cm$^2$ of UVA and stained with CFSE showed no such diminution (FIG. 8C). These findings, together with the luciferase expression data above, demonstrate that these S-59 and UVA doses result in *Leishmania* promastigotes that can not divide, but maintain significant levels of metabolic activity during the first two weeks after treatment. All detectable metabolic activity in $10^7$ promastigotes was abolished by 3 weeks under these conditions. The combination of 100 nM S-59 and 5.4 Joules/cm$^2$ was used for subsequent studies. To test the ability of S-59 to inhibit growth of parasites in vivo, similar experiments were performed, but treated parasites were instead injected into mouse footpads and measured over 6 weeks. The size of the parasitic infection in each foot is measured (FIG. 8D).

KBMA-LC Invade Macrophages and Induce them to Produce Nitric Oxide.

Figure 9A:
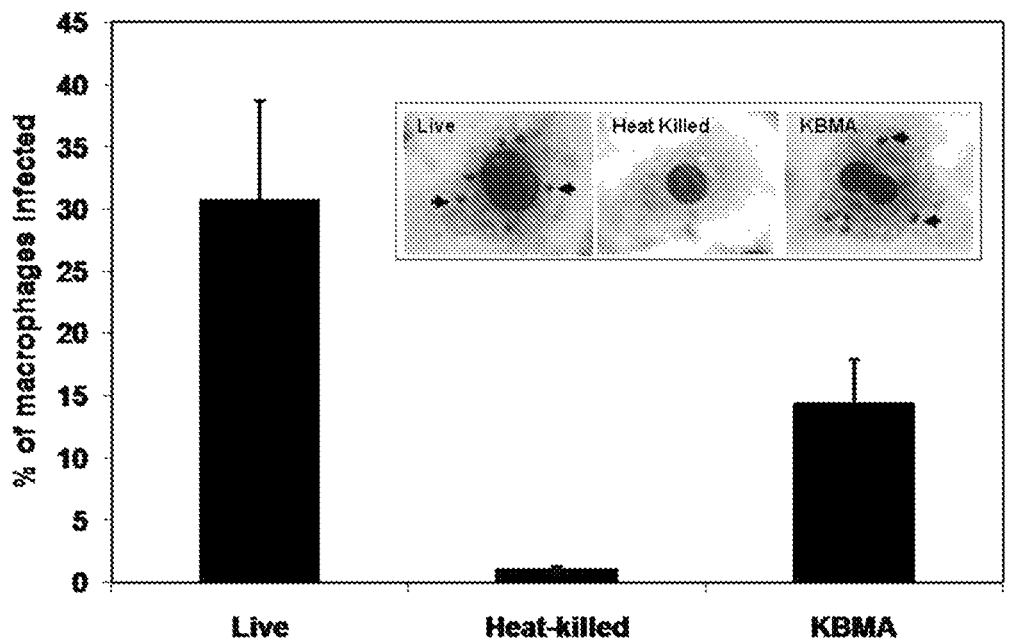

During normal infections in animal models and in humans, *Leishmania* spp invade macrophages and killing is achieved through nitric oxide (NO) secretion. Invasion of macrophages may be required for ultimate antigen presentation to T cells and is likely involved in persistent infections required for long term immunity. *Leishmania* invasion of macrophages can be detected both in vivo and in vitro. To determine if KBMA-LC are able to infect macrophages, freshly isolated murine bone marrow-derived macrophages from BALB/c mice were exposed to KBMA-LC for 1 hour, and then washed to remove non-infecting parasites. Intracellular amastigotes were scored by light microscopy 48 hours after infection. KBMA-LC promastigotes infected murine bone marrow-derived macrophages (BMDM) in vitro (FIG. 9A) as do untreated live-LC. This is in contrast to heat-killed parasites which were not phagocytosed by BMDM.

Figure 9B:
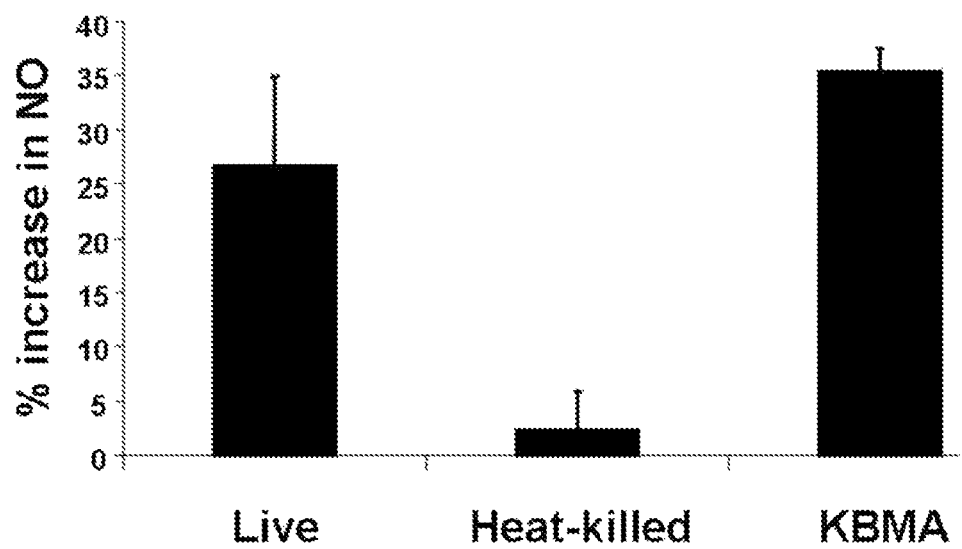

*Leishmania* infection of macrophages normally induces nitric oxide synthase (iNOS) and results in NO secretion in the presence of IFN-γ. To determine if KBMA-LC is capable of inducing NO secretion, NO levels were measured in the media of BMDM cultures 48 hours after infection with either live-LC, KBMA-LC or heat-killed-LC promastigotes. In murine BMDM, KBMA-LC induced NO production in quantities similar to live LC but greater than heat-killed-LC (FIG. 9B). These finding indicate that KMBA-LC can adequately engage innate immune effectors and can function as a more efficacious vaccine than heat-killed organisms.

Figure 9C:
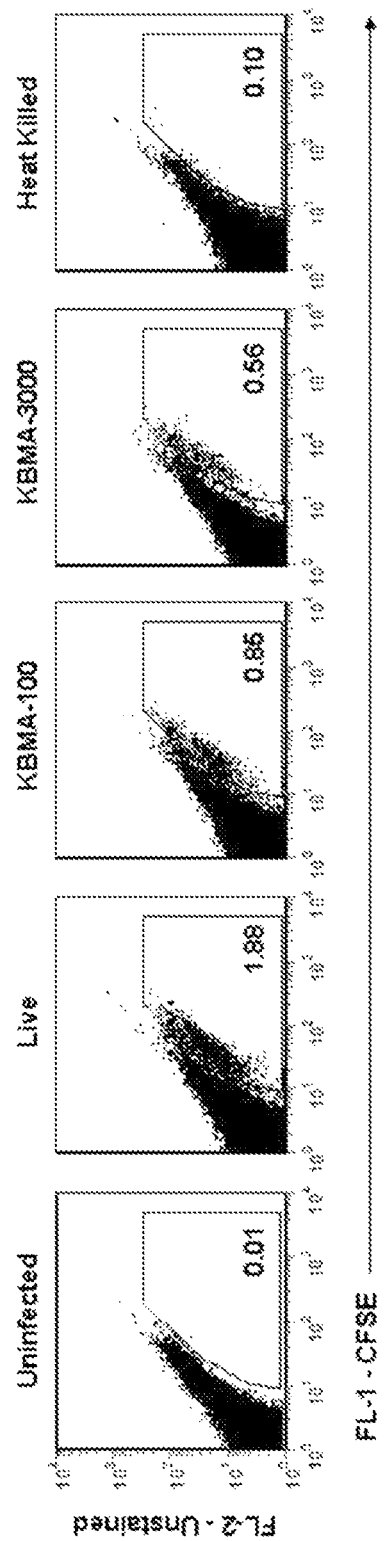
Figure 9D:
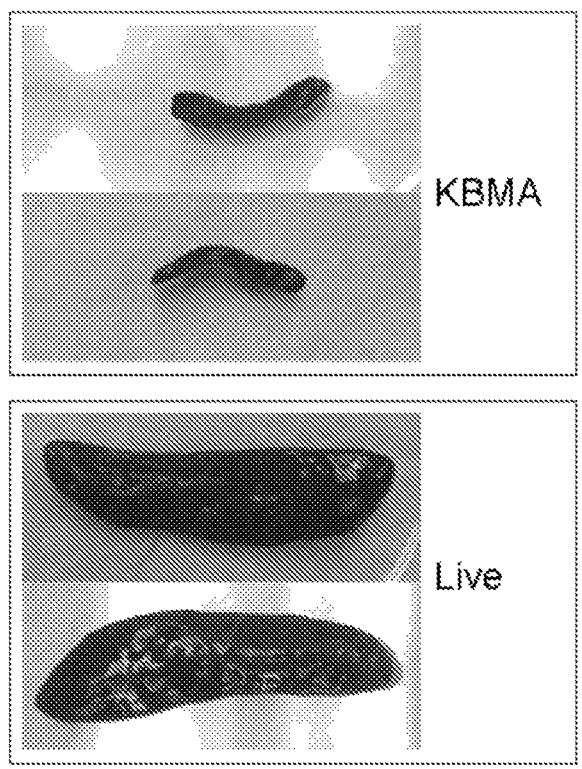

KBMA-LC Invade Liver Cells In Vivo within 24 Hours but Cause No Long Term Disease To determine if KBMA-LC were capable of infecting macrophages in vivo, treated promastigotes were stained with CFSE and injected intravenously into BALB/c mice via the tail vein. 24-72 hours later, livers were removed and cell suspensions prepared for flow cytometry. CFSE-stained KBMA-LC and CFSE-stained live *L. chagasi* could be detected in the livers of mice after 24 hours, but heat-killed organisms could not be detected (FIG. 9C). Similar results were detected at 72 hours (date not shown). This demonstrates that the in vivo biological activity of KBMA-LC is maintained for at least 72 hours, and that these organisms are capable of invading target cells. To test the relative safety of KBMA-LC compared to live-LC promastigotes, we intravenously infected BALB/c female mice with $10^7$ KBMA-LC or with untreated live-LC. Six months after infection, all mice infected with live-LC showed splenomegaly, but none of the KBMA-LC infected mice showed any sign of disease (mean spleen mass 0.584+/−0.011 g versus 0.074+/−0.002 g, P<0.0005, n=5 mice per group) and hepatomegaly (mean liver mass 1.62+/−0.06 g versus 1.16+/−0.05 g, P<0.000005). Light microscopy showed spleen and liver parasite loads of 99.6+/−SE 25.2 and 128.6+/−SE 30.1 Leishman-Donovan Units (LDU) in live-LC infected mice but no remaining parasites in any of the five mice infected with KBMA-LC. FIG. 9D shows representative spleens from this experiment. Thus, like live-LC, KBMA-LC can be recovered from animal organs up to 3 days after infection, but unlike live-LC, KBMA-LC are absent 6 months after infection, and KBMA-LC infected animals show no signs of associated hepatosplenomegaly or parasitosis six months after infection.

KBMA-LC and the TLR-7 Agonist Imiquimod Protect Mice from Virulent Infection

Figure 10A:
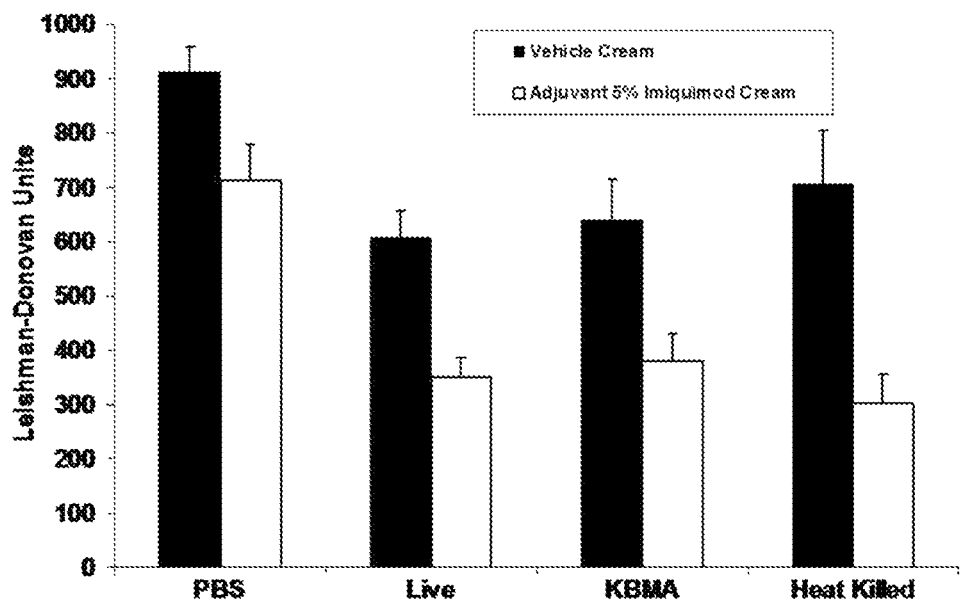
Figure 10B:
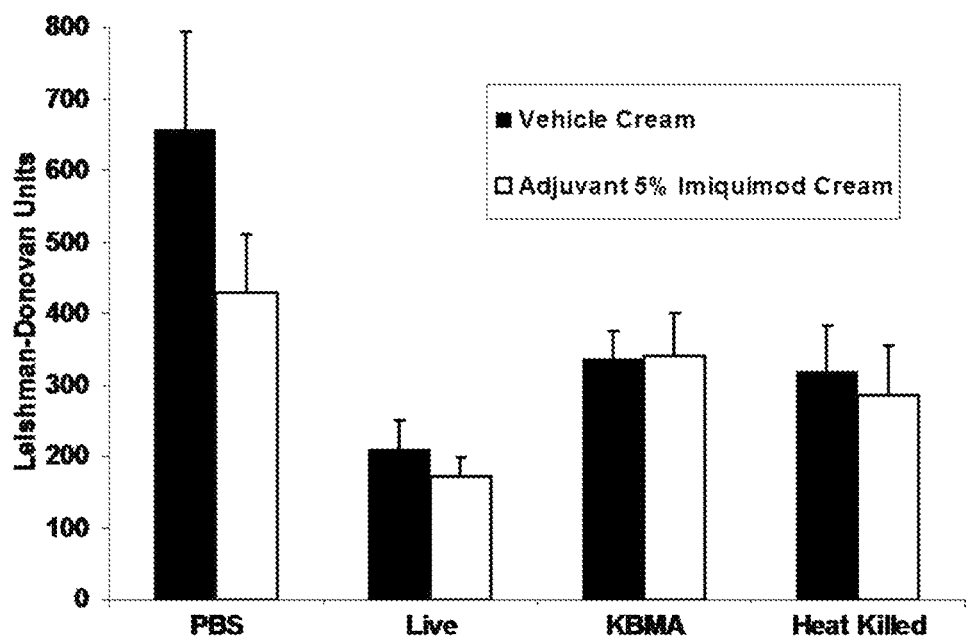

To determine efficacy of the KBMA-Leishmania vaccine alone or in combination with TLR agonist adjuvants, we performed vaccine/challenge experiment in susceptible BALB/c mice. High dose live virulent *L. chagasi* injected subcutaneously in the dorsal neck has previously been shown to partially protect mice against subsequent *L. chagasi* intravenous challenge. In the current studies, animals were vaccinated with either high-dose live LC, KBMA-LC, heat-killed-LC, or phosphate buffered saline as a control. Groups were divided into subgroups that received adjuvant topical 5% imiquimod cream or a vehicle control at the site of vaccination on the skin on the day before, day of, and day after the primary vaccination. Animals were boosted twice (as above) at 2 week intervals and challenged 2 weeks after the final immunization. Animals vaccinated with KBMA-LC and showed protection similar to mice vaccinated with virulent LC (about 30% reduction in liver parasite load compared to PBS controls, P<0.001), (FIG. 10A). Surprisingly, heat-killed LC also showed a strong trend towards protection (P=0.013). Mice in each vaccination group showed additional protection in the groups receiving adjuvant imiquimod cream when compared to the control vehicle cream (FIG. 10B).

Whole Cell KBMA-LC Vaccination Induces Adaptive Immune Responses, which are Enhanced and Shifted Toward Th1 by the TLR-7 Agonist Imiquimod.

Figure 11A:
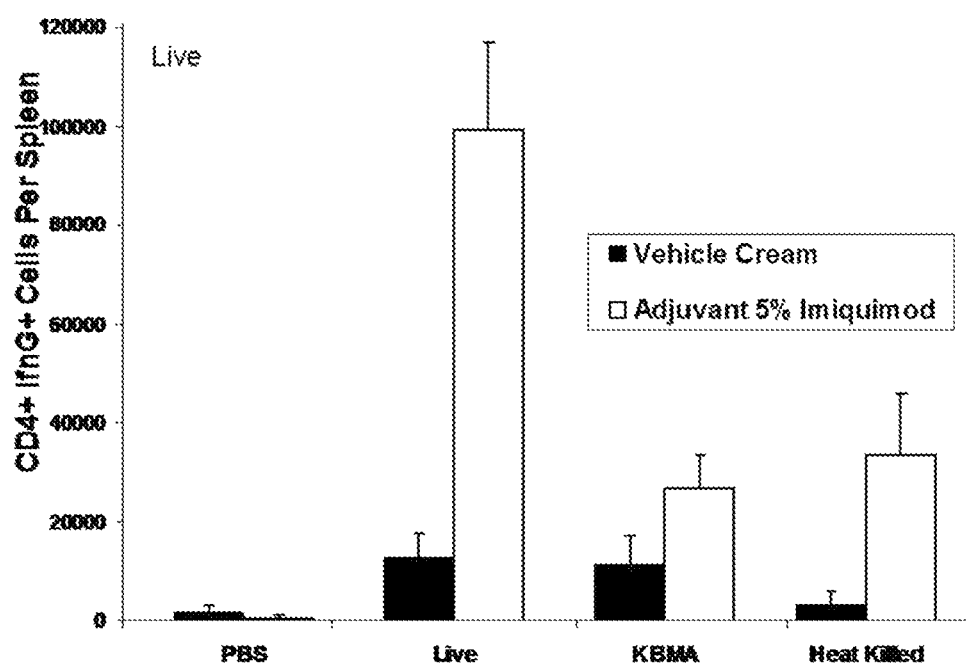
FIG. 11C: Luminex quantitation of cytokine production in splenocytes from *L. chagasi* immunized BALB/c mice with or without adjuvant 5% imiquimod. Mice were immunized three times at two week as in FIG. 10. Two weeks after the final vaccination, animals were sacrificed and $10^6$ splenocytes from each were cultured for 66 hours in either in the presence of live *L. chagasi*. Supernatants from these cultures were frozen and then subsequently thawed and analyzed by the luminex method using antibodies and antibody coated beads specific for the indicated cyotokines. Bars show concentration of the relevant cytokine in pg/ml+/−SEM.
Figure 11B:
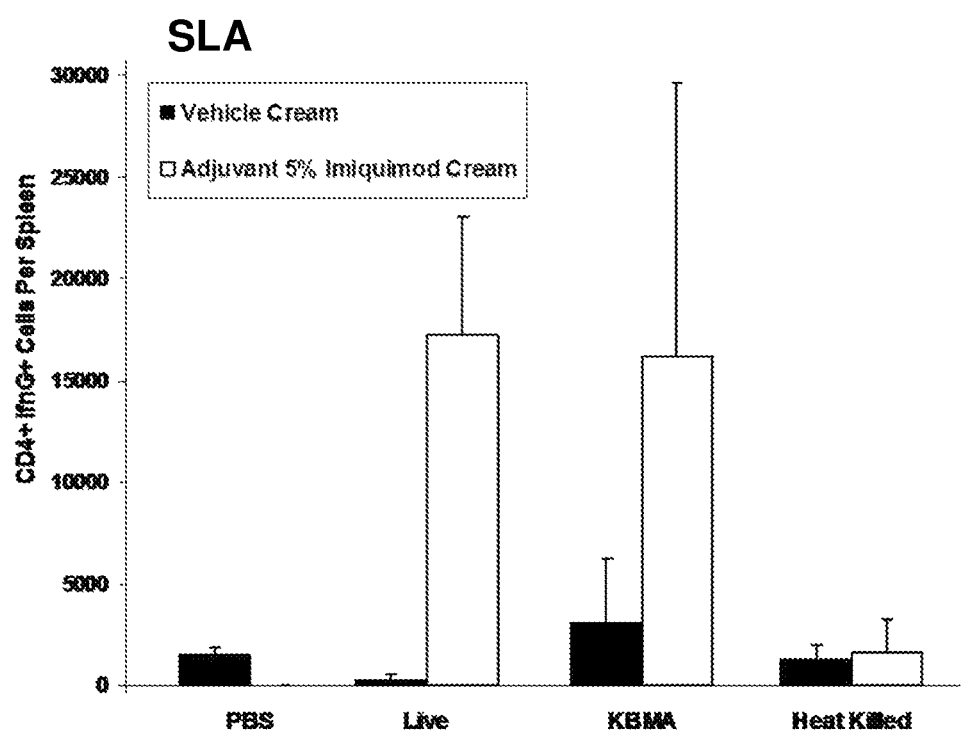
Figure 11C:
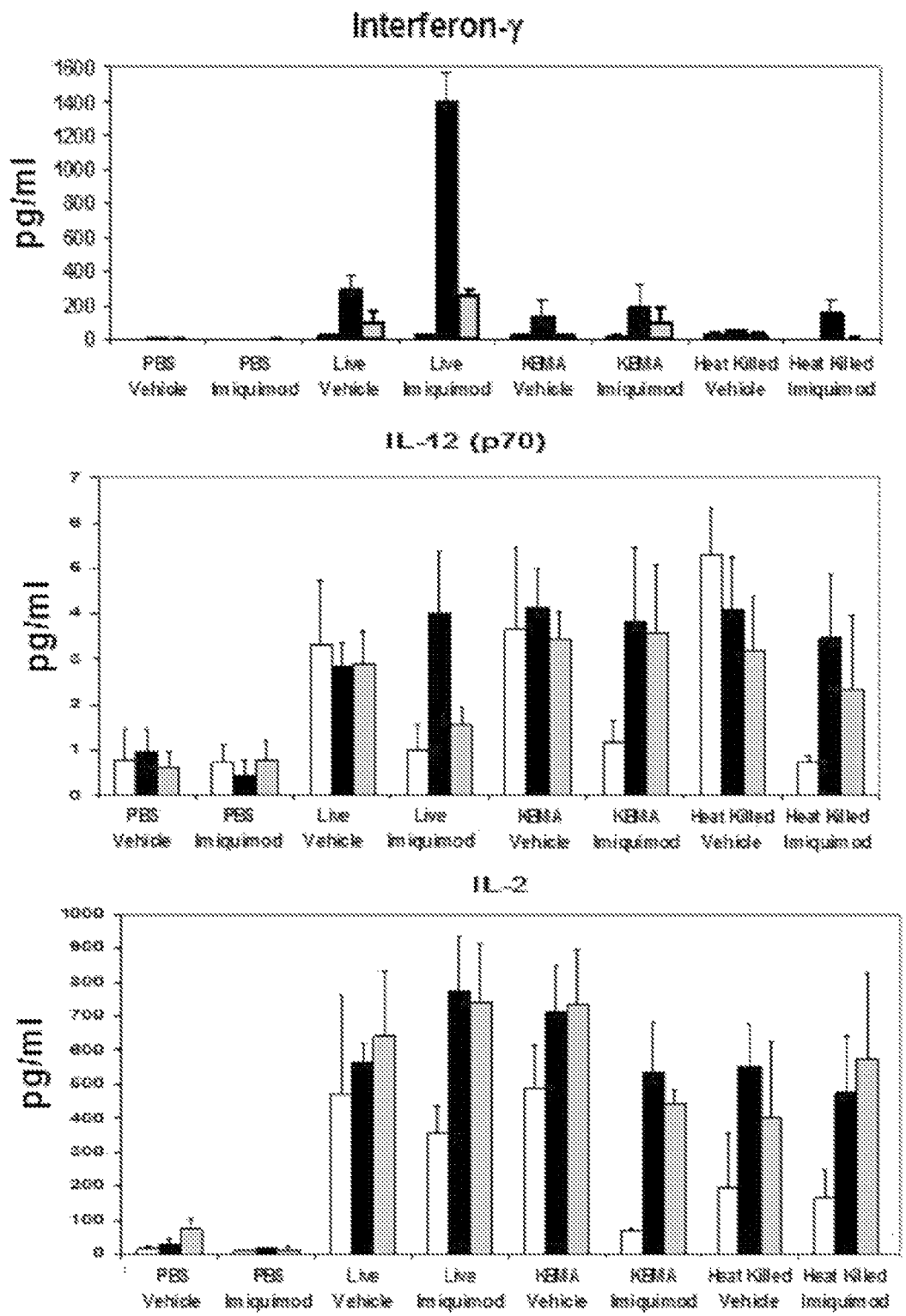

The trend towards a protective effect in mice that received only the adjuvant imiquimod 5% suggests that the TLR agonist works in part by non-specific activation of innate immune cells. To address whether treatment with imiquimod leads to a detectable adaptive immune response in vaccinated mice, we conducted parallel immunological experiments to look for antigen specific T-lymphocytes in the spleens of a vaccinated animals. Two weeks after completing a vaccination regime identical to that described above, groups of mice were sacrificed and the antigen specificity of splenic T cells was analyzed by flow cytometry to detect intracellular IFN-γ. Live-LC (3 of 3 animals), KBMA-LC (2 of 3 animals), and heat-killed LC (1 of 3 animals) demonstrate antigen stimulated CD4+ T cell responses that were enhanced by adjuvant imiquimod (FIGS. 11A, 11B). Thus, TLR activation in this vaccine context enhances adaptive immunity that correlates with anti-*leishmania* protection. No CD8+ T cell responses were detected (data not shown). In a parallel experiment, groups of mice were vaccinated and boosted twice as described above. Splenocytes were harvested from these animals 2 weeks after the third vaccination. Splenocytes were then stimulated with either live LC promastigotes or soluble *L. chagasi* antigen (SLA) for 66 hours in culture and supernatants were harvested. Splenocytes from animals vaccinated with whole cell LC vaccines—live, KBMA, or heat-killed showed elevated cytokine responses not seen in splenocytes taken from PBS vaccinated animals (FIG. 11C). Mice vaccinated with PBS and adjuvant imiquimod 5% showed no increase in cytokine production when compared to mice vaccinated with PBS and a vehicle control adjuvant. However, splenocytes from mice vaccinated with whole cell vaccines and adjuvant imiquimod 5% showed a pattern of cytokine expression that includes increased IFN-γ but decreased IL-10, IL-4, and IL-5 when compared to animals vaccinated with whole cell vaccines and vehicle control adjuvant. The pattern of increased IFN-γ and decreased IL-10, IL-4, and IL-5 correlated with the groups that showed best protection in the animal protection experiments. This pattern is associated with a Th1 type immune response that has previously been reported as characteristic of TLR-7 activation and as favorable protection in animal and human vaccine trials against intracellular organisms.

TABLE 4

KL2-3 ANOVA P values. Summary of P values determined by single factor ANOVA corresponding to differences between indicated groups in vaccine protection experiments from FIG. 10. Starting with an initial tolerance for a type 1 error of <5% (i.e. $P < 0.05$), the Bonferroni calculation for these 16 informative comparisons led us to consider differences with a corresponding P value of less than 0.003125 to be significant.

|  | Live Imiquod | Live Vehicle | PBS Imiquod | PBS Vehicle | KBMA Imiquod | KBMA Vehicle | HK Imiquod | HK Vehicle |
|---|---|---|---|---|---|---|---|---|
| Live Imiquod | x | 0.00116 | 0.000008 |  | 0.679456 |  | 0.500543 |  |
| Live Vehicle |  | x |  | 0.000135 |  | 0.065941 |  | 0.579393 |
| PBS Imiquod |  |  | x | 0.01093 | 0.000039 |  | 0.000016 |  |
| PBS Vehicle |  |  |  | x |  | 0.000636 |  | 0.012643 |
| KBMA Imiquod |  |  |  |  | x | 0.001061 | 0.312787 |  |
| KBMA Vehicle |  |  |  |  |  | x |  | 0.833161 |
| HK Imiquod |  |  |  |  |  |  | x | 0.001185 |
| HK Vehicle |  |  |  |  |  |  |  | x |

TABLE 5

Summary of P values determined by single factor ANOVA corresponding to differences between indicated groups in flow cytometry experiment from FIG. 11C. Starting with an initial tolerance for a type 1 error of <5% (i.e. $P < 0.05$), the Bonferroni calculation for these 16 informative comparisons led us to consider differences with a corresponding P value of less than 0.0031 to be significant. By two factor ANOVA (i.e vaccine type as one factor and adjuvant as another factor), the Bonferroni-modified P value below which differences were regarded as significant was 0.0083.

| | Live Imiquod | Live Vehicle | PBS Imiquod | PBS Vehicle | KBMA Imiquod | KBMA Vehicle | HK Imiquod | HK Vehicle |
|---|---|---|---|---|---|---|---|---|
| PBS Vehicle | x | 0.919671 | 0.375822 | | 0.435298 | | 0.919671 | |
| PBS Imiquod | | x | | 0.000000 | | 0.045574 | | 0.014533 |
| Live Vehicle | | | x | 0.000002 | 0.913185 | | 0.43064 | |
| Live Imiquod | | | | x | | 0.000017 | | 0.000052 |
| KBMA Imiquod | | | | | x | 0.22348 | 0.495331 | |
| KBMA Vehicle | | | | | | x | | 0.575409 |
| HK Imiquod | | | | | | | x | 0.22062 |
| HK Vehicle | | | | | | | | x |

| | PBS | HK | KBMA | Live |
|---|---|---|---|---|
| PBS | x | 0.061622 | 0.052047 | 0.000008 |
| HK | | x | 0.930118 | 0.000413 |
| KBMA | | | x | 0.000497 |
| Live | | | | x |
| Bonferonni | | | | 0.008333 |
| Imiquod vs Vehicle | | | | 0.000054 |

DISCUSSION

Natural infection with visceralizing *Leishmania* species leads either to immunity or to sub-acute life-threatening infection. Ideal vaccine strategies could maximize the immunogenicity of metabolically active whole parasites while eliminating the danger of infection from the vaccine itself. Additionally, this response might be enhanced by a vaccine adjuvant that directs the host response toward useful antiparasitic immunity. We demonstrate that the process of psoralen treatment and UVA irradiation is adaptable to a eukaryotic organism, *Leishmania* chagasi. KBMA-LC are replication incompetent and show progressive but non-immediate diminution in metabolic activity. They are capable of invading macrophages in vitro and in vivo, making a complex life-cycle transition from the promastigote to amastigote form, and inducing a macrophages' nitric-oxide dependent microbicidal program. When given as a subcutaneous vaccine, they protect susceptible BALB/c mice from a virulent challenge of *L. chagasi*. However, unlike live-LC, KBMA-LC vaccination does not result in organomegaly and parasitosis when introduced intravenously. The TLR-7 agonist imiquimod, used as a topical adjuvant, enhances this protection and appears to do so by stimulating a favorable CD4 mediated Th-1 type anti-leishmanial immune response.

Throughout these studies, KBMA-LC are compared to live-LC and heat-killed-LC based on the preliminary assumptions that live-LC are immunogenic but unsafe and that heat-killed-LC are safe but inherently insufficiently immunogenic. These studies provide evidence of the safety and immunogenicity of KBMA-LC. In vitro, like live parasites, KBMA-LC invade macrophages, undergo a complex life-cycle change, and induce nitric oxide production. Heat killed LC do not demonstrate these features. KBMA-LC also invade liver cells in vivo, again like live-LC but unlike heat-killed-LC. The BALB/c mouse visceral leishmaniasis model is limited in that the natural history of disease in this model (asymptomatic organomegaly and parasitosis after intravenous infection with $10^7$ organisms) differs from the natural history of infection in the human host (organ-infiltration, organ-failure, and death after subcutaneous sandfly inoculation of $10^4$ organisms). Furthermore, the model of vaccine "protection" provided by high-dose live subcutaneous vaccination—i.e. the 30-50% reduction in liver parasite load at one month after high-dose intravenous infection—is not complete protection, but is the accepted preclinical model for predicting the utility of vaccinations in hypothetical human subjects. In studies of cytokine production and CD4 T-cell activation, live-LC appeared to be a more potent stimulator of IFN-γ responses than either KBMA-LC or heat-killed-LC, especially when mice were vaccinated in the presence of imiquimod. Also, these studies use a period of two weeks between the final vaccine boost and infectious challenge. Long term studies to determine the durability of immunization induced by these whole cell vaccines are currently underway.

Both in vitro (FIG. 8) and in vivo (FIG. 9D), KBMA-LC show evidence of safety compared with live-LC.

The KBMA strategy merits some comparison with the strategy of whole cell vaccination with *Leishmania* promastigotes attenuated by ionizing radiation or with other other radiation-attenuation kinetoplastidae, such as the *Plasmodium falciparum* radio-attenuated merozoite vaccine under investigation for the prevention of malaria. Biochemically, these approaches differ in that the strategy we describe seeks to generate non-mutagenic double-stranded DNA crosslinks to render parasites replication incompetent, while ionizing radiation strategies aim to mutagenize every treated parasite to achieve the goal of blocking replication. Whether this biochemical difference makes a difference in the ultimate immunogenicity of vaccines remains to be seen. The KBMA strategy shares with radioattenuated parasite vaccines the goal of generating a safe but metabolically active parasite for vaccination. In the present case, as well as in the cases of the radioattenuated L. major promastigotes described by Rivier et al or the radioattenuated P. falciparum vaccine parasites demonstrate the ability to invade a target cell and make an initial life cycle transformation.

The KBMA strategy represents another viable approach to whole cell vaccination. Other approaches using whole cell vaccines include radioattenuation, heat-inactivation, and targeted genetic modifications. Given that a significant number of vaccines approved by the United States Food and Drug Administration follow a whole cell strategy, expanding the options for this general approach is worthwhile. Moreover, the KBMA strategy might ultimately be combined with the targeted genetic modification of organisms approach to achieve complementary safety.

Our findings here demonstrate the usefulness of topical TLR agonists as adjuvants in a visceral leishmaniasis model. We also provide an immunological correlate of protection that imiquimod can shift the immune program towards a IFN-γ mediated Th1 cellular response with diminished production of cytokines associated with Th-2 or inhibitory IL-10 dominant programs.

Natural infections with intracellular pathogens as diverse as *Leishmania, Plasmodia*, and *Mycobacteria* produce cellular immune responses and variable resolution or progression of infections. The fact that some patients develop a protective immune response after natural infection will support the case for discovery of safe whole cell vaccinations. Diverse host immune responses suggest that a diverse antigen repertoire in a vaccine may be required for widespread public use. KBMA technology adds to the armamentarium of techniques that can be used to produce safe, whole cell vaccines. At the same time, the observation that natural infections with these pathogens do not consistently lead to rapid and durable protective immunity supports the use of adjuvants like topical imiquimod to overcome the immunomodulation induced by the parasite for self preservation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition for inducing an immune response in a vertebrate host against a protozoan parasite, said composition comprising:
    a protozoan parasite comprising a psoralen-modified DNA, whereby said protozoan parasite is killed but metabolically active (KBMA);
    wherein said composition is formulated for administration to a vertebrate; and
    when administered to a vertebrate induces an immune response in said vertebrate where said immune response is directed against the protozoan parasite.

2. The composition of claim 1, wherein said protozoan parasite comprises a DNA modified with a psoralen selected from the group consisting of psoralen, isopsoralen, TMP, HMT, 8-MOP, AMT, and S-59.

3. The composition of claim 1, wherein said composition further comprises an adjuvant.

4. The composition of claim 3, wherein said adjuvant comprises a toll-like receptor agonist.

5. The composition of claim 3, wherein said adjuvant comprises an agonist for TLR-7 and/or TLR-8.

6. The composition of claim 3, wherein said toll-like receptor agonist comprises an imidazoquinolinamine.

7. The composition of claim 3, wherein said toll-like receptor agonist comprises a nucleoside analogue.

8. The composition of claim 3, wherein said toll-like receptor agonist comprises one or more agents selected from the group consisting of imiquimod, resiquimod (R-848), 3M-001, 3M-002, flagellin, poly U, Loxoribine, and CPG-A DNA, CpG-C DNA, 7-thia-8-oxoguanosinyl, 7-deazaguanosinyl, and abrogate.

9. The composition of claim 1, wherein the protozoan parasite belongs to the phylum Apicomplexa, or Kinetoplastida.

10. The composition of claim 9, wherein the protozoan parasite belongs to a genus selected from the group consisting of *Plasmodium, Toxoplasma, Neospora, Eimeria, Theileria, Babesia, Cryptosporidium, Sarcocystis,* and *Leucocytozoon, Leishmania,* and *Trypansoma.*

11. The composition of claim 1, wherein said composition is formulated for administration by a method selected from the group consisting of topical administration, subcutaneous administration, intramuscular administration, intravenous administration, transdermal administration, inhalation administration, and oral administration.

12. The composition of claim 1, wherein said composition is formulated for administration to a vertebrate selected from the group consisting of bird, canine, equine, feline, porcine, bovine, human, and non-human primate.

\* \* \* \* \*

```
                        SEQUENCE LISTING

<160> NUMBER OF SEQ ID NOS: 127

<210> SEQ ID NO 1
<211> LENGTH: 6
<212> TYPE: PRT
<213> ORGANISM: Artificial
<220> FEATURE:
<223> OTHER INFORMATION: Synthetic lipopeptide.

<400> SEQUENCE: 1

Cys Ser Lys Lys Lys Lys
1               5

<210> SEQ ID NO 2
<211> LENGTH: 5
<212> TYPE: PRT
<213> ORGANISM: Artificial
<220> FEATURE:
<223> OTHER INFORMATION: Synthetic lipopeptide.

<400> SEQUENCE: 2

Cys Ser Ser Asn Ala
1               5

<210> SEQ ID NO 3
<211> LENGTH: 6
<212> TYPE: PRT
<213> ORGANISM: Artificial
<220> FEATURE:
<223> OTHER INFORMATION: Synthetic lipopeptide.

<400> SEQUENCE: 3

Cys Ser Lys Lys Lys Lys
1               5

<210> SEQ ID NO 4
<211> LENGTH: 12
<212> TYPE: PRT
<213> ORGANISM: Artificial
```

```
<220> FEATURE:
<223> OTHER INFORMATION: Synthetic lipopeptide.

<400> SEQUENCE: 4

Cys Ser Lys Lys Lys Lys Cys Ser Lys Lys Lys Lys
1               5                   10

<210> SEQ ID NO 5
<211> LENGTH: 6
<212> TYPE: PRT
<213> ORGANISM: Artificial
<220> FEATURE:
<223> OTHER INFORMATION: Synthetic lipopeptide.

<400> SEQUENCE: 5

Cys Ser Lys Lys Lys Lys
1               5

<210> SEQ ID NO 6
<211> LENGTH: 6
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(2)
<223> OTHER INFORMATION: r is g or a
<220> FEATURE:
<221> NAME/KEY: misc_feature
<222> LOCATION: (5)..(6)
<223> OTHER INFORMATION: y is t/u or c

<400> SEQUENCE: 6 rrcgyy                                                                    6

<210> SEQ ID NO 7
<211> LENGTH: 6
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: r is g or a
<220> FEATURE:
<221> NAME/KEY: misc_feature
<222> LOCATION: (5)..(6)
<223> OTHER INFORMATION: y is t/u or c

<400> SEQUENCE: 7 rtcgyy                                                                    6

<210> SEQ ID NO 8
<211> LENGTH: 5
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (4)..(5)
<223> OTHER INFORMATION: n is a, c, g, or t

<400> SEQUENCE: 8 tcgnn                                                                     5

<210> SEQ ID NO 9
<211> LENGTH: 4
```

```
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 9 ncgn                                                                  4

<210> SEQ ID NO 10
<211> LENGTH: 5
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 10 ntcgn                                                                 5

<210> SEQ ID NO 11
<211> LENGTH: 3
<212> TYPE: DNA
<213> ORGANISM: Artificial
<220> FEATURE:
<223> OTHER INFORMATION: Synthetic toll-like receptor (TLR) ligand

<400> SEQUENCE: 11 tcg                                                                   3

<210> SEQ ID NO 12
<211> LENGTH: 13
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 12
tcgnntcgnn tcg                                                        13

<210> SEQ ID NO 13
<211> LENGTH: 5
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t
```

```
<220> FEATURE:
<221> NAME/KEY: misc_feature
<222> LOCATION: (5)..(5)
<223> OTHER INFORMATION: n is a, c, g, or t

<400> SEQUENCE: 13 ntcgn                                                                       5

<210> SEQ ID NO 14
<211> LENGTH: 8
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(8)
<223> OTHER INFORMATION: n is a, c, g, or t

<400> SEQUENCE: 14 ntcgnnnn                                                                    8

<210> SEQ ID NO 15
<211> LENGTH: 8
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(2)
<223> OTHER INFORMATION: r is g or a
<220> FEATURE:
<221> NAME/KEY: misc_feature
<222> LOCATION: (5)..(5)
<223> OTHER INFORMATION: y is t/u or c

<400> SEQUENCE: 15 rrcgytcg                                                                    8

<210> SEQ ID NO 16
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 16 tcgtcg                                                                      6

<210> SEQ ID NO 17
<211> LENGTH: 24
<212> TYPE: DNA
<213> ORGANISM: Artificial
<220> FEATURE:
<223> OTHER INFORMATION: Synthetic toll-like receptor (TLR) ligand

<400> SEQUENCE: 17
tcgtcgtttt gtcgttttgt cgtt                                                 24

<210> SEQ ID NO 18
<211> LENGTH: 7
<212> TYPE: DNA
<213> ORGANISM: Artificial
<220> FEATURE:
<223> OTHER INFORMATION: Synthetic toll-like receptor (TLR) ligand
```

```
<220> FEATURE:
<221> NAME/KEY: misc_feature
<222> LOCATION: (4)..(7)
<223> OTHER INFORMATION: n is a, c, g, or t

<400> SEQUENCE: 18 tcgnnnn                                                                    7

<210> SEQ ID NO 19
<211> LENGTH: 4
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(4)
<223> OTHER INFORMATION: n is a, c, g, or t

<400> SEQUENCE: 19 nnnn                                                                       4

<210> SEQ ID NO 20
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t

<400> SEQUENCE: 20
ntcgtcgnnc gnncg                                                          15

<210> SEQ ID NO 21
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 21
ntcgtcgaac gttcg                                                          15

<210> SEQ ID NO 22
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 22
ntcgtcgttc gaacg                                                          15
```

<210> SEQ ID NO 23
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 23
ntcgtcgtac gtacg                                                    15

<210> SEQ ID NO 24
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 24
ntcgtcgatc gatcg                                                    15

<210> SEQ ID NO 25
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 25
ntcgtcgcgc gcgcg                                                    15

<210> SEQ ID NO 26
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 26
ntcgtcggcc ggccg                                                    15

<210> SEQ ID NO 27
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 27
ntcgtcgccc gggcg                                                    15

-continued

```
<210> SEQ ID NO 28
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 28
ntcgtcgggc gcccg                                                     15

<210> SEQ ID NO 29
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 29
ntcgtcgccc gttcg                                                     15

<210> SEQ ID NO 30
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 30
ntcgtcgggc gttcg                                                     15

<210> SEQ ID NO 31
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 31
ntcgtcgttc gcccg                                                     15

<210> SEQ ID NO 32
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 32
ntcgtcgttc gggcg                                                     15
```

<210> SEQ ID NO 33
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 33
ntcgtcgaac gcccg                                                    15

<210> SEQ ID NO 34
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 34
ntcgtcgaac gggcg                                                    15

<210> SEQ ID NO 35
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 35
ntcgtcgccc gaacg                                                    15

<210> SEQ ID NO 36
<211> LENGTH: 15
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t

<400> SEQUENCE: 36
ntcgtcgggc gaacg                                                    15

<210> SEQ ID NO 37
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 37 tcgttt                                                               6

<210> SEQ ID NO 38
<211> LENGTH: 7

```
<212> TYPE: DNA
<213> ORGANISM: Artificial
<220> FEATURE:
<223> OTHER INFORMATION: Synthetic toll-like receptor (TLR) ligand

<400> SEQUENCE: 38 tcgtttt                                                                       7

<210> SEQ ID NO 39
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 39 tcgcccc                                                                       7

<210> SEQ ID NO 40
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 40 tcgaaaa                                                                       7

<210> SEQ ID NO 41
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 41 tcgagat                                                                       7

<210> SEQ ID NO 42
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 42 ttcgttt                                                                       7

<210> SEQ ID NO 43
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 43 atcgttt                                                                       7

<210> SEQ ID NO 44
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 44 ctcgttt                                                                       7
```

```
<210> SEQ ID NO 45
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 45 gtcgttt                                                                  7

<210> SEQ ID NO 46
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 46 ttcgatt                                                                  7

<210> SEQ ID NO 47
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 47 atcgatt                                                                  7

<210> SEQ ID NO 48
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 48 ctcgatt                                                                  7

<210> SEQ ID NO 49
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 49 agcgct                                                                   6

<210> SEQ ID NO 50
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 50 agcgcc                                                                   6

<210> SEQ ID NO 51
<211> LENGTH: 6
<212> TYPE: DNA
<213> ORGANISM: Artificial
<220> FEATURE:
<223> OTHER INFORMATION: Synthetic toll-like receptor (TLR) ligand
```

```
<400> SEQUENCE: 51 agcgtt                                                              6

<210> SEQ ID NO 52
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 52 agcgtc                                                              6

<210> SEQ ID NO 53
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 53 aacgct                                                              6

<210> SEQ ID NO 54
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 54 aacgcc                                                              6

<210> SEQ ID NO 55
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 55 aacgtt                                                              6

<210> SEQ ID NO 56
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 56 aacgtc                                                              6

<210> SEQ ID NO 57
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 57 ggcgct                                                              6

<210> SEQ ID NO 58
<211> LENGTH: 6
```

```
<212> TYPE: DNA
<213> ORGANISM: Artificial
<220> FEATURE:
<223> OTHER INFORMATION: Synthetic toll-like receptor (TLR) ligand

<400> SEQUENCE: 58 ggcgcc                                                                     6

<210> SEQ ID NO 59
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 59 ggcgtt                                                                     6

<210> SEQ ID NO 60
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 60 ggcgtc                                                                     6

<210> SEQ ID NO 61
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 61 gacgct                                                                     6

<210> SEQ ID NO 62
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 62 gacgcc                                                                     6

<210> SEQ ID NO 63
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 63 gacgtt                                                                     6

<210> SEQ ID NO 64
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 64 gacgtc                                                                     6
```

```
<210> SEQ ID NO 65
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 65 gtcgtc                                                                      6

<210> SEQ ID NO 66
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 66 gtcgct                                                                      6

<210> SEQ ID NO 67
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 67 gtcgtt                                                                      6

<210> SEQ ID NO 68
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 68 gtcgcc                                                                      6

<210> SEQ ID NO 69
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 69 atcgtc                                                                      6

<210> SEQ ID NO 70
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 70 atcgct                                                                      6

<210> SEQ ID NO 71
<211> LENGTH: 6
<212> TYPE: DNA
<213> ORGANISM: Artificial
<220> FEATURE:
<223> OTHER INFORMATION: Synthetic toll-like receptor (TLR) ligand
```

```
<400> SEQUENCE: 71 atcgtt                                                              6

<210> SEQ ID NO 72
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 72 atcgcc                                                              6

<210> SEQ ID NO 73
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 73 tcgtcg                                                              6

<210> SEQ ID NO 74
<211> LENGTH: 9
<212> TYPE: DNA
<213> ORGANISM: Artificial
<220> FEATURE:
<223> OTHER INFORMATION: Synthetic toll-like receptor (TLR) ligand

<400> SEQUENCE: 74 tcgtcgtcg                                                           9

<210> SEQ ID NO 75
<211> LENGTH: 7
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (4)..(7)
<223> OTHER INFORMATION: n is a, c, g, or t

<400> SEQUENCE: 75 tcgnnnn                                                             7

<210> SEQ ID NO 76
<211> LENGTH: 7
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (5)..(7)
<223> OTHER INFORMATION: n is a, c, g, or t

<400> SEQUENCE: 76 tcgannn                                                             7

<210> SEQ ID NO 77
<211> LENGTH: 7
<212> TYPE: DNA
<213> ORGANISM: Artificial
<220> FEATURE:
<223> OTHER INFORMATION: Synthetic toll-like receptor (TLR) ligand
```

```
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(7)
<223> OTHER INFORMATION: n is a, c, g, or t

<400> SEQUENCE: 77 ntcgnnn                                                                     7

<210> SEQ ID NO 78
<211> LENGTH: 7
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 78 ntcgann                                                                     7

<210> SEQ ID NO 79
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 79 tcgtcga                                                                     7

<210> SEQ ID NO 80
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 80 tcgacgt                                                                     7

<210> SEQ ID NO 81
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 81 tcgaacg                                                                     7

<210> SEQ ID NO 82
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 82 tcgagat                                                                     7
```

<210> SEQ ID NO 83
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 83 tcgactc                                                                   7

<210> SEQ ID NO 84
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 84 tcgagcg                                                                   7

<210> SEQ ID NO 85
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 85 tcgattt                                                                   7

<210> SEQ ID NO 86
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 86 tcgcttt                                                                   7

<210> SEQ ID NO 87
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 87 tcggttt                                                                   7

<210> SEQ ID NO 88
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 88 tcgtttt                                                                   7

<210> SEQ ID NO 89
<211> LENGTH: 7
<212> TYPE: DNA
<213> ORGANISM: Artificial
<220> FEATURE:
<223> OTHER INFORMATION: Synthetic toll-like receptor (TLR) ligand

```
<400> SEQUENCE: 89 tcgtcgt                                                              7

<210> SEQ ID NO 90
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 90 atcgatt                                                              7

<210> SEQ ID NO 91
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 91 ttcgttt                                                              7

<210> SEQ ID NO 92
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 92 ttcgatt                                                              7

<210> SEQ ID NO 93
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 93 acgttcg                                                              7

<210> SEQ ID NO 94
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 94 aacgttc                                                              7

<210> SEQ ID NO 95
<211> LENGTH: 7
<212> TYPE: DNA
<213> ORGANISM: Artificial
<220> FEATURE:
<223> OTHER INFORMATION: Synthetic toll-like receptor (TLR) ligand

<400> SEQUENCE: 95 tgacgtt                                                              7

<210> SEQ ID NO 96
<211> LENGTH: 7
```

```
<212> TYPE: DNA
<213> ORGANISM: Artificial
<220> FEATURE:
<223> OTHER INFORMATION: Synthetic toll-like receptor (TLR) ligand

<400> SEQUENCE: 96 tgtcgtt                                                              7

<210> SEQ ID NO 97
<211> LENGTH: 6
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (4)..(6)
<223> OTHER INFORMATION: n is a, c, g, or t

<400> SEQUENCE: 97 tcgnnn                                                               6

<210> SEQ ID NO 98
<211> LENGTH: 6
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (5)..(6)
<223> OTHER INFORMATION: n is a, c, g, or t

<400> SEQUENCE: 98 tcgann                                                               6

<210> SEQ ID NO 99
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 99 tcgtcg                                                               6

<210> SEQ ID NO 100
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 100 aacgtt                                                               6

<210> SEQ ID NO 101
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 101 atcgat                                                               6

<210> SEQ ID NO 102
<211> LENGTH: 6
```

```
<212> TYPE: DNA
<213> ORGANISM: Artificial
<220> FEATURE:
<223> OTHER INFORMATION: Synthetic toll-like receptor (TLR) ligand

<400> SEQUENCE: 102 gtcgtt                                                                    6

<210> SEQ ID NO 103
<211> LENGTH: 6
<212> TYPE: DNA
<213> ORGANISM: Artificial
<220> FEATURE:
<223> OTHER INFORMATION: Synthetic toll-like receptor (TLR) ligand

<400> SEQUENCE: 103 gacgtt                                                                    6

<210> SEQ ID NO 104
<211> LENGTH: 5
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (4)..(5)
<223> OTHER INFORMATION: n is a, c, g, or t

<400> SEQUENCE: 104 tcgnn                                                                     5

<210> SEQ ID NO 105
<211> LENGTH: 5
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (5)..(5)
<223> OTHER INFORMATION: n is a, c, g, or t

<400> SEQUENCE: 105 tcgan                                                                     5

<210> SEQ ID NO 106
<211> LENGTH: 5
<212> TYPE: DNA
<213> ORGANISM: Artificial
<220> FEATURE:
<223> OTHER INFORMATION: Synthetic toll-like receptor (TLR) ligand

<400> SEQUENCE: 106 tcgat                                                                     5

<210> SEQ ID NO 107
<211> LENGTH: 5
<212> TYPE: DNA
<213> ORGANISM: Artificial
<220> FEATURE:
<223> OTHER INFORMATION: Synthetic toll-like receptor (TLR) ligand

<400> SEQUENCE: 107 tcgtt                                                                     5

<210> SEQ ID NO 108
<211> LENGTH: 5
```

```
<212> TYPE: DNA
<213> ORGANISM: Artificial
<220> FEATURE:
<223> OTHER INFORMATION: Synthetic toll-like receptor (TLR) ligand

<400> SEQUENCE: 108 tcgtc                                                                    5

<210> SEQ ID NO 109
<211> LENGTH: 4
<212> TYPE: DNA
<213> ORGANISM: Artificial
<220> FEATURE:
<223> OTHER INFORMATION: Synthetic toll-like receptor (TLR) ligand

<400> SEQUENCE: 109 tcga                                                                     4

<210> SEQ ID NO 110
<211> LENGTH: 4
<212> TYPE: DNA
<213> ORGANISM: Artificial
<220> FEATURE:
<223> OTHER INFORMATION: Synthetic toll-like receptor (TLR) ligand

<400> SEQUENCE: 110 tcgt                                                                     4

<210> SEQ ID NO 111
<211> LENGTH: 4
<212> TYPE: DNA
<213> ORGANISM: Artificial
<220> FEATURE:
<223> OTHER INFORMATION: Synthetic toll-like receptor (TLR) ligand
<220> FEATURE:
<221> NAME/KEY: misc_feature
<222> LOCATION: (4)..(4)
<223> OTHER INFORMATION: n is a, c, g, or t

<400> SEQUENCE: 111 tcgn                                                                     4

<210> SEQ ID NO 112
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 112 agcgctcg                                                                 8

<210> SEQ ID NO 113
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 113 agcgcccg                                                                 8

<210> SEQ ID NO 114
<211> LENGTH: 8
<212> TYPE: DNA
<213> ORGANISM: Artificial
<220> FEATURE:
<223> OTHER INFORMATION: Synthetic toll-like receptor (TLR) ligand
```

```
<400> SEQUENCE: 114 agcgttcg                                                              8

<210> SEQ ID NO 115
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 115 agcgtccg                                                              8

<210> SEQ ID NO 116
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 116 aacgctcg                                                              8

<210> SEQ ID NO 117
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 117 aacgcccg                                                              8

<210> SEQ ID NO 118
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 118 aacgttcg                                                              8

<210> SEQ ID NO 119
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 119 aacgtccg                                                              8

<210> SEQ ID NO 120
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 120 ggcgctcg                                                              8

<210> SEQ ID NO 121
<211> LENGTH: 8
```

```
<212> TYPE: DNA
<213> ORGANISM: Artificial
<220> FEATURE:
<223> OTHER INFORMATION: Synthetic toll-like receptor (TLR) ligand

<400> SEQUENCE: 121 ggcgcccg                                                                  8

<210> SEQ ID NO 122
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 122 ggcgttcg                                                                  8

<210> SEQ ID NO 123
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 123 ggcgtccg                                                                  8

<210> SEQ ID NO 124
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 124 gacgctcg                                                                  8

<210> SEQ ID NO 125
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 125 gacgcccg                                                                  8

<210> SEQ ID NO 126
<211> LENGTH: 8
<212> TYPE: DNA
<213> ORGANISM: Artificial
<220> FEATURE:
<223> OTHER INFORMATION: Synthetic toll-like receptor (TLR) ligand

<400> SEQUENCE: 126 gacgttcg                                                                  8

<210> SEQ ID NO 127
<211> LENGTH: 8
<212> TYPE: DNA
```

```
<213> ORGANISM: Artificial
<220> FEATURE:
<223> OTHER INFORMATION: Synthetic toll-like receptor (TLR) ligand

<400> SEQUENCE: 127 gacgtccg                                                                8
```